(12) United States Patent
Miyake et al.

(10) Patent No.: US 8,598,380 B2
(45) Date of Patent: Dec. 3, 2013

(54) METHOD FOR PRODUCING ARYLOXYTITANIUM COMPOSITION AND ARYLOXYTITANIUM COMPOSITION

(75) Inventors: Nobuhisa Miyake, Tokyo (JP); Budianto Nishiyama, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 13/579,658

(22) PCT Filed: Feb. 23, 2011

(86) PCT No.: PCT/JP2011/054011
§ 371 (c)(1), (2), (4) Date: Aug. 17, 2012

(87) PCT Pub. No.: WO2011/105439
PCT Pub. Date: Sep. 1, 2011

(65) Prior Publication Data
US 2012/0316355 A1   Dec. 13, 2012

(30) Foreign Application Priority Data

Feb. 23, 2010  (JP) ................................ 2010-037925
Feb. 23, 2010  (JP) ................................ 2010-037926

(51) Int. Cl.
*C07F 7/28*  (2006.01)
*B01J 31/00* (2006.01)
*C07C 69/76* (2006.01)

(52) U.S. Cl.
USPC ................................. 556/54; 560/8; 502/150

(58) Field of Classification Search
USPC ................................................ 556/54; 560/8
See application file for complete search history.

(56) References Cited

U.S. PATENT DOCUMENTS

| | | |
|---|---|---|
| 2,880,221 A | 3/1959 | Haslam |
| 5,380,908 A | 1/1995 | Murata et al. |
| 5,734,004 A | 3/1998 | Kuhling et al. |
| 5,760,156 A | 6/1998 | Inoki et al. |
| 5,872,275 A | 2/1999 | Komiya et al. |
| 6,197,918 B1 | 3/2001 | Uno et al. |
| 6,262,210 B1 | 7/2001 | Tojo et al. |
| 2008/0177099 A1 | 7/2008 | Miyake |

FOREIGN PATENT DOCUMENTS

| | | |
|---|---|---|
| EP | 0780361 A1 | 6/1997 |
| JP | S64-052786 A | 2/1989 |
| JP | H01-129031 A | 5/1989 |
| JP | H06-157410 A | 6/1994 |
| JP | H08-259504 A | 10/1996 |
| JP | H08-259505 A | 10/1996 |
| JP | H09-059224 A | 3/1997 |
| JP | H09-110805 A | 4/1997 |
| JP | H09-165357 A | 6/1997 |
| JP | H09-169704 A | 6/1997 |
| JP | H09-194437 A | 7/1997 |
| JP | H11-092429 A | 4/1999 |
| JP | 2000-072721 A | 3/2000 |
| JP | 2000-086769 A | 3/2000 |
| JP | 2000-191596 A | 7/2000 |
| JP | 2003-238487 A | 8/2003 |
| JP | 3528997 B2 | 3/2004 |
| JP | 2004-307400 A | 11/2004 |
| TW | 2006-33974 A | 10/2006 |
| WO | 97/11049 A1 | 3/1997 |
| WO | 2004/069740 A1 | 8/2004 |
| WO | 2006/067982 A1 | 6/2006 |
| WO | 2006/068053 A1 | 6/2006 |

OTHER PUBLICATIONS

Du et al., "Novel catalytic systems containing n-BuSn(O)OH for the transesterification of dimethyl carbonate and phenol," Journal of Molecular Catalysis A: Chemical 246: 200-2005 (2006).

Niu et al., "Transesterification of dimethyl carbonate and phenol to diphenyl carbonate catalyzed by samarium diiodide," Journal of Molecular Catalysis A: Chemical 259: 293-295 (2006).

Niu et al., "Transesterification of dimethyl carbonate and phenol to diphenyl carbonate catalyzed by titanocene complexes," Catalysis Communications, 8: 355-358 (2007).

International Search Report issued in International Application No. PCT/JP2011/054011 dated Apr. 5, 2011.

Search Report issue in International Application No. PCT/JP2011/054018 dated May 24, 2011.

Office Action issued in corresponding Taiwanese Patent Application No. 100105940 dated Jun. 24, 2013.

*Primary Examiner* — Porfirio Nazario Gonzalez
(74) *Attorney, Agent, or Firm* — Morgan, Lewis & Bockius LLP

(57) ABSTRACT

The present invention provides a method for producing an aryloxytitanium composition that can solve the problems of the clogging of the storage tank, the piping, the pump, and the like during storage and transfer, and the like, and a decrease in catalytic activity which occurs during long-term storage, and is extremely preferred as a catalyst for the production of a diaryl carbonate. A method for producing an aryloxytitanium composition, comprising a step (1) of adding a diaryl carbonate to an organic oxytitanium composition having an R—O—Ti linkage, wherein R represents an organic group containing 1 to 20 carbon atoms, and evaporating a component having a lower boiling point than that of the diaryl carbonate, together with the diaryl carbonate, so as to obtain an aryloxytitanium composition.

28 Claims, 2 Drawing Sheets

METHOD FOR PRODUCING ARYLOXYTITANIUM COMPOSITION AND ARYLOXYTITANIUM COMPOSITION

The present application is a U.S. National Phase Application of International Application No. PCT/JP2011/054011 filed Feb. 23, 2011, which claims the benefit of priority of Japanese Application Nos. 2010-037925 filed Feb. 23, 2010 and 2010-037926 filed Feb. 23, 2010, the disclosures of which are incorporated herein by reference in their entireties.

TECHNICAL FIELD

The present invention relates to a method for producing an aryloxytitanium composition, and an aryloxytitanium composition.

BACKGROUND ART

Aromatic carbonates have attracted attention as raw materials used to produce aromatic polycarbonates, whose usefulness as engineering plastics has been increasing in recent years, without using poisonous phosgene.

Regarding techniques for producing diaryl carbonates as raw materials for the production of aromatic carbonates, useful catalysts and methods for producing the same have been studied.

For example, Ti-containing compounds, such as organic titanates having a Ti—O—Ti linkage, are known as compounds having high activity and being useful as catalysts for reactions for obtaining diaryl carbonates using dialkyl carbonates and aromatic hydroxy compounds as starting materials, and methods for producing organic titanates having at least one Ti—O—Ti linkage are disclosed (for example, see Patent Document 1 to 3).

LIST OF PRIOR ART DOCUMENTS

Patent Document

Patent Document 1: International Publication No. WO 2006/68053
Patent Document 2: International Publication No. WO 2006/67982
Patent Document 3: U.S. Pat. No. 2,880,221

SUMMARY OF INVENTION

Problems to be Solved by the Invention

However, problems remain in the handling of the Ti-containing compounds, such as organic titanates having a Ti—O—Ti linkage.

In other words, when alkoxytitaniums are used as catalysts for the production of diaryl carbonates, quality degradation is caused if a metal component derived from the catalysts remains in the diaryl carbonates.

Ti-containing compound catalysts that are preferred in terms of advantageously progressing equilibrium reactions included in the reactions for obtaining diaryl carbonates are aryloxytitaniums having no alkoxy group, but the aryloxytitaniums have a very high melting point (for example, the melting point of titanium tetraphenoxide is about 155° C.), and therefore, a problem of the aryloxytitaniums is that solidification and clogging occur unless the storage tank, the piping, the pump, and the like are constantly kept at high temperature.

Further, as a result of the study of the present inventors, another problem is that when aryloxytitaniums are stored at high temperature, the activity as catalysts for the production of diaryl carbonates decreases significantly.

Further, tetraaryloxytitaniums are known to be effective as catalysts for the production of diaryl carbonates, and conventionally, a step of producing aryloxy compounds is performed, adjacent to a site for a step of producing diaryl carbonates, to produce tetraaryloxytitaniums, in view of the problems based on temperature control, transfer, and storage described above. However, study is still insufficient for methods for producing diaryl carbonates by transferring titanium complex catalysts having an aryloxy group, such as tetraaryloxytitaniums, and techniques for obtaining titanium complex catalysts having an aryloxy group that can endure the above storage.

Further, handling when transfer or storage is continued over a long period, methods for producing catalysts compatible therewith, and catalyst compositions that can provide the highest productivity are also unknown.

Accordingly, it is an object of the present invention to provide a method for producing an aryloxytitanium composition and an aryloxytitanium composition that can solve the above-described problems, as a catalyst used in reacting an aliphatic carbonate with an aromatic monohydroxy compound to produce an aromatic carbonate while removing an alcohol as by-product out of the reaction systems.

Means for Solving the Problems

The present inventors have diligently studied the above problems over and over, and, as a result, found that the above-described conventional problems are solved by a production method comprising a step of adding a particular amount of a diaryl carbonate to a particular organic oxytitanium composition and evaporating a component having a lower boiling point than that of the diaryl carbonate, together with the diaryl carbonate.

The present inventors have found that the above-described conventional problems are solved by a composition containing an aryloxytitanium and a diaryl carbonate in a particular ratio.

Specifically, it has been found that an aryloxytitanium (or composition) itself does not melt unless it is at high temperature, but when it is mixed with a diaryl carbonate, the effect of lowering the melting point is large, and further, the composition mixed with the diaryl carbonate can be stored over a long period. It has been found that such a composition containing an aryloxytitanium and a diaryl carbonate in a particular ratio is preferred as a catalyst for the production of a diaryl carbonate.

On the other hand, an aromatic hydroxy compound and a dialkyl carbonate that are raw materials for the synthesis of the aryloxytitanium (or composition) have also been studied for a similar purpose. However, the above effects are not seen, and in addition, the solubility is also low, and a decrease in activity occurs during storage. It has also been found that the above effects are specific to the aryloxytitanium (or composition).

Further, it has also been found that when a composition obtained by adding a diaryl carbonate to an aryloxytitanium or an aryloxypolytitanoxane (or a composition thereof) and evaporating a component having a lower boiling point than that of the diaryl carbonate is used as a catalyst for the production of a diaryl carbonate, the problems of coloration and the like can be solved. This is considered to be because the low boiling component containing a titanium atom can be removed, and a chlorine-containing component can also be secondarily removed.

It has been found that when the diaryl carbonate obtained using the aryloxytitanium composition in the present embodiment as a catalyst is used as a raw material for a melt process polycarbonate, there is no coloration, and the adjustment of the amount of the polymerization catalyst is also easy, and the diaryl carbonate has high quality, leading to the completion of the present invention.

Specifically, the present invention is as follows.

[1]

A method for producing an aryloxytitanium composition, comprising a step (1) of adding a diaryl carbonate to an organic oxytitanium composition having an R—O—Ti linkage, wherein R represents an organic group containing 1 to 20 carbon atoms, and evaporating a component having a lower boiling point than that of the diaryl carbonate, together with the diaryl carbonate, so as to obtain an aryloxytitanium composition, wherein an amount of the diaryl carbonate used in the step (1) is 0.1 to 50 molar equivalents with respect to total moles of Ti atoms contained in the organic oxytitanium composition having the R—O—Ti linkage.

[2]

The method for producing the aryloxytitanium composition according to the [1], wherein a temperature in evaporating the component having the lower boiling point than that of the diaryl carbonate in the step (1) is in a range of 50° C. to 250° C., and in the aryloxytitanium composition obtained in the step (1), a content of titanium atoms is 1% by mass or more and 15% by mass or less, and a content of the diaryl carbonate is 50% by mass or more and 95% by mass or less.

[3]

The method for producing the aryloxytitanium composition according to the [1] or [2], wherein in the step (1), the following step (A) and step (B) are sequentially performed:

step (A): a step of reacting an alkyloxytitanium composition with an aromatic hydroxy compound and evaporating an alcohol as by-product, by distillation, so as to obtain a crude aryloxytitanium composition; and step (B): a step of adding a diaryl carbonate to the crude aryloxytitanium composition and evaporating a component having a lower boiling point than that of the diaryl carbonate, together with the diaryl carbonate, so as to obtain an aryloxytitanium composition.

[4]

The method for producing the aryloxytitanium composition according to any one of the [1] to [3], comprising further carrying out the following step (C):

step (C): a step of adjusting a component ratio of the aryloxytitanium composition and the diaryl carbonate.

[5]

The method for producing the aryloxytitanium composition according to the [3], wherein the alkyloxytitanium composition is an alkyloxytitanium composition obtained by sequentially or simultaneously performing step (X): a step of adding water to a tetraalkoxytitanium to react the tetraalkoxytitanium with the water so as to obtain a partial hydrolysis reaction solution, and step (Y): a step of evaporating an alcohol as by-product, from the hydrolysis reaction solution.

[6]

The method for producing the aryloxytitanium composition according to any one of the [1] to [5], wherein an aryloxy group constituting the aryloxytitanium is represented by the following formula (ArO):

[Formula 1]

(ArO)

wherein a ring A represents an organic group having 6 to 20 carbon atoms, containing an aromatic group to which an oxygen atom bonded to Ti is bonded at any position keeping aromaticity, and may be a single ring or a plurality of rings, or a heterocyclic ring, and/or may be substituted by another substituent.

[7]

The method for producing the aryloxytitanium composition according to the [5], wherein an amount of the water in the step (X) is 0.1 to 0.92 molar equivalents with respect to the tetraalkoxytitanium.

[8]

The method for producing the aryloxytitanium composition according to any one of the [1] to [7], comprising carrying out the step (1) or the step (B) in multiple batches, or continuously.

[9]

An aryloxytitanium composition produced by the method for producing the aryloxytitanium composition according to any one of the [1] to [8].

[10]

An aryloxytitanium composition comprising:

an aryloxytitanium composition produced by the method for producing the aryloxytitanium composition according to any one of the [1] to [8]; and a diaryl carbonate.

[11]

The method for producing the aryloxytitanium composition according to any one of the [1] to [8], wherein the diaryl carbonate is diphenyl carbonate.

[12]

The method for producing the aryloxytitanium composition according to any one of the [1] to [8], wherein an aryloxy group constituting the aryloxytitanium is the same aryloxy group as an aryloxy group constituting the diaryl carbonate.

[13]

A method for stabilizing an aryloxytitanium composition, comprising:

a step of reacting an alkyloxytitanium composition with an aromatic hydroxy compound and evaporating an alcohol as by-product, by distillation, so as to obtain a crude aryloxytitanium composition (step (A)); and a step of adding a diaryl carbonate to the crude aryloxytitanium composition and evaporating a component having a lower boiling point than that of the diaryl carbonate, together with the diaryl carbonate, so as to obtain an aryloxytitanium composition (step (B)), wherein an amount of the diaryl carbonate used in the step (B) is 0.1 to 50 molar equivalents with respect to total moles of Ti atoms contained in the crude aryloxytitanium composition, and a temperature in evaporating the component having a lower boiling point than that of the diaryl carbonate in the step (B) is in a range of 50° C. to 250° C.

[14]
The method for stabilizing the aryloxytitanium composition according to the [13], wherein in the aryloxytitanium composition obtained in the step (B), a content of titanium atoms is 1% by mass or more and 15% by mass or less, and a content of the diaryl carbonate is 50% by mass or more and 95% by mass or less.

[15]
An aryloxytitanium composition comprising:
an aryloxytitanium; and
a diaryl carbonate, wherein
a content of titanium atoms constituting the aryloxytitanium is 1% by mass or more and 15% by mass or less.

[16]
The aryloxytitanium composition according to the [15], wherein a content of the diaryl carbonate is 50% by mass or more and 95% by mass or less, and a content of a compound having a boiling point of 150° C. or less is 1000 ppm or less.

[17]
The aryloxytitanium composition according to the [15] or [16], wherein the content of titanium atoms constituting the aryloxytitanium is 5% by mass or more and 10% by mass or less.

[18]
The aryloxytitanium composition according to any one of the [15] to [17], wherein a total content of the aryloxytitanium and the diaryl carbonate is 50% by mass or more.

[19]
The aryloxytitanium composition according to any one of the [15] to [18], wherein titanium constituting the aryloxytitanium is a tetravalent titanium.

[20]
The aryloxytitanium composition according to any one of the [15] to [19], wherein an aryloxy group constituting the aryloxytitanium is an aryloxy group having 6 or 7 carbon atoms.

[21]
The aryloxytitanium composition according to any one of the [15] to [20], wherein the composition is solid or liquid.

[22]
The aryloxytitanium composition according to any one of the [15] to [21], wherein the aryloxytitanium is an aryloxypolytitanoxane.

[23]
The aryloxytitanium composition according to the [22], wherein the aryloxypolytitanoxane comprises
one or more types of aryloxypolytitanoxane having one or more Ti—O—Ti linkages in one molecule.

[24]
A method for producing a diaryl carbonate, using the aryloxytitanium composition according to any one of the [15] to [23] as a catalyst, comprising
performing transesterification and disproportionation reactions, using a dialkyl carbonate, an aromatic hydroxy compound, and the aryloxytitanium composition, so as to produce a diaryl carbonate.

[25]
A catalyst for production of a diaryl carbonate, comprising an aryloxytitanium and a diaryl carbonate, wherein
a content of titanium atoms constituting the aryloxytitanium is 1% by mass or more and 15% by mass or less.

[26]
A method for producing a diaryl carbonate, comprising performing transesterification reaction and disproportionation reaction, using a dialkyl carbonate and an aromatic hydroxy compound, in the presence of the catalyst for production of the diaryl carbonate according to the [25], so as to produce a diaryl carbonate.

[27]
The method for producing the diaryl carbonate according to the [26], comprising a step of separating the diaryl carbonate from a reaction product obtained by the disproportionation reaction.

[28]
The method for producing the diaryl carbonate according to the [27], further comprising a step of recycling the reaction product, from which the diaryl carbonate is separated, into the transesterification reaction or the disproportionation reaction.

Advantages of the Invention

The present invention provides a method for producing an aryloxytitanium composition and an aryloxytitanium composition that can solve the problems of the clogging of the storage tank, the piping, the pump, and the like during storage and transfer, and the like, and a decrease in catalytic activity which occurs during long-term storage, and is extremely preferred as a catalyst for a production of a diaryl carbonate.

MODE FOR CARRYING OUT THE INVENTION

Figure 1:
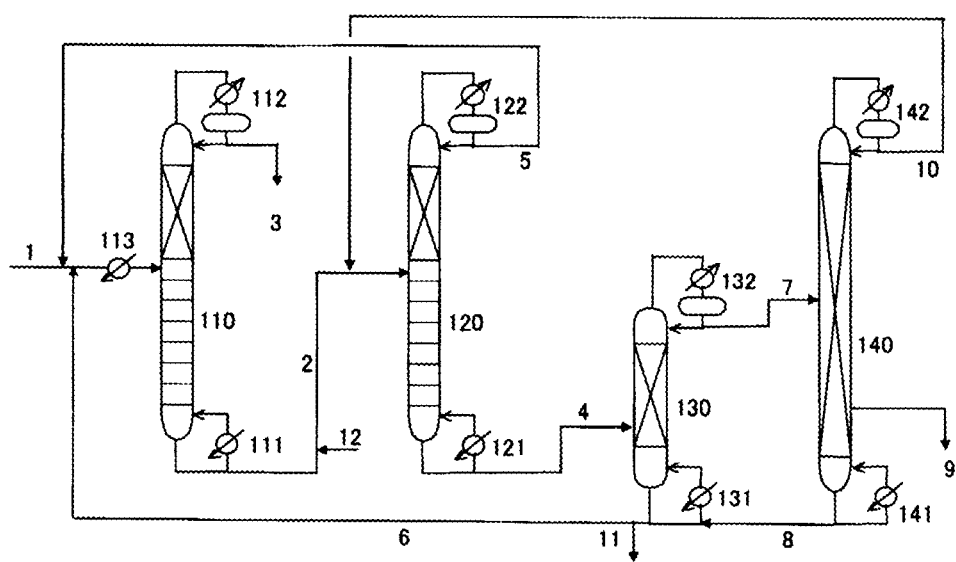
FIG. 1 shows a schematic configuration diagram of one example of an apparatus for producing a diaryl carbonate.

A mode for carrying out the present invention (hereinafter referred to as the present embodiment) will be described below with reference to the drawings.
The present embodiment below is an illustration for describing the present invention and does not limit the present invention to the following content. Appropriate modifications can be made to the present invention without departing from the spirit thereof.
In the drawings, positional relationship, such as top, bottom, left, and right, is based on the positional relationship shown in the drawings, unless otherwise specified. Further, a dimensional ratio in the drawings is not limited to the ratio shown.

[Method for Producing Aryloxytitanium Composition]
A method for producing an aryloxytitanium composition in the present embodiment comprises a step (1) of adding a diaryl carbonate to an organic oxytitanium composition having an R—O—Ti linkage, wherein R represents an organic group containing 1 to 20 carbon atoms, and evaporating a component having a lower boiling point than that of the diaryl carbonate, together with the diaryl carbonate, so as to obtain an aryloxytitanium composition, wherein an amount of the above diaryl carbonate used in the above step (1) is 0.1 to 50 molar equivalents with respect to total moles of Ti atoms contained in the above organic oxytitanium composition having the R—O—Ti linkage.

By evaporating the component having the lower boiling point than that of the diaryl carbonate in the above step (1), an aryloxytitanium composition that has high stability during transfer and/or storage can be obtained. The aryloxytitanium composition is preferred as a catalyst for the production of a diaryl carbonate.

A temperature in evaporating the component having the lower boiling point than that of the diaryl carbonate in the above step (1) is preferably in the range of 50° C. to 250° C. In the aryloxytitanium composition obtained in the above step (1), a content of titanium atoms is preferably 1% by mass or more and 15% by mass or less, and a content of the diaryl carbonate is preferably 50% by mass or more and 95% by mass or less.

By controlling the temperature in evaporating the component having the lower boiling point than that of the diaryl carbonate, and controlling each component of the obtained aryloxytitanium composition to a particular amount, an aryloxytitanium composition that has higher stability during transfer and/or storage can be obtained. The aryloxytitanium composition is extremely preferred as a catalyst for a production of a diaryl carbonate.

In the method for producing the aryloxytitanium composition in the present embodiment, regarding the above step (1), further specifically, the following step (A) and step (B) can be sequentially performed:

step (A): a step of reacting an alkyloxytitanium composition with an aromatic hydroxy compound and evaporating an alcohol as by-product, by distillation, so as to obtain a crude aryloxytitanium composition; and step (B): a step of adding a diaryl carbonate to the above crude aryloxytitanium composition and evaporating a component having a lower boiling point than that of the diaryl carbonate, together with the diaryl carbonate, so as to obtain an aryloxytitanium composition.

These step (A) and step (B) will be described later.

First, compounds and the like used in the present embodiment will be described.

(Organic Oxytitanium Composition Having R—O—Ti Linkage)

The organic oxytitanium composition having the R—O—Ti linkage is an organic oxytitanium composed of a tetravalent Ti atom, in which the Ti atom is substituted by an R—O— group, wherein R represents an organic group.

Here, the "organic oxytitanium composition having the R—O—Ti linkage" means that not only one "organic oxytitanium having the R—O—Ti linkage" is present, but also a plurality of "organic oxytitaniums having the R—O—Ti linkage" may be mixed. This is due to the fact that it is difficult to exactly identify the structure.

The organic oxytitanium composition may be a monomer or may be a polymer (organic polytitanoxane).

The above "polytitanoxane" is defined.

The "polytitanoxane" refers to an organic-inorganic hybrid compound comprising a Ti—O—Ti repeating structure and an R—O—Ti linkage, wherein R represents an organic group, herein. For the structure of polytitanoxane compounds, there are reports in which the structure is presumed (for example, Kogyo Kagaku Zasshi (Journal of the Chemical Society of Japan, Industrial Chemistry Section), vol. 64, p. 885-888 (1961), and Nature, p. 273-274 (1961)), and reports in which a particular linkage (for example, Ti—O—Ti) is allegedly detected (for example, Japanese Patent Laid-Open No. 2004-256719).

The Ti atom used in the present embodiment is a tetravalent Ti atom. A polytitanoxane composition comprising at least one polytitanoxane comprising a structural unit selected from the following general formulas (1), (2), (3), and (4) is the organic polytitanoxane used in the present embodiment.

In other words, the organic polytitanoxane may have a structure in which the structural units shown in the following formulas are combined to form a linear, branched, or cyclic structure each other via the Ti—O—Ti linkage, or a structure comprising a combination thereof.

[Formula 2]

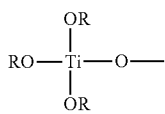
(1)

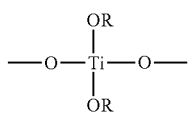
(2)

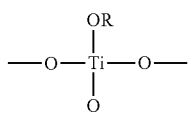
(3)

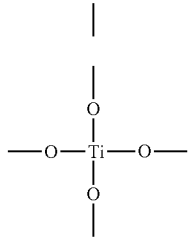
(4)

In the above formulas (1) to (4), R represents an organic group.

The R group is an organic group described in Nomenclature (IUPAC Nomenclature of Organic Chemistry) prescribed by IUPAC (The International Union of Pure and Applied Chemistry).

A plurality of R groups are contained in the above organic polytitanoxane. They may be the same or different.

For the structure forming a branched or cyclic structure, for example, those shown in the following formulas (a) and (b) are considered.

[Formula 3]

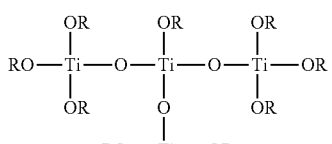
(a)

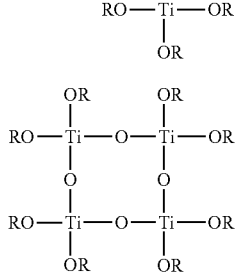
(b)

When the IUPAC Rules, and the Nomenclature Rules prescribed by IUPAC also shown hereinafter (except for cases where other years' IUPAC Recommendations and the like are specially cited) herein are cited below, "Yukikagaku・Seikagaku Meimeiho (Organic Chemical and Biochemical Nomenclature)" (revised second edition published in 1992, Nankodo Co., Ltd., Japan) is cited, which is based on the edition including all the rules of organic chemistry and biochemistry, and Japanese transliteration rules, published as a separate volume of "Kagaku no Ryoiki (The Area of Chemistry)" in 1980, based on Recommendations 1979, and in which all subsequent revisions and recommendations are added.

"Organic" refers to generally a group of compounds that are subjects of the nomenclature disclosed in the book.

The subjects ("organic") may be subjects described in Recommendations issued in 1993 (when it is difficult to obtain the above-described book published in Japan, Recommendations 1979 and Recommendations 1993 may be referred to).

However, the above-described "organic" compounds that are subjects of the Nomenclature also include organometallic compounds and metal complexes.

"Organic" and/or "organic groups" and/or "substituents" and the like, and the compounds used in the present embodiment will be described herein below. They are composed of an atom not including a metal atom and/or a semimetal, unless otherwise specified.

Further preferably, "organic compounds," "organic groups," and "substituents" composed of an atom selected from H (hydrogen atom), C (carbon atom), N (nitrogen atom), O (oxygen atom), and S (sulfur atom) are used in the present embodiment.

The limitations "aliphatic" and "aromatic" are frequently used herein. According to the IUPAC Rules, it is described that organic compounds are classified into aliphatic compounds and aromatic compounds, and the definition of aliphatic compounds is groups according to the aliphatic compounds based on IUPAC Recommendations 1995.

In the Recommendations, aliphatic compounds are defined as "Acyclic or cyclic, saturated or unsaturated carbon compounds, excluding aromatic compounds."

An aliphatic group often used herein is a group comprising the above aliphatic compound.

For a group, for example, the R portion obtained by removing a hydrogen atom from the aliphatic compound RH is defined as a monovalent aliphatic group.

Aliphatic and aliphatic groups include all of saturated and unsaturated, and acyclic and cyclic, and refer to the above "organic compounds," "organic groups," and "substituents" composed of an atom selected from H (hydrogen atom); C (carbon atom); N (nitrogen atom); O (oxygen atom); S (sulfur atom); Si (silicon atom); and a halogen atom selected from Cl (chlorine atom), Br (bromine atom), and I (iodine atom).

A case where an aromatic group is bonded to an aliphatic group, such as an aralkyl group, is often described as "an aliphatic group substituted by an aromatic group" or "a group comprising an aliphatic group to which an aromatic group is bonded" in such a manner.

This is based on reactivity in the present embodiment, and the nature regarding the reaction of groups, such as aralkyl groups, is extremely similar to the reactivity of aliphatic groups, rather than aromaticity.

Non-aromatic reactive groups including aralkyl groups and alkyl groups are often described as "aliphatic groups which may be aromatically substituted," "aromatically substituted aliphatic groups," "aliphatic groups to which aromatic groups are bonded," or the like.

When the general formulas of the compounds used herein are described, definitions according to the above-described Nomenclature Rules prescribed by IUPAC are used. However, in the description of the compounds used in the present embodiment, in order to clarify the feature of the structure, coined words, such as an "organic polytitanoxane" and an "aryloxytitanium," are used, and for the names of particular groups and illustrated compound names, trivial names are often used.

The number of atoms and the number of substituents are often described herein. They all represent zero or a positive integer (zero is often a positive integer). However, when a composition ratio formula is represented, positive numbers are used.

This is notation often used for the notation of inorganic compounds and organic-inorganic hybrid compounds.

The above R group is preferably a group composed of a carbon atom, a hydrogen atom, and/or an oxygen atom, and it is any of an aliphatic group, an aromatic group, and a group in which an aliphatic group and an aromatic group are bonded to each other, and it represents an acyclic hydrocarbon group, a cyclic hydrocarbon group (a group such as, for example, a monocyclic hydrocarbon group, a condensed polycyclic hydrocarbon group, a bridged cyclic hydrocarbon group, a spiro hydrocarbon group, a ring assembly hydrocarbon group, a cyclic hydrocarbon group with a side chain, a heterocyclic group, a heterocyclic spiro group, or a bridged heterocyclic group), a group in which one or more groups selected from the above acyclic hydrocarbon group and the above cyclic hydrocarbon group are bonded, and a group in which these groups are linked via covalent bonds to a particular nonmetal atom (carbon or oxygen).

The above covalent bond to the particular nonmetal atom (carbon or oxygen) refers to, for example, a state in which a group represented by the following formulas (5) to (8) and the above-described group are covalently bonded to each other.

[Formula 4]

 (5)

 (6)

 (7)

 (8)

Among the R groups as described above, the R group preferably used in the present embodiment is selected from the group consisting of an aliphatic group, an aromatic group, and a group in which an aliphatic group and an aromatic group are bonded to each other, considering that a side reaction is less likely to occur, and is preferably a group selected from the group consisting of an acyclic hydrocarbon group and a cyclic hydrocarbon group (a monocyclic hydrocarbon group, a condensed polycyclic hydrocarbon group, a bridged cyclic hydrocarbon group, a spiro hydrocarbon group, a ring assembly hydrocarbon group, and a cyclic hydrocarbon group with a side chain), and a group in which at least one group selected from the group is bonded (groups substituted by each other), which contain 1 to 20 carbon atoms.

Considering the flowability of the above organic oxytitanium composition having the R—O—Ti linkage, and the like, the R group is preferably a group containing 1 to 10 carbon atoms, more preferably a group containing 1 to 7 carbon atoms.

A more preferred R group is a group selected from a group in which at least one or more selected from the group consisting of an alkyl group, a cycloalkyl group, and an aryl group are bonded to each other, and a group in which at least one or more selected from the group consisting of an alkyl group, a cycloalkyl group, and an aryl group are formed via a linkage selected from the above formulas (5) to (8).

Examples of such an R group include a methyl group, an ethyl group, a propyl group (isomers), a butyl group (isomers), a pentyl group (isomers), a hexyl group (isomers), a heptyl group (isomers), a cyclopropyl group, a cyclobutyl group, a cyclopentyl group, a cyclohexyl group, a cycloheptyl group, a cyclopropylmethyl group, a cyclobutylmethyl group, a cyclopentylmethyl group, a cyclohexylmethyl group, a phenyl group, a phenylmethyl group, a cresyl group (isomers), a phenylethyl group, a furfuryl group, and a pyrazyl group.

A monomer structure having an (R—O—)$_4$Ti structure, as well as the above-described various polytitanoxanes having the R—O—Ti linkage can be preferably used as the organic oxytitanium composition having the R—O—Ti linkage used in the present embodiment. It is extremely difficult to isolate the polytitanoxane for determining the structure. Therefore, in the present embodiment, a composition containing at least one or more types of polytitanoxane having the R—O—Ti linkage is intended for the polytitanoxane composition having the R—O—Ti linkage.

The polytitanoxane composition having the R—O—Ti linkage used in the present embodiment is a composition such that the mole average degree of polymerization is 1.1 or more and 12 or less. The mole average degree of polymerization is determined by the following mathematical expression (1), using the number of Ti atoms contained in an individual polytitanoxane having an R—O—Ti linkage, which constitutes the polytitanoxane composition having the R—O—Ti linkage, and the following "molar ratio".

The polytitanoxane composition comprises one or more polytitanoxanes having a different degree of polymerization (the number of Ti atoms in the molecule).

The above "molar ratio" refers to the moles of a polytitanoxane having an individual degree of polymerization relative to the total moles of polytitanoxanes in the polytitanoxane composition.

By the above "mole average degree of polymerization," it is meant that the product of the molar ratio of a polytitanoxane having an individual degree of polymerization and the degree of polymerization is determined, and the product is integrated for all degrees of polymerization to obtain an integrated value. In other words, the question of how many Ti atoms are contained in one polytitanoxane molecule is answered as average value.

[Expression 1]

$$Pn = \sum_{1}^{z} (p_w \cdot m_w) \quad (1)$$

In the above mathematical expression (1), Pn is a positive number representing the mole average degree of polymerization.

z represents the number of types of polytitanoxane having an R—O—Ti linkage having a different degree of polymerization contained in the polytitanoxane composition having the R—O—Ti linkage, and represents an integer of 1 or more.

$p_w$ is a positive natural number representing the number of Ti atoms contained in a polytitanoxane molecular structure w having an R—O—Ti linkage contained in the polytitanoxane composition having the R—O—Ti linkage.

$m_w$ is the mole fraction of the molecular structure w to the composition and satisfies the following mathematical expression (2). The total of mole fractions is 1 (the left side).

[Expression 2]

$$1 = \sum_{1}^{z} m_w \quad (2)$$

In the above mathematical expression (2), z has the same meaning as z described in the above mathematical expression (1), and represents the number of types of polytitanoxane having an R—O—Ti linkage having a different degree of polymerization contained in the polytitanoxane composition having the R—O—Ti linkage, and represents an integer of 1 or more.

For example, when the polytitanoxane composition having the R—O—Ti linkage used in the present embodiment is a composition comprising 1 mole of a tetraalkoxytitanium represented by the following formula (9), and 1 mole of a polytitanoxane represented by the following formula (10), the mole average degree of polymerization is 1.5.

[Formula 5]

(9)

(10)

When the aryloxytitanium composition obtained by the production method in the present embodiment is used as a catalyst for a production of a diaryl carbonate, a polytitanoxane having an R—O—Ti linkage comprising small molecules as little as possible and having a high mole average degree of polymerization is preferred. When flowability is considered, the degree of polymerization is preferably not very high.

Therefore, the above mole average degree of polymerization is preferably in the range of 1.1 or more and 12 or less, most preferably 2 or more and 8 or less.

As the mole average degree of polymerization increases, the structure is more varied as previously described.

The polytitanoxane constituting the polytitanoxane composition that can be used in the present embodiment is preferably a polytitanoxane having an R—O—Ti linkage represented by the following formula (11).

[Formula 6]

(11)

In the formula (11), a represents a positive integer of 2 or more, c is an integer of 0 or more, d is an integer of 1 or more, and b is an integer of 1 or more, and a, b, c, and d satisfy 4a=2b+c+d and 2a+2=c+d.

The polytitanoxane constituting the polytitanoxane composition that can be used in the present embodiment is more preferably a polytitanoxane having an R—O—Ti linkage represented by the following formula (12).

[Formula 7]

$$Ti_eO_f(OR)_g \qquad (12)$$

In the formula (12), e represents a positive integer of 2 or more, g is an integer of 1 or more, and f is an integer of 1 or more, and e, f, and g satisfy 4e=2f+g and 2e+2=g.

When a, b, c, d, e, f, and g shown in the above formula (11) and formula (12) are to be determined, molecular weight may be required.

The molecular weight may be determined by a known method. Examples of the known method include a method by GPC, using a mass spectrometer (for example, a method described in RAPID COMMUNICATIONS IN MASS SPECTROMETRY, 14, 662-668 (2000)).

Particularly, when the hydrolyzability of the polytitanoxane composition having the R—O—Ti linkage is high, it is possible to use a divalent chelating agent to substitute the R—O—Ti linkage by the chelating agent to decrease the hydrolyzability (for the extent of the hydrolyzability of the organic titanium compound, RUST PREVENTION & CONTROL JAPAN, vol. 23, No. 7, 23-32 (1979) may be referred to), and measure and determine the molecular weight after the substitution by this divalent chelating agent.

Examples of preferred chelating agents include β-diketones, such as acetylacetone, and 1,2-dihydroxy aromatic compounds, such as catechol.

The value of a or e can be obtained by calculation after adding the above chelating agent in an excessive amount (for example, 1.1 moles or more, preferably in the range of 2 to 10 moles) per mole of Ti atoms contained in a compound (or composition) having an R—O—Ti linkage, removing (preferably evaporating by distillation) ROH produced as by-product, as required, and obtaining the molecular weight of the obtained compound (or composition) by the above-described method.

When the value of a or e can be obtained, the value of b, c, d, f, and g can be obtained from elementary analysis values, NMR, or the like.

The product obtained by adding the divalent chelating agent has a structure comprising equal moles of the chelating agent with respect to the molar amount of Ti atoms contained in the compound (or composition), in which, instead, 2-fold moles of RO groups with respect to this molar amount of Ti atoms are eliminated. (In the case of a=1, the chelating agent is usually 2-fold molar equivalents with respect to Ti atoms, and 4-fold molar equivalents of RO groups are eliminated.)

As described above, the polytitanoxane composition having the R—O—Ti linkage that can be used in the present embodiment is theoretically a particular polytitanoxane composition having an R—O—Ti linkage obtained from the mole average degree of polymerization represented by the above mathematical expression (1).

However, as described above, actual identification of the structure of an individual polytitanoxane is extremely difficult by the current analysis method.

Therefore, the polytitanoxane composition having the R—O—Ti linkage used in the present embodiment is preferably a particular polytitanoxane composition having the R—O—Ti linkage represented by the above formula (11) and/or the above formula (12).

Therefore, the mole average degree of polymerization defined in the above mathematical expression (1) may be obtained as follows.

By analyzing the polytitanoxane composition having the R—O—Ti linkage used in the present embodiment, as it is, the average composition of polytitanoxanes having the R—O—Ti linkage constituting the composition comprising the above general formula (11) is represented by the following formula (13).

[Formula 8]

$$Ti_hO_i(OH)_j(OR)_k \qquad (13)$$

In the formula (13), R represents the above-described group, h represents a positive number of 1 or more, j is a positive number of 0 or more, k is a positive number of 1 or more, and i is a positive number of more than 0, and h, i, j, and k satisfy 4h=2j+i+k and 2h+2=j+k.

Similarly, the average composition of polytitanoxanes having the R—O—Ti linkage constituting the polytitanoxane composition having the R—O—Ti linkage represented by the above general formula (12) is represented by the following formula (14).

[Formula 9]

$$Ti_pO_q(OR)_r \qquad (14)$$

In the above formula (14), R represents the above-described group, p represents a positive number of 1 or more, r is a positive number of 1 or more, and q is a positive number of 1 or more, and p, q, and r satisfy 4p=2q+r and 2p+2=r.

When h, i, j, k, p, q, and r shown in the above formulas (13) and (14) are to be determined, molecular weight may be required.

In such a situation, the molecular weight can be obtained by the method described when a, b, c, d, e, f, and g shown in the above formulas (11) and (12) are determined.

Therefore, as the mole average degree of polymerization, either h in the above general formula (13) or p in (14) may be used.

When it is difficult to detect c represented in the above formula (11) by analysis, e in the above formula (12) may be used as the value of the mole average degree of polymerization, assuming that the polytitanoxane composition having the R—O—Ti linkage is the structure represented by the above formula (12).

Of course, a monomer structure having an (R—O—)₄Ti structure may be contained in the polytitanoxane composition having the R—O—Ti linkage. Also in that case, as described above, h or p obtained by analyzing the polytitanoxane composition having the R—O—Ti linkage comprising the monomer structure having the (R—O—)₄Ti structure is the mole average degree of polymerization of the polytitanoxane composition having the R—O—Ti linkage.

As the above analysis method, known methods can be appropriately used.

Elementary analysis, atomic absorption spectroscopy, inductively coupled plasma-atomic emission spectroscopy, chromatography analysis, nuclear magnetic resonance (NMR), and the like which are routinely practiced can be preferably used, and they may be combined if necessary.

A particularly preferred method including, for example, determination of the content of carbon, oxygen, and hydrogen atoms by elementary analysis, the Ti content by inductively coupled plasma-atomic emission spectroscopy, and the contents of OH groups and (OR) groups by nuclear magnetic resonance, can provide the above h or p through calculation.

When it is difficult to obtain the content of (OR) groups, it may be obtained by a method of hydrolyzing the polytitanoxane composition having the R—O—Ti linkage to form ROH and then conducting chromatography analysis.

<Alkyloxytitanium Composition>

One example of the organic oxytitanium composition having the R—O—Ti linkage used in the present embodiment includes an alkyloxytitanium composition. Particularly, a polytitanoxane composition having an alkoxy group is preferred.

An alkyloxytitanium represents, among organic oxytitaniums constituting the above organic oxytitanium compositions having the R—O—Ti linkage, an organic oxytitanium in which the R group is an alkyl group, and the —O— forming the R—O—Ti linkage is oxygen bonded to the alkyl group.

Therefore, the alkyloxytitanium compositions are, among the above-described organic oxytitanium compositions having the R—O—Ti linkage, only those in which R is limited to an alkyl group, and thus excludes only part of the examples of the R group (examples in which R is not an alkyl group).

<Cycloalkyloxytitanium Composition>

One example of the organic oxytitanium composition having the R—O—Ti linkage used in the present embodiment includes a cycloalkyloxytitanium composition. Particularly, a polytitanoxane composition having a cycloalkoxy group is preferred.

A cycloalkyloxytitanium represents, among organic oxytitaniums constituting the above organic oxytitanium compositions having the R—O—Ti linkage, an organic oxytitanium in which the R group is a cycloalkyl group, and the —O— forming the R—O—Ti linkage is oxygen bonded to the cycloalkyl group.

Therefore, the cycloalkyloxytitanium compositions are, among the above-described organic oxytitaniums having the R—O—Ti linkage, only those in which R is limited to a cycloalkyl group, and thus excludes only part of the examples of the R group (examples in which R is not a cycloalkyl group).

The organic oxytitanium compositions having the R—O—Ti linkage used in the present embodiment in which the R group is an alkyl group and in which the R group is a cycloalkyl group exhibit a similar behavior in the above step (1) and step (A), and therefore, the above-described cycloalkyloxytitanium composition will be described below as having the same meaning as the alkyloxytitanium composition. (To be exact, the alkyl group is branched and/or linear, and the cycloalkyl group is cyclic, but there is no difference in reactivity and the like, and therefore, they have the same meaning herein. Similarly, a group in which a cycloalkyl group and an alkyl group are bonded to each other has the same meaning.)

<Aryloxytitanium Composition>

The aryloxytitanium composition used as a raw material in the present embodiment represents, among the above organic oxytitanium compositions having the R—O—Ti linkage, an organic oxytitanium composition in which the R group is a group having an aromatic ring, and the —O-forming the R—O—Ti linkage is oxygen bonded to the group having an aromatic ring. Particularly, a polytitanoxane composition having an aryloxy group is preferred.

When the above group having the aromatic ring is represented as an Ar group (that is, a polytitanoxane having an aryloxy group is defined as a polytitanoxane having an Ar—O—Ti linkage), a polytitanoxane having an aryloxy group can be represented by the following formula according to the definition of the above polytitanoxane composition having the R—O—Ti linkage.

The structure of the polytitanoxane is diversified by the combination of the above formulas (1) to (4) (in the polytitanoxane having the aryloxy group, the R group in the above formulas (1) to (4) is an Ar group), that is, by the combination of the following formulas (15) to (18) here, as described for the above polytitanoxane having the R—O—Ti linkage. It is difficult to identify the structure by the current analysis method, and the structure is presumed to be a mixture of various structures.

[Formula 10]

(15)

(16)

(17)

(18)

In the above formulas (15) to (18), Ar is a group having an aromatic ring, the Ar group forms an Ar—O—Ti linkage, and the oxygen atom of the ArO group in the linkage is bonded to the aromatic ring in the Ar group.

The above aryloxy group constituting the aryloxytitanium is preferably represented by the following formula (ArO).

[Formula 11]

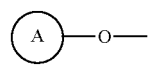

(ArO)

In the formula (ArO), the ring A represents an organic group having 6 to 20 carbon atoms, containing an aromatic group to which an oxygen atom bonded to Ti is bonded at any position keeping aromaticity, and may be a single ring or a plurality of rings, or a heterocyclic ring, and/or may be substituted by another substituent.

The ring A is often described as an Ar group herein.

The Ar group is not particularly limited as long as it is a group having an aromatic ring. Examples of the Ar group include groups composed of a carbon atom, a hydrogen atom, and/or an oxygen atom, such as an aromatic group and a group in which an aliphatic group and an aromatic group are bonded to each other. More specific examples include groups having an aromatic ring, which are an acyclic hydrocarbon group, a cyclic hydrocarbon group (a group such as, for example, a monocyclic hydrocarbon group, a condensed polycyclic hydrocarbon group, a bridged cyclic hydrocarbon group, a spiro hydrocarbon group, a ring assembly hydrocarbon group, a cyclic hydrocarbon group with a side chain, a heterocyclic group, a heterocyclic spiro group, or a bridged heterocyclic group), a group in which one or more groups selected from the above acyclic hydrocarbon group and the above cyclic hydrocarbon group are bonded, and a group in which the above groups are linked via covalent bonds to a particular nonmetal atom (carbon or oxygen).

The above covalent bond to the particular nonmetal atom (carbon or oxygen) is, for example, a state in which a group represented by the following formulas (5) to (8) and the above-described group are covalently bonded to each other.

[Formula 12]

(5)

(6)

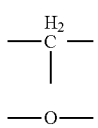

(7)

(8)

Among such Ar groups, the Ar group that can be preferably used in the present embodiment is selected from an aromatic group and a group in which an aliphatic group and an aromatic group are bonded to each other, considering that a side reaction is less likely to occur. Examples of the Ar group that can be preferably used in the present embodiment include a group selected from the group consisting of an acyclic hydrocarbon group and a cyclic hydrocarbon group (a monocyclic hydrocarbon group, a condensed polycyclic hydrocarbon group, a bridged cyclic hydrocarbon group, a spiro hydrocarbon group, a ring assembly hydrocarbon group, and a cyclic hydrocarbon group with a side chain), and a group in which at least one group selected from the group of these groups is bonded (groups substituted by each other), which are organic groups having 6 to 20 carbon atoms, preferably groups having 6 to 10 carbon atoms.

A more preferred Ar group is a group having an aromatic ring, which is a group selected from a group in which at least one or more selected from the group consisting of a cycloalkyl group and an aryl group are bonded to each other, and a group in which at least one or more selected from the group consisting of an alkyl group, a cycloalkyl group, and an aryl group are formed via a linkage selected from the above-described (5) to (8).

A group having 6 or 7 carbon atoms is further preferred.

Examples of such Ar groups include a phenyl group, a cresyl group (isomers), a xylyl group (isomers), and a naphthyl group.

Examples of preferred Ar groups are a phenyl group and a cresyl group (isomers).

The diaryl carbonate will be described later. When the aryloxytitanium composition produced by the production method in the present embodiment is used as a catalyst for a production of a diaryl carbonate, it is preferred that the aryl group constituting the diaryl carbonate, and the above-described aryl group constituting the aryloxytitanium are the same type of aryl group (that is, the aryloxy group constituting the aryloxytitanium is the same aryloxy group as the aryloxy group constituting the diaryl carbonate).

A monomer structure having an $(Ar-O-)_4Ti$ structure, as well as the above polytitanoxane having the Ar—O—Ti linkage can be preferably used as the aryloxytitanium used in the present embodiment. As previously described, it is extremely difficult to isolate the polytitanoxane for determining the structure. The polytitanoxane having the Ar—O—Ti linkage used in the present embodiment is a polytitanoxane composition having an Ar—O—Ti linkage, containing at least one or more types of polytitanoxane having an Ar—O—Ti linkage.

The above polytitanoxane composition having the Ar—O—Ti linkage is a composition such that a mole average degree of polymerization is 1.1 or more and 12 or less. The mole average degree of polymerization is determined by the following mathematical expression (1), using the number of Ti atoms contained in an individual polytitanoxane having an Ar—O—Ti linkage, which constitutes the polytitanoxane composition, and the following "molar ratio".

The polytitanoxane composition comprises one or more polytitanoxanes having a different degree of polymerization (the number of Ti atoms in the molecule).

The above "molar ratio" refers to the moles of a polytitanoxane having an individual degree of polymerization relative to the total moles of polytitanoxanes in the polytitanoxane composition.

By the above "mole average degree of polymerization," it is meant that the product of the molar ratio of a polytitanoxane having an individual degree of polymerization and the degree of polymerization is determined, and the product is integrated for all degrees of polymerization to obtain an integrated value. In other words, the question of how many Ti atoms are contained in one polytitanoxane molecule is answered as average value.

[Expression 3]

$$Pn = \sum_{1}^{z} (p_w \cdot m_w) \quad (1)$$

In the above mathematical expression (1), Pn is a positive number representing the mole average degree of polymerization.

z represents the number of types of polytitanoxane having an Ar—O—Ti linkage having a different degree of polymerization contained in the polytitanoxane composition having the Ar—O—Ti linkage, and represents an integer of 1 or more.

$p_w$ is a positive natural number representing the number of Ti atoms contained in a polytitanoxane molecular structure w having an Ar—O—Ti linkage contained in the composition.

$m_w$ is the mole fraction of the above molecular structure w to the composition and satisfies the following mathematical expression (2).

The total of mole fractions is 1 (the left side).

[Expression 4]

$$1 = \sum_{1}^{z} m_w \quad (2)$$

In the above mathematical expression (2), z has the same meaning as z described in the above mathematical expression (1), and represents the number of types of polytitanoxane having an Ar—O—Ti linkage having a different degree of polymerization contained in the polytitanoxane composition having the Ar—O—Ti linkage, and represents an integer of 1 or more.

For example, in the case of a composition comprising 1 mole of a tetraaryloxytitanium represented by the following formula (19), and 1 mole of a polytitanoxane represented by the following formula (20), the mole average degree of polymerization is 1.5.

[Formula 13]

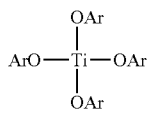

(19)

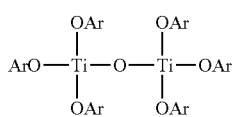

(20)

When the aryloxytitanium composition produced in the production method in the present embodiment is used as a catalyst for a production of a diaryl carbonate, a polytitanoxane having an Ar—O—Ti linkage comprising small molecules as little as possible and having a high mole average degree of polymerization is preferred. When flowability is considered, the degree of polymerization is preferably not very high.

Therefore, the above-described mole average degree of polymerization is preferably in the range of 1.1 or more and 12 or less, more preferably in the range of 2 or more and 8 or less.

As the mole average degree of polymerization increases, the structure is more varied as previously described.

The polytitanoxane having the Ar—O—Ti linkage used in the production method in the present embodiment can be represented by the following general formula (21).

[Formula 14]

  (21)

$Ti_aO_b(OH)_c(OAr)_d$

In the above formula (21), Ar represents the above-described group, a represents a positive integer of 2 or more, c is an integer of 0 or more, d is an integer of 1 or more, and b is an integer of 1 or more, and a, b, c, and d satisfy 4a=2b+c+d and 2a+2=c+d.

The polytitanoxane having the Ar—O—Ti linkage used in the production method in the present embodiment is more preferably a polytitanoxane having an Ar—O—Ti linkage represented by the following general formula (22).

[Formula 15]

$Ti_pO_q(OAr)_r$  (22)

In the above formula (22), Ar represents the above-described group, p represents a positive integer of 2 or more, r is an integer of 1 or more, and q is an integer of 1 or more, and 4p=2q+r is satisfied, and 2p+2=r.

When a, b, c, d, p, q, and r shown in the above formula (21) and formula (22) are to be determined, molecular weight may be required.

At the time, the molecular weight is obtained by a method similar to the method described when a, b, c, d, e, f, and g shown in the above formula (11) and formula (12) are determined.

As described above, the polytitanoxane composition having the Ar—O—Ti linkage used in the present embodiment is theoretically a particular polytitanoxane composition having an Ar—O—Ti linkage obtained from the mole average degree of polymerization represented by the above mathematical expression (1).

However, as previously described, actual identification of the structure of the polytitanoxane is extremely difficult by the current analysis method.

Therefore, the polytitanoxane composition having the Ar—O—Ti linkage used in the present embodiment is the particular polytitanoxane composition having the Ar—O—Ti linkage represented by the above formula (21) and/or the above formula (22).

Therefore, the above mole average degree of polymerization may be obtained as follows.

By analyzing the above polytitanoxane composition having the Ar—O—Ti linkage, as it is, the average composition of polytitanoxanes having the Ar—O—Ti linkage constituting the composition comprising the above formula (21) is represented by the following formula (23).

[Formula 16]

$Ti_hO_i(OH)_j(OAr)_k$  (23)

In the above formula (23), Ar represents the above-described group, h represents a positive number of 1 or more, j is a positive number of 0 or more, k is a positive number of 1 or more, and i is a positive number of more than 0, and h, i, j, and k satisfy 4h=2j+i+k and 2h+2=j+k.

Similarly, the average composition of polytitanoxanes having the Ar—O—Ti linkage constituting the composition comprising the above formula (22) is represented by the following formula (24).

[Formula 17]

$Ti_pO_q(OAr)_r$  (24)

In the above formula (24), Ar represents the above-described group, p represents a positive number of 1 or more, r is a positive number of 1 or more, and q is a positive number of 1 or more, and p, q, and r satisfy 4p=2q+r and 2p+2=r.

When h, i, j, k, p, q, and r shown in the above formula (21) and formula (22) are to be determined, molecular weight may be required.

At the time, the molecular weight can be obtained by the method described when a, b, c, d, e, f, and g shown in the above formula (11) and formula (12) are determined.

Therefore, as the mole average degree of polymerization, either h in the above formula (23) or p in the above formula (24) may be used.

When it is difficult to detect c represented in the above formula (21) by analysis, e in the above formula (22) may be used as the value of the mole average degree of polymerization, assuming that the composition is the structure represented by the formula (22).

Of course, as described above, a monomer structure having an (Ar—O—)$_4$Ti structure may be contained in the composition. Also in that case, as described above, h or p obtained by analyzing the composition comprising the monomer structure is the mole average degree of polymerization of the composition.

As the above-described analysis method, known methods can be appropriately used.

Elementary analysis, atomic absorption spectroscopy, inductively coupled plasma-atomic emission spectroscopy, chromatography analysis, and nuclear magnetic resonance (NMR), and the like which are routinely practiced can be preferably used, and they may be combined if necessary.

A preferred method among them including, for example, determination of the content of carbon, oxygen, and hydrogen atoms by elementary analysis, the Ti content by inductively coupled plasma-atomic emission spectroscopy, and the contents of OH groups and (OAr) groups by nuclear magnetic resonance, can provide the above-described h or p through calculation.

When it is difficult to obtain the content of (OAr) groups, it may be obtained by a method hydrolyzing the composition to form ArOH and then conducting chromatography analysis.

The polytitanoxane used in the production method in the present embodiment may be in the form of an adduct to or a mixture with ROH or ArOH, wherein R or Ar represents the above-described group.

(Diaryl Carbonate)

The diaryl carbonate used in the production method in the present embodiment is a diaryl carbonate represented by the following formula (25). The diaryl carbonate is also often described as an "aromatic carbonate" herein.

[Formula 18]

(25)

The aryloxy group constituting the above diaryl carbonate is represented by the following formula (ArO).

[Formula 19]

(ArO)

In the above formula (ArO), the ring A represents an organic group having 6 to 20 carbon atoms, containing an aromatic group to which an oxygen atom bonded to Ti is bonded at any position keeping aromaticity, and may be a single ring or a plurality of rings, or a heterocyclic ring, and/or may be substituted by another substituent.

The ring A is often described as an Ar group herein.

The preferred Ar group is not particularly limited as long as it is a group having an aromatic ring. Examples of the preferred Ar group include groups composed of a carbon atom, a hydrogen atom, and/or an oxygen atom, such as an aromatic group and a group in which an aliphatic group and an aromatic group are bonded to each other. More specific examples include groups having an aromatic ring, which are an acyclic hydrocarbon group, a cyclic hydrocarbon group (a group such as, for example, a monocyclic hydrocarbon group, a condensed polycyclic hydrocarbon group, a bridged cyclic hydrocarbon group, a spiro hydrocarbon group, a ring assembly hydrocarbon group, a cyclic hydrocarbon group with a side chain, a heterocyclic group, a heterocyclic spiro group, and a bridged heterocyclic group), a group in which one or more groups selected from the above acyclic hydrocarbon group and the above cyclic hydrocarbon group are bonded, and a group in which the above groups are linked via covalent bonds to a particular nonmetal atom (carbon or oxygen).

The above covalent bond to the particular nonmetal atom (carbon or oxygen) is, for example, a state in which a group represented by the following formulas (5) to (8) and the above-described group are covalently bonded to each other.

[Formula 20]

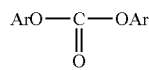
(5)

(6)

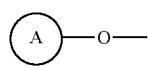
(7)

—O—
(8)

Among such Ar groups, one preferred as the Ar group constituting the diaryl carbonate used in the production method in the present embodiment is selected from an aromatic group and a group in which an aliphatic group and an aromatic group are bonded to each other, considering that a side reaction is less likely to occur. Examples thereof include a group selected from the group consisting of an acyclic hydrocarbon group and a cyclic hydrocarbon group (a monocyclic hydrocarbon group, a condensed polycyclic hydrocarbon group, a bridged cyclic hydrocarbon group, a spiro hydrocarbon group, a ring assembly hydrocarbon group, and a cyclic hydrocarbon group with a side chain), and a group in which at least one group selected from the group is bonded (groups substituted by each other), which are organic groups having 6 to 20 carbon atoms, preferably groups having 6 to 10 carbon atoms. A further preferred Ar group is a group having an aromatic ring, which is a group selected from a group in which at least one or more selected from the group consisting of an alkyl group, a cycloalkyl group, and an aryl group are bonded to each other, and a group in which at least one or more selected from the group consisting of an alkyl group, a cycloalkyl group, and an aryl group are formed via a linkage selected from the above-described (5) to (8).

Examples of such Ar groups include a phenyl group, a cresyl group (isomers), a xylyl group (isomers), and a naphthyl group.

Examples of preferred Ar groups are a phenyl group and a cresyl group (isomers), more preferably a group having 6 or 7 carbon atoms.

The diaryl carbonate used in the present embodiment is preferably diphenyl carbonate.

When the aryloxytitanium composition produced in the production method in the present embodiment is used as a catalyst for a production of a diaryl carbonate, it is preferred that the aryl group constituting the targeted diaryl carbonate, and the aryl group constituting the above aryloxytitanium are the same type of aryl group.

It is preferred that also for the diaryl carbonate as a raw material for obtaining the above aryloxytitanium composition, the aryl group constituting the above aryloxytitanium is the same type of aryl group, as in the diaryl carbonate to be produced.

Next, each step of the production method in the present embodiment will be described.

(Step 1)

The method for producing the aryloxytitanium composition in the present embodiment comprises the following step (1):

adding a diaryl carbonate to an organic oxytitanium composition having an R—O—Ti linkage, wherein R represents an organic group containing 1 to 20 carbon atoms, and evaporating a component having a lower boiling point than that of the diaryl carbonate, together with the above diaryl carbonate, so as to obtain an aryloxytitanium composition.

By carrying out the above step (1), the stability of the aryloxytitanium composition during transfer and/or storage is improved, and the quality of a diaryl carbonate produced when the aryloxytitanium composition is used as a catalyst composition for a production of a diaryl carbonate is improved.

A step of producing the targeted diaryl carbonate will be described later and is a complicated step with a plurality of reaction raw materials, reaction intermediates, and recycled substances. It is surprising that the above effect is achieved only by carrying out the above step (1), which is a discovery that cannot be expected from past findings regarding polytitanoxane compositions.

In the conventional art, the previous reaction of a catalyst with a high boiling component, and the like have been performed, but it is not clear what a component should be removed, and an improvement in the quality of the produced diaryl carbonate is not provided. The flowability of the catalyst mixed with the high boiling component, after storage, becomes significantly lower, and the catalyst cannot be used as a composition for storage, and it is only known that a catalyst composition is produced at a site adjacent to a diaryl carbonate production plant, or as one of steps connected by a line.

The aryloxytitanium composition obtained by the production method in the present embodiment has an excellent stability during transfer and/or storage, and also realizes a lower melting point. Therefore, its melting in use is easy, and its catalytic activity during transfer and/or storage can be less degraded.

Thus, the production of the above aryloxytitanium composition can be separated from the process for producing the diaryl carbonate, and these can be carried out without location limitation.

In other words, according to the production method in the present embodiment, a large amount of the composition for the catalyst can be inexpensively produced.

Therefore, the diaryl carbonate used in the above step (1) is preferably a diaryl carbonate having the same structure as a diaryl carbonate to be produced using the aryloxytitanium composition.

The combination of the organic oxytitanium composition having the R—O—Ti linkage and the diaryl carbonate used in the production method in the present embodiment will be described below.

(I) A case where the oxygen of the organic oxytitanium composition having the R—O—Ti linkage (of each compound when the composition is a composition of a plurality of compounds having an R—O—Ti linkage) is not bonded to an aromatic group (that is, a case where the oxygen forming the R—O—Ti linkage is bonded to an organic group other than an aromatic ring in the R group).

The diaryl carbonate or the organic oxytitanium composition having the R—O—Ti linkage is selected comparing the boiling point of hydroxy compounds corresponding to respective structures.

A diaryl carbonate is a carbonate ester of an aromatic hydroxy compound.

An ester is a dehydration condensation compound of a carboxylic acid and a hydroxy compound.

Therefore, a diaryl carbonate is also similarly considered, and it is natural in nomenclature to consider that a diaryl carbonate is a dehydration condensation compound of carbonic acid and an aromatic hydroxy compound. The aromatic hydroxy compound in considering so (or an aromatic hydroxy compound of a carbonic acid and an aromatic hydroxy compound produced by the hydrolysis of a diaryl carbonate, on the contrary) means the above-described corresponding hydroxy compound.

The other hydroxy compound corresponding to the structure of the organic oxytitanium having the R—O—Ti linkage represents a hydroxy compound having an ROH structure in which a hydrogen atom is added to an R—O—group.

In the production method in the present embodiment, a diaryl carbonate is added to an organic oxytitanium composition having an R—O—Ti linkage, and a component having a lower boiling point than that of the diaryl carbonate is evaporated, together with the diaryl carbonate.

In a case where the oxygen of the organic oxytitanium composition having the R—O—Ti linkage (each compound when the composition is a composition of a plurality of compounds having an R—O—Ti linkage) is not bonded to an aromatic group (that is, a case where the oxygen forming the R—O—Ti linkage is bonded to an organic group other than an aromatic ring in the R group), it is preferred that for the selection of a preferred R—O—group, when the boiling points of ROH and the aromatic hydroxy compound (that is, ArOH, and Ar has been described in the above section of diaryl carbonate) corresponding to respective structures described above are compared, the boiling point of ArOH is higher than that of ROH.

When the oxygen of the R—O— group is not bonded to an aromatic group, the above ROH is an alcohol.

Generally, the equilibrium of a diaryl carbonate and an alcohol is represented by the following formula (E2), and the equilibrium is biased to the left (an alkylaryl carbonate and an aromatic hydroxy compound).

Therefore, when a catalyst to which an alcohol component is bonded is used for a production of a diaryl carbonate, the alcohol component derived from the catalyst shifts the equilibrium in the unpreferred direction.

Therefore, it is preferred that the R—O— group in this case is removed out of the system in the step (1).

[Formula 21]

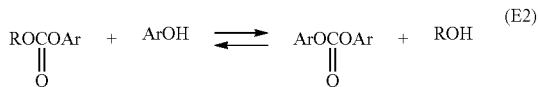

As described above, when ROH has a lower boiling point than that of ArOH, ROH can be removed out of the system, together with the diaryl carbonate, or together with the diaryl carbonate as an alkylaryl carbonate. When ROH has a lower boiling point than that of ArOH, the alkylaryl carbonate has a lower boiling point than that of the diaryl carbonate.

In this case, the R group is preferably a group having a small number of carbon atoms because of easy removal.

An R group having 1 to 6 carbon atoms is preferred. Considering the flowability of the polytitanoxane having the R—O— group, an alkyl group having 3 to 6 carbon atoms is more preferred, and a propyl group (isomers), a butyl group (isomers), a pentyl group (isomers), and a hexyl group (isomers) are further preferred.

On the other hand, for the diaryl carbonate, diphenyl carbonate and dicresyl carbonate (isomers) can be preferably used, considering the industrial utility value.

For the combination of the R group and the Ar group, a case where the R group is an R group selected from an n-propyl group, an isopropyl group, an n-butyl group, an isobutyl group, an n-pentyl group, and an isopentyl group, and the Ar group is a phenyl group is preferred.

Next, an amount of the organic oxytitanium composition having the R—O—Ti linkage and the diaryl carbonate used in the above step (1) will be described.

The amount of the diaryl carbonate used is 0.1 to 50 molar equivalents, preferably 1 to 20 molar equivalents, with respect to the total moles of Ti atoms contained in the organic oxytitanium composition having the R—O—Ti linkage.

It is possible to add the above amount at one time and then evaporate the component having the lower boiling point than that of the above diaryl carbonate, together with the diaryl carbonate. It is possible to add the above amount in portions and then evaporate the component having the lower boiling point than that of the diaryl carbonate, together with the diaryl carbonate. It is possible to add the above amount in portions and then evaporate the component having the lower boiling point than that of the diaryl carbonate, together with the diaryl carbonate, after each portion. It is possible to carry out the step in multiple batches, or continuously.

In order to efficiently evaporate the substance having the lower boiling point than that of the diaryl carbonate, it is preferred to repeat a plurality of times (two to four times) the operation of adding 1 to 3 molar equivalents of the diaryl carbonate and evaporating the component having the lower boiling point than that of the diaryl carbonate, together with the diaryl carbonate.

The method for adding the diaryl carbonate can be appropriately selected according to the type of the organic oxytitanium composition having the R—O—Ti linkage and the diaryl carbonate of interest, and the apparatus for carrying out the above step (1).

The diaryl carbonate may be added in a solid state or may be added in a liquid state (a melted or solution state).

The organic oxytitanium composition having the R—O—Ti linkage may also be solid or liquid (a melted or solution state).

It is preferred to carry out the step (1) in a uniform state. At the time, adding the liquid diaryl carbonate to the liquid organic oxytitanium composition having the R—O—Ti linkage is a preferred method.

A temperature in evaporating the component having the lower boiling point than that of the diaryl carbonate in the step (1) can be in the range of 30° C. to 300° C.

In order to increase the rate of evaporation, a higher temperature is preferred. On the other hand, at high temperature, an unpreferred reaction, for example, the rearrangement reaction of the diaryl carbonate, may occur to produce a complicated aryloxytitanium. At low temperature, it may be solid or poorly flowable. Therefore, the temperature is preferably in the range of 50° C. to 250° C., more preferably 80° C. to 250° C.

Depending on the compounds used, the melting point and the like vary, and therefore, the temperature can be adjusted in this range if necessary.

The step (1) is preferably carried out in a liquid state and is preferably carried out at a temperature at which the organic oxytitanium composition having the R—O—Ti linkage and the diaryl carbonate are in a substantially uniform liquid state.

In order to keep the reaction temperature constant, a known cooling apparatus and heating apparatus may be installed in the reactor for performing the step (1).

The reaction pressure varies depending on the type of the compounds used, the composition of the reaction system, the reaction temperature, the reaction apparatus, and the like, but is usually preferably in the range of 0.01 kPa to 100 kPa (absolute pressure). Considering the ease of industrial practice, the reaction pressure is preferably in the range of 0.1 kPa to 20 kPa (absolute pressure).

A time of period between addition of the diaryl carbonate and subsequent evaporation (residence time in the case of a continuous process) is not particularly limited, but usually 0.001 to 100 hours, preferably 0.01 to 80 hours, and more preferably 0.1 to 50 hours.

The step may be completed after sampling the reaction solution and confirming by a known analysis method that a desired amount of the aryloxytitanium composition is produced.

The step may also be completed after confirming that a desired amount of ROH is evaporated in the evaporated liquid.

When the organic oxytitanium composition having the R—O— group contains some chlorine (inorganic chlorine and/or hydrolyzable chlorine) as an impurity, it is preferred to continuously carry out the step until the chlorine concentration in the residual liquid drops to a desired level (for example, 100 ppm or less) because chlorine remaining in the aryloxytitanium composition is often unpreferred.

The analysis of the residual liquid may be difficult due to sampling and the like, and therefore, it is preferred to analyze the evaporated components to determine the completion of the step (1).

For example, it is preferred to further add the diaryl carbonate, until the Ti atom content in the diaryl carbonate evaporated is 100 ppm or less, preferably 10 ppm or less, and more preferably 1 ppm or less, and the chlorine content is 100 ppm or less, preferably 10 ppm or less, and more preferably 1 ppm or less, to evaporate a larger amount of components by distillation, or adjust the reflux amount to evaporate the diaryl carbonate containing a high concentration of the low boiling component.

(II) A case where the oxygen of the organic oxytitanium composition having the R—O—Ti linkage (of each compound when this composition is a composition of a plurality of compounds having an R—O—Ti linkage) is bonded to an aromatic group (that is, a case where the oxygen forming the R—O—Ti linkage is bonded to an aromatic ring in the R group)

In this case, the organic oxytitanium composition having the R—O—Ti linkage is an aryloxytitanium.

Therefore, the diaryl carbonate or the polytitanoxane having the R—O—Ti linkage may also be selected comparing the boiling point of hydroxy compounds corresponding to respective structures.

As described in the above (I), it is preferred to compare the corresponding ROH from the structure of the polytitanoxane having the R—O—Ti linkage, and ArOH corresponding to the structure of the diaryl carbonate used, for selection.

In this case, either of ROH and ArOH may have a lower boiling point, or they may have the same boiling point.

When the aryloxytitanium composition obtained in the above step (1) is used as a catalyst for a production of a diaryl carbonate, it is preferred to use a diaryl carbonate having the same structure as this targeted diaryl carbonate to be produced, in the step (1), and it is preferred that the boiling point of ROH is equal to or more than the boiling point of ArOH.

This is because the diaryl carbonate derived from the organic oxytitanium composition having the R—O—Ti linkage may be mixed in the aryloxytitanium composition.

An amount of the organic oxytitanium composition having the R—O—Ti linkage and the diaryl carbonate used in the above step (1) will be described.

The amount of the diaryl carbonate used is 0.1 to 50 molar equivalents, preferably 1 to 20 molar equivalents, with respect to the total moles of Ti atoms contained in the above organic oxytitanium composition having the R—O—Ti linkage.

It is possible to add the above amount at one time and then evaporate the component having the lower boiling point than that of the diaryl carbonate, together with the diaryl carbonate. It is possible to add the above amount in portions and then evaporate the component having the lower boiling point than that of the diaryl carbonate, together with the diaryl carbonate. It is possible to add the above amount in portions and then evaporate the component having the lower boiling point than that of the diaryl carbonate, together with the diaryl carbonate, after each portion. It is possible to carry out the step in multiple batches, or continuously.

In order to efficiently evaporate the substance having the lower boiling point than that of the diaryl carbonate, it is preferred to repeat a plurality of times, for example, two to four times the operation of adding 1 to 3 molar equivalents of the diaryl carbonate and evaporating the component having the lower boiling point than that of the diaryl carbonate, together with the diaryl carbonate.

The method for adding the diaryl carbonate can be appropriately selected according to the type of the organic oxytitanium composition having the R—O—Ti linkage and the diaryl carbonate of interest, and the apparatus for carrying out the above step (1).

The diaryl carbonate may be added in a solid state or may be added in a liquid state (a melted or solution state).

The organic oxytitanium composition having the R—O—Ti linkage may also be solid or liquid (a melted or solution state).

It is preferred to carry out the above step (1) in a uniform state. At the time, adding the liquid diaryl carbonate to the liquid organic oxytitanium composition having the R—O—Ti linkage is a preferred method.

A temperature in evaporating the component having the lower boiling point than that of the diaryl carbonate in the above step (1) can be selected in the range of 30° C. to 300° C.

In order to increase the rate of evaporation, a higher temperature is preferred. On the other hand, at high temperature, an unpreferred reaction, for example, the rearrangement reaction of the diaryl carbonate, may occur to produce a complicated aryloxytitanium. At low temperature, it may be solid or poorly flowable. Therefore, the temperature is preferably in the range of 50° C. to 250° C., more preferably 80° C. to 250° C.

Depending on the compounds used, the melting point and the like vary, and therefore, the temperature may be changed in this range if necessary.

The above step (1) is preferably carried out in a liquid state and is preferably carried out at a temperature at which the polytitanoxane having the R—O—Ti linkage and the diaryl carbonate are in a substantially uniform liquid state.

In order to keep the reaction temperature constant, a known cooling apparatus and heating apparatus may be installed in the reactor for performing the above step (1).

The reaction pressure varies depending on the type of the compounds used, the composition of the reaction system, the reaction temperature, the reaction apparatus, and the like, but is usually preferably in the range of 0.01 kPa to 100 kPa (absolute pressure). Considering the ease of industrial practice, the reaction pressure is preferably in the range of 0.1 kPa to 20 kPa (absolute pressure).

A time of period between addition of the diaryl carbonate and subsequent evaporation (residence time in the case of a continuous process) is not particularly limited, but usually 0.001 to 100 hours, preferably 0.01 to 80 hours, and more preferably 0.1 to 50 hours.

The step may be completed after sampling the reaction solution and confirming by a known analysis method that a desired amount of the aryloxytitanium composition is produced.

The step may also be completed after confirming that a desired amount of ROH is evaporated in the evaporated liquid.

When the organic oxytitanium composition having the R—O— group contains some chlorine (inorganic chlorine and/or hydrolyzable chlorine) as an impurity, it is preferred to continuously carry out the step until the chlorine concentration in the residual liquid drops to a desired level, for example, 100 ppm or less, because chlorine remaining in the aryloxytitanium composition is often unpreferred.

The analysis of the residual liquid may be difficult due to sampling and the like, and therefore, analysis of the evaporated components to determine the completion of the step (1) is a preferred method.

For example, it is preferred to further add the diaryl carbonate, until the Ti atom content in the diaryl carbonate evaporated is 100 ppm or less, preferably 10 ppm or less, and more preferably 1 ppm or less, and the chlorine content is 100 ppm or less, preferably 10 ppm or less, and more preferably 1 ppm or less, to evaporate a larger amount of components by distillation, or adjust the reflux amount to evaporate the diaryl carbonate containing a high concentration of the low boiling component.

It is not always necessary to use a reaction solvent in the above step (1). However, for the purposes of making the reaction operation easy, and the like, suitable solvents, for example, alkanes such as pentane (isomers), hexane (isomers), heptane (isomers), octane (isomers), nonane (isomers), and decane (isomers); aromatic hydrocarbons and alkyl-substituted aromatic hydrocarbons, such as benzene, toluene, xylene (isomers), ethylbenzene, diisopropylbenzene (isomers), dibutylbenzene (isomers), and naphthalene; nitrile compounds, such as acetonitrile and benzonitrile; aromatic compounds substituted by a halogen or a nitro group, such as chlorobenzene, dichlorobenzene (isomers), bromobenzene, dibromobenzene (isomers), chloronaphthalene, bromonaphthalene, nitrobenzene, and nitronaphthalene; polycyclic hydrocarbon compounds, such as diphenyl, substituted diphenyl, diphenylmethane, terphenyl, anthracene, and dibenzyltoluene (isomers); aliphatic hydrocarbons, such as cyclohexane, cyclopentane, cyclooctane, and ethylcyclohexane; ketones, such as methyl ethyl ketone and acetophenone; esters, such as dibutyl phthalate, dihexyl phthalate, dioctyl phthalate, and benzyl butyl phthalate; ethers and thioethers, such as tetrahydrofuran, 1,4-dioxane, 1,2-dimethoxyethane, diphenyl ether, and diphenyl sulfide; ketone compounds, such as acetone and methyl ethyl ketone; ester compounds, such as ethyl acetate and ethyl benzoate; and sulfoxides, such as dimethyl sulfoxide and diphenyl sulfoxide, can be preferably used as the reaction solvent.

ArOH corresponding to part of the diaryl carbonate structure is also preferably used as the reaction solvent.

In the step (1), an inert gas may also be used.

Oxygen is an unpreferred gas component because it has an oxidation action. It is preferred to replace oxygen, air, in the reactor (the apparatus for carrying out the step (1)) by an inert gas before the start of the step.

Further, when the diaryl carbonate is evaporated, it may be evaporated by being entrained in an inert gas.

As the inert gas, for example, nitrogen, helium, argon, a carbonic acid gas, methane, ethane, and propane can be used alone or in combination.

The organic oxytitanium composition having the R—O—Ti linkage is easily hydrolyzed by moisture, and therefore, it is preferred to control the moisture content in the system in the step (1).

It is preferred to control the moisture content at 0.1 mole or less per mole of Ti atoms in the system in the step (1).

A reactor for performing the step (1) is selected according to the above-described conditions.

Specifically, hitherto known reactors, such as an agitation tank, a pressure agitation tank, a reduced-pressure agitation tank, a column reactor, a distillation column, a packed column, and a film evaporator, can be used in combination, if necessary.

A type of a condenser provided in the reactor is not particularly limited, and a known condenser can be used.

For example, hitherto known condensers, such as a multi-tubular cylindrical condenser, a double-tube condenser, a single-tube condenser, and an air-cooled condenser, can be used in combination, if necessary.

The condenser may be provided inside the reactor, or may be provided outside the reactor and connected to the reactor through piping. Considering the types of the reactor and the condenser, the method for handling the condensate, and the like, various configurations are employed.

Materials for the reactor and the condenser are not particularly limited, and known materials can be used.

For example, glass, stainless steel, carbon steel, Hastelloy, a substrate subjected to glass lining, and a substrate coated with Teflon (registered trademark) can be used.

SUS304, SUS316, SUS316L, and the like are inexpensive and can be preferably used.

Instrumentation equipment, such as a flowmeter and a thermometer, and known process apparatuses, such as a reboiler, a pump, and a condenser, may be added as required. Known heating methods, such as by steam and a heater, can be applied. Known cooling methods, such as natural cooling, cooling water, and brine, can also be applied.

Certain steps may be added to the step (1), as required.

For example, a range of steps and apparatuses that those skilled in the art and the engineers can assume, such as the step of dissolving the diaryl carbonate, the step of dissolving the organic oxytitanium composition having the R—O—Ti linkage, the step of separating the alcohol, the step of separating and/or purifying the aromatic hydroxy compound, and the step of burning up or discarding by-products and the like, may be added.

The step (1) has been described above and will be more specifically described below.

A case where the R group of the organic oxytitanium having the R—O—Ti linkage is an alkyl group, that is, a case where the organic oxytitanium having the R—O—Ti linkage is an organic oxytitanium having an alkoxy group will be described in detail below.

In this case, the step (1) is carried out as a step comprising the following steps (A) and (B):

the step (A) of reacting an alkyloxytitanium with an aromatic hydroxy compound and evaporating an alcohol as by-product, by distillation, so as to obtain a crude aryloxytitanium composition; and the step (B) of adding a diaryl carbonate to the crude aryloxytitanium composition and evaporating a component having a lower boiling point than that of the diaryl carbonate, together with the diaryl carbonate, so as to obtain an aryloxytitanium composition.

The above step (A) is a step of exchanging an alkoxy group for an aromatic hydroxy group.

Before the step (A) is carried out, the boiling points of ROH corresponding to the alkoxy group and the aromatic hydroxy compound are compared, and the alkyloxytitanium and the aromatic hydroxy compound to be used are selected. They are selected as in the case of (I) described for the above-described step (1).

<Aromatic Hydroxy Compound>

The aromatic hydroxy compound used in the above step (A) will be described.

The aromatic hydroxy compound is an aromatic hydroxy compound represented by the following formula (26).

[Formula 22]

$$ArOH \tag{26}$$

In the formula (26), the Ar group is a ring A represented by the following formula (27).

[Formula 23]

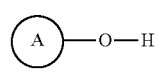

$$(27)$$

In the above formula (27), the ring A represents an organic group having 6 to 20 carbon atoms, comprising an aromatic group to which an oxygen atom forming an OH group is bonded at any position keeping aromaticity, and may be a single ring or a plurality of rings, or a heterocyclic ring, and/or may be substituted by another substituent.

The Ar group is not particularly limited as long as it is a group having an aromatic ring. Examples of the Ar group include groups composed of a carbon atom, a hydrogen atom, and/or an oxygen atom, such as an aromatic group and a group in which an aliphatic group and an aromatic group are bonded to each other. More specific examples include groups having an aromatic ring, which are a group comprising an acyclic hydrocarbon group or a cyclic hydrocarbon group (for example, a monocyclic hydrocarbon group, a condensed polycyclic hydrocarbon group, a bridged cyclic hydrocarbon group, a spiro hydrocarbon group, a ring assembly hydrocarbon group, a cyclic hydrocarbon group with a side chain, a heterocyclic group, a heterocyclic spiro group, and a bridged heterocyclic group), a group in which one or more groups selected from the above acyclic hydrocarbon group and the above cyclic hydrocarbon group are bonded, and a group in which the above groups are linked via covalent bonds to a particular nonmetal atom (carbon or oxygen).

The above covalent bond to the particular nonmetal atom (carbon or oxygen) is, for example, a state in which a group represented by the following formulas (5) to (8) and the above-described group are covalently bonded to each other.

[Formula 24]

$$-\overset{|}{\underset{|}{C}}- \quad (5)$$

$$-\overset{H}{\underset{|}{C}}- \quad (6)$$

$$-\overset{H_2}{C}- \quad (7)$$

$$-O- \quad (8)$$

Among such Ar groups, the Ar group that can be preferably used in the present embodiment is selected from an aromatic group and a group in which an aliphatic group and an aromatic group are bonded to each other, considering that a side reaction is less likely to occur. Examples of the Ar group that can be preferably used in the present embodiment include a group selected from the group consisting of an acyclic hydrocarbon group and a cyclic hydrocarbon group (a monocyclic hydrocarbon group, a condensed polycyclic hydrocarbon group, a bridged cyclic hydrocarbon group, a spiro hydrocarbon group, a ring assembly hydrocarbon group, and a cyclic hydrocarbon group with a side chain), and a group in which at least one group selected from the group is bonded (groups substituted by each other), which are organic groups having 6 to 20 carbon atoms, preferably groups having 6 to 10 carbon atoms. A further preferred Ar group is a group having an aromatic ring, which is a group selected from a group in which at least one or more selected from the group consisting of a cycloalkyl group and an aryl group are bonded to each other, and a group in which at least one or more selected from the group consisting of an alkyl group, a cycloalkyl group, and an aryl group are formed via a linkage selected from the above (5) to (8).

Examples of such Ar groups include a phenyl group, a cresyl group (isomers), a xylyl group (isomers), and a naphthyl group.

Examples of preferred Ar groups are a phenyl group and a cresyl group (isomers), more preferably a group having 6 or 7 carbon atoms.

When ROH has a lower boiling point than that of ArOH, ROH is easily removed by distillation, and therefore, an organic oxytitanium having an alkoxy group (R—O—group) and an aromatic hydroxy compound (ArOH) such that ROH has a lower boiling point than that of ArOH are selected.

In this case, the preferred R group is preferably a group having a small number of carbon atoms because of easy removal.

The R group preferably is a group having 1 to 6 carbon atoms, more preferably an alkyl group having 3 to 6 carbon atoms, considering the flowability of the organic oxytitanium having the R—O—group, and even more preferably a propyl group (isomers), a butyl group (isomers), a pentyl group (isomers), or a hexyl group (isomers).

For the aromatic hydroxy compound, phenols and cresol (isomers) can be preferably used, considering the industrial utility value.

The most preferred combination of the R group and the Ar group is a case where the R group is an R group selected from an n-propyl group, an isopropyl group, an n-butyl group, an isobutyl group, an n-pentyl group, and an isopentyl group, and the Ar group is a phenyl group.

Next, an amount of the alkyloxytitanium and the aromatic hydroxy compound used in the above step (A) will be described.

The amount of the aromatic hydroxy compound used is preferably 1 to 50 molar equivalents, more preferably 5 to 30 molar equivalents, with respect to the total moles of alkoxy groups contained in the alkyloxytitanium (alkyloxytitanium composition in the case of a composition) and is determined by the size of the reactor, and the like.

If a large amount of polyhydroxy compound (for example, catechol, trihydroxyphenol, and salicylic acid) is included in the aromatic hydroxy compound, this polyhydroxy compound reacts with the alkyloxytitanium, and the amount of the targeted aryloxytitanium produced decreases. Therefore, the content of the polyhydroxy compound in the above step (A) is preferably 0.01 or less, more preferably 0.001 or less, in terms of the molar ratio to titanium atoms.

It is possible to add the above amount at one time and then evaporate the alcohol derived from the alkyloxytitanium. It is possible to add the above amount in portions and then evaporate the alcohol derived from the alkyloxytitanium. It is possible to add the above amount in portions and then evaporate the alcohol derived from the alkyloxytitanium after each portion. It is possible to carry out the step in multiple batches, or continuously.

In order to efficiently evaporate the alcohol, the operation of adding 1 to 3 molar equivalents of the aromatic hydroxy compound and evaporating the alcohol may be performed a plurality of times, for example, two to four times.

Part or all of the excessive amount of the aromatic hydroxy compound may be evaporated, together with the alcohol.

The excessive amount has been described above. The aryloxytitanium is theoretically produced from equal moles of the aromatic hydroxy compound with respect to alkoxy groups contained in the alkyloxytitanium.

Therefore, a larger amount of the aromatic hydroxy compound than the moles of the above alkoxy groups is the excessive amount of the aromatic hydroxy compound.

The word "derived" is often used herein, and "derived" is used to mean that when a functional group of a raw feed compound changes in a reaction, the group of the raw material is inherited.

A method for adding the aromatic hydroxy compound can be appropriately selected according to the type of the alkyloxytitanium and the aromatic hydroxy compound of interest, and the apparatus for carrying out the above step (A).

The aromatic hydroxy compound may be added in a solid state or may be added in a liquid state (a melted or solution state).

The alkyloxytitanium may also be solid or liquid (a melted or solution state).

It is preferred to carry out the step (A) in a uniform state. At the time, adding the liquid aromatic hydroxy compound to the liquid alkyloxytitanium is a preferred method.

The step (A) can be carried out in the range of 30° C. to 300° C.

In order to increase the rate of evaporating the alcohol as by-product, high temperature is preferred, but the aromatic hydroxy compound may also be evaporated before all alkoxy groups are substituted. At low temperature, it may be solid or poorly flowable. Therefore, the temperature is preferably in the range of 50° C. to 250° C., more preferably 80° C. to 150° C.

Depending on the compounds used, the melting point and the like vary, and therefore, the temperature may be changed in this range if necessary.

The step (A) is preferably carried out in a liquid state and is preferably carried out at a temperature at which the alkyloxytitanium and the aromatic hydroxy compound are in a substantially uniform liquid state.

In order to keep the reaction temperature constant, a known cooling apparatus and heating apparatus may be installed in the reactor for performing the step (A).

The reaction pressure in the step (A) varies depending on the type of the compounds used, the composition of the reaction system, the reaction temperature, the reaction apparatus, and the like, but is usually preferably in the range of 1 kPa to 200 kPa (absolute pressure). Considering the ease of industrial practice, the reaction pressure is preferably in the range of 0.1 kPa to 120 kPa (absolute pressure).

A time of period between addition of the aromatic hydroxy compound and subsequent evaporation (residence time in the case of a continuous process) is not particularly limited, but usually 0.001 to 100 hours, preferably 0.01 to 80 hours, and more preferably 0.1 to 50 hours.

The step may be completed after sampling the reaction solution and confirming by a known analysis method that a desired amount of the aryloxytitanium is produced.

The step may also be completed after confirming that a desired amount of ROH is evaporated in the evaporated liquid.

When the organic oxytitanium having an R—O— group contains some chlorine (inorganic chlorine and/or hydrolyzable chlorine), it is preferred to continuously carry out the step until the chlorine concentration in the residual liquid drops to a desired level, for example, 100 ppm or less, because chlorine remaining in the aryloxytitanium is often unpreferred.

It is not always necessary to use a reaction solvent in the above step (A). However, for the purposes of making the reaction operation easy, and the like, suitable solvents, for example, alkanes such as pentane (isomers), hexane (isomers), heptane (isomers), octane (isomers), nonane (isomers), and decane (isomers); aromatic hydrocarbons and alkyl-substituted aromatic hydrocarbons, such as benzene, toluene, xylene (isomers), ethylbenzene, diisopropylbenzene (isomers), dibutylbenzene (isomers), and naphthalene; nitrile compounds, such as acetonitrile and benzonitrile; aromatic compounds substituted by a halogen or a nitro group, such as chlorobenzene, dichlorobenzene (isomers), bromobenzene, dibromobenzene (isomers), chloronaphthalene, bromonaphthalene, nitrobenzene, and nitronaphthalene; polycyclic hydrocarbon compounds, such as diphenyl, substituted diphenyl, diphenylmethane, terphenyl, anthracene, and dibenzyltoluene (isomers); aliphatic hydrocarbons, such as cyclohexane, cyclopentane, cyclooctane, and ethylcyclohexane; ketones, such as methyl ethyl ketone and acetophenone; esters, such as dibutyl phthalate, dihexyl phthalate, dioctyl phthalate, and benzyl butyl phthalate; ethers and thioethers, such as tetrahydrofuran, 1,4-dioxane, 1,2-dimethoxyethane, diphenyl ether, and diphenyl sulfide; ketone compounds, such as acetone and methyl ethyl ketone; ester compounds, such as ethyl acetate and ethyl benzoate; and sulfoxides, such as dimethyl sulfoxide and diphenyl sulfoxide, can be preferably used as the reaction solvent.

A diaryl carbonate (Ar—O—CO—O—Ar) having the same Ar group as the aromatic hydroxy compound is also preferably used as the reaction solvent.

In the step (A), an inert gas may also be used.

Oxygen is an unpreferred gas component because it has an oxidation action. It is preferred to replace oxygen, air, in the reactor (the apparatus for carrying out the step (A)) by an inert gas before the start of the step.

When the aromatic hydroxy compound is evaporated, it may be evaporated by being entrained in an inert gas.

As the inert gas, for example, nitrogen, helium, argon, a carbonic acid gas, methane, ethane, and propane can be used alone or in combination.

The aryloxytitanium is easily hydrolyzed by moisture, and therefore, it is preferred to control the moisture content in the system in the step (A).

Specifically, it is preferred to control the moisture content at 0.1 mole or less per mole of Ti atoms in the system in the step (A).

It is preferred that a reactor for performing the step (A) is also selected from those conforming to the above-described conditions.

Specifically, hitherto known reactors, such as an agitation tank, a pressure agitation tank, a reduced-pressure agitation tank, a column reactor, a distillation column, a packed column, and a film evaporator, can be used in combination, if necessary.

A type of a condenser provided in the reactor is not particularly limited, and a known condenser can be used.

For example, hitherto known condensers, such as a multitubular cylindrical condenser, a double-tube condenser, a single-tube condenser, and an air-cooled condenser, can be used in combination, if necessary.

The condenser may be provided inside the reactor, or may be provided outside the reactor and connected to the reactor through piping. Considering the types of the reactor and the condenser, the method for handling the condensate, and the like, various configurations are employed.

The materials for the reactor and the condenser are not particularly limited, and known materials can be used.

For example, glass, stainless steel, carbon steel, Hastelloy, a substrate subjected to glass lining, and a substrate coated with Teflon (registered trademark) can be used.

SUS304, SUS316, SUS316L, and the like are inexpensive and can be preferably used.

Instrumentation equipment, such as a flowmeter and a thermometer, and known process apparatuses, such as a reboiler, a pump, and a condenser, may be added as required. For heating, known methods, such as steam and a heater, may be used. Also for cooling, known methods, such as natural cooling, cooling water, and brine, can be used.

Certain steps may be added as required. For example, a range of steps and apparatuses that those skilled in the art and the engineers can assume, such as the step of dissolving the aromatic hydroxy compound, the step of dissolving the alkyloxytitanium, the step of separating the alcohol, the step of separating and/or purifying the aromatic hydroxy compound, and the step of burning up or discarding by-products and the like, can be added.

Next, the step (B) will be described.

In the step (B), the reaction solution in the above-described step (A) may be used as it is, or the step (B) may be carried out after adjustment of the concentration and the like. The step (B) may be carried out in the same apparatus, or may be carried out by transferring the reaction solution to another apparatus.

The step (B) is the step of adding a diaryl carbonate to the crude aryloxytitanium composition and evaporating a component having a lower boiling point than that of the above diaryl carbonate, together with the diaryl carbonate, so as to obtain an aryloxytitanium composition.

In the step (B), the organic oxytitanium composition having the R—O—Ti group used in the above-described step (1) is the crude aryloxytitanium composition obtained in the above-described step (A).

The diaryl carbonate used in the step (B) is preferably a diaryl carbonate having the same structure as a diaryl carbonate to be produced using the aryloxytitanium composition.

The boiling points of the aromatic hydroxy compound used in the step (A) and ArOH corresponding to the structure of the diaryl carbonate used (the diaryl carbonate is represented by Ar—O—CO—O—Ar, and in ArOH, a hydrogen atom is bonded to this ArO group) at ordinary pressure are compared for selection.

In this case, either the aromatic hydroxy compound or the above ArOH may have a lower boiling point, or they may have the same boiling point.

When the aryloxytitanium composition obtained in the step (B) is used as a catalyst for a production of a diaryl carbonate, it is preferred to use a diaryl carbonate having the same structure as a diaryl carbonate to be produced, in the step (B), and it is preferred that the boiling point of the aromatic hydroxy compound is equal to or more than the boiling point of ArOH.

This is because the diaryl carbonate derived from the aryloxytitanium may be mixed in the aryloxytitanium composition.

Next, an amount of the crude aryloxytitanium composition and the diaryl carbonate used in the step (B) will be described.

The amount of the diaryl carbonate used is 0.1 to 50 molar equivalents, preferably in the range of 1 to 20 molar equivalents, with respect to the total moles of Ti atoms contained in the crude aryloxytitanium composition.

It is possible to add the above amount at one time and then evaporate the component having the lower boiling point than that of the diaryl carbonate, together with the diaryl carbonate. It is possible to add the above amount in portions and then evaporate the component having the lower boiling point than that of the diaryl carbonate, together with the diaryl carbonate. It is possible to add the above amount in portions and then evaporate the component having the lower boiling point than that of the diaryl carbonate, together with the diaryl carbonate, after each portion. It is possible to carry out the step in multiple batches, or continuously.

In order to efficiently evaporate the substance having the lower boiling point than that of the diaryl carbonate, it is preferred to perform the operation of adding 1 to 3 molar equivalents of the diaryl carbonate and evaporating the component having the lower boiling point than that of the diaryl carbonate, together with the diaryl carbonate, a plurality of times, for example, two to four times.

The method for adding the diaryl carbonate can be appropriately selected according to the type of the aryloxytitanium and the diaryl carbonate of interest, and the apparatus for carrying out the above step (B).

The diaryl carbonate may be added in a solid state or may be added in a liquid state (a melted or solution state).

The crude aryloxytitanium composition may also be solid or liquid (a melted or solution state).

It is preferred to carry out the step (B) in a uniform state. At the time, adding the liquid diaryl carbonate to the liquid crude aryloxytitanium composition is a preferred method.

A temperature of the step (B) can be in the range of 30° C. to 300° C.

In order to increase the rate of evaporation, a higher temperature is preferred. On the other hand, at high temperature, an unpreferred reaction (for example, the rearrangement reaction of the diaryl carbonate) may occur to produce a complicated aryloxytitanium. At low temperature, it may be solid or poorly flowable. Therefore, the temperature is more preferably in the range of 50° C. to 250° C., even more preferably 80° C. to 250° C.

Depending on the compounds used, the melting point and the like vary, and therefore, the temperature may be changed in this range if necessary.

The step (B) is preferably carried out in a liquid state and is preferably carried out at a temperature at which the crude aryloxytitanium composition and the diaryl carbonate are in a substantially uniform liquid state.

In order to keep the reaction temperature constant, a known cooling apparatus and heating apparatus may be installed in the reactor for performing the step (B).

The reaction pressure varies depending on the type of the compounds used, the composition of the reaction system, the reaction temperature, the reaction apparatus, and the like, but is usually preferably in the range of 0.01 kPa to 100 kPa (absolute pressure). Considering the ease of industrial practice, the reaction pressure is preferably in the range of 0.1 kPa to 20 kPa (absolute pressure).

A time of period between addition of the diaryl carbonate and subsequent evaporation (residence time in the case of a continuous process) is not particularly limited, but usually 0.001 to 100 hours, preferably 0.01 to 80 hours, and more preferably 0.1 to 50 hours.

When the reaction solution is sampled, and the aryloxytitanium contains some chlorine (inorganic chlorine and/or hydrolyzable chlorine), it is preferred to continuously carry out the step until the chlorine concentration in the residual liquid drops to a desired level (for example, 100 ppm or less) because chlorine remaining in the aryloxytitanium is often unpreferred.

The analysis of the residual liquid may be difficult due to sampling and the like, and therefore, analysis of the evaporated components to determine the completion of the step (B) is a preferred method.

For example, the diaryl carbonate is further added until the Ti atom content in the diaryl carbonate evaporated is 100 ppm or less, preferably 10 ppm or less, and more preferably 1 ppm or less, and the chlorine content is 100 ppm or less, preferably 10 ppm or less, and more preferably 1 ppm or less, to evaporate a larger amount of components by distillation, or the reflux amount is adjusted to evaporate the diaryl carbonate containing a high concentration of the low boiling component.

It is not always necessary to use a reaction solvent in the above step (B). However, for the purposes of making the reaction operation easy, and the like, suitable solvents, for example, alkanes such as pentane (isomers), hexane (isomers), heptane (isomers), octane (isomers), nonane (isomers), and decane (isomers); aromatic hydrocarbons and alkyl-substituted aromatic hydrocarbons, such as benzene, toluene, xylene (isomers), ethylbenzene, diisopropylbenzene (isomers), dibutylbenzene (isomers), and naphthalene; nitrile compounds, such as acetonitrile and benzonitrile; aromatic compounds substituted by a halogen or a nitro group, such as chlorobenzene, dichlorobenzene (isomers), bromobenzene, dibromobenzene (isomers), chloronaphthalene, bromonaphthalene, nitrobenzene, and nitronaphthalene; polycyclic hydrocarbon compounds, such as diphenyl, substituted diphenyl, diphenylmethane, terphenyl, anthracene, and dibenzyltoluene (isomers); aliphatic hydrocarbons, such as cyclohexane, cyclopentane, cyclooctane, and ethylcyclohexane; ketones, such as methyl ethyl ketone and acetophenone; esters, such as dibutyl phthalate, dihexyl phthalate, dioctyl phthalate, and benzyl butyl phthalate; ethers and thioethers, such as tetrahydrofuran, 1,4-dioxane, 1,2-dimethoxyethane, diphenyl ether, and diphenyl sulfide; ketone compounds, such as acetone and methyl ethyl ketone; ester compounds, such as ethyl acetate and ethyl benzoate; and sulfoxides, such as dimethyl sulfoxide and diphenyl sulfoxide, can be preferably used as the reaction solvent.

ArOH corresponding to part of the diaryl carbonate structure is also preferably used as the reaction solvent.

An inert gas may also be used.

Oxygen is an unpreferred gas component because it has an oxidation action. It is preferred to replace oxygen, air, in the reactor (the apparatus for carrying out the step (B)) by an inert gas before the start of the step.

When the diaryl carbonate is evaporated, it may be evaporate by being entrained in an inert gas. As the inert gas, for example, nitrogen, helium, argon, a carbonic acid gas, methane, ethane, and propane are used alone or in combination, and a method for introducing the inert gas is preferred.

The aryloxytitanium is easily hydrolyzed by moisture, and therefore, it is preferred to control the moisture content in the system in the step (B).

It is preferred to control the moisture content at 0.1 mole or less per mole of Ti atoms in the system in the step (B).

A reactor for performing the above step (B) is selected according to the above-described conditions.

Specifically, hitherto known reactors, such as an agitation tank, a pressure agitation tank, a reduced-pressure agitation tank, a column reactor, a distillation column, a packed column, and a film evaporator, can be used in combination, if necessary.

A type of a condenser provided in the reactor is not particularly limited, and a known condenser can be used.

For example, hitherto known condensers, such as a multi-tubular cylindrical condenser, a double-tube condenser, a single-tube condenser, and an air-cooled condenser, can be used in combination, if necessary.

The condenser may be provided inside the reactor, or may be provided outside the reactor and connected to the reactor through piping. Considering the types of the reactor and the condenser, the method for handling the condensate, and the like, various configurations are employed.

A materials for the reactor and the condenser are not particularly limited, and known materials can be used.

For example, glass, stainless steel, carbon steel, Hastelloy, a substrate subjected to glass lining, and a substrate coated with Teflon (registered trademark) can be used.

SUS304, SUS316, SUS316L, and the like are inexpensive and can be preferably used.

Instrumentation equipment, such as a flowmeter and a thermometer, and known process apparatuses, such as a reboiler, a pump, and a condenser, may be added as required. For heating, known methods, such as steam and a heater, may be used. Also for cooling, known methods, such as natural cooling, cooling water, and brine, can be used.

Steps may be added to the step (B), as required.

For example, a range of steps and apparatuses that those skilled in the art and the engineers can assume, such as the step of dissolving the diaryl carbonate, the step of dissolving the crude aryloxytitanium composition, the step of separating the diaryl carbonate, the step of separating and/or purifying the aromatic hydroxy compound, and the step of burning up or discarding by-products and the like, may be added.

In the method for producing the aryloxytitanium composition in the present embodiment, a step (C) described later can be additionally carried out after the above-described step (1) or step (B).

The step (C) is a step of adjusting a component ratio of the aryloxytitanium composition and the diaryl carbonate.

The step (C) will be described below.

In this step (C), in order to stably use the aryloxytitanium (or the aryloxytitanium composition) obtained in the above-described step (1) or step (B), the component ratio is adjusted.

A content of titanium atoms contained in the aryloxytitanium (or composition) is preferably adjusted to be in the range of 1% by mass or more and 15% by mass or less, more preferably in the range of 5% by mass or more and 10% by mass or less.

A total content of the aryloxytitanium and the diaryl carbonate is preferably adjusted to 50% by mass or more in the aryloxytitanium composition. The upper limit value of the total content is not particularly limited, but is, for example, 99.9% by mass or less. When the total content is in the above range, an aryloxytitanium composition preferred for storage and/or transfer is provided.

The above total content varies depending on the purpose, and the structure of the diaryl carbonate and the aryloxytitanium, but if the above total content is low, the container required for storage and/or transfer, and the like are large, and therefore, the above value is preferred.

Adjustment may be made only with the diaryl carbonate and the aryloxytitanium (or composition), which is a preferred method.

Adjustment may be made by adding another component (solvent).

For the purposes of making the adjustment of flowability easy, and the like, suitable solvents, for example, alkanes such as pentane (isomers), hexane (isomers), heptane (isomers), octane (isomers), nonane (isomers), and decane (isomers); aromatic hydrocarbons and alkyl-substituted aromatic hydrocarbons, such as benzene, toluene, xylene (isomers), ethylbenzene, diisopropylbenzene (isomers), dibutylbenzene (isomers), and naphthalene; nitrile compounds, such as acetonitrile and benzonitrile; aromatic compounds substituted by a halogen or a nitro group, such as chlorobenzene, dichlorobenzene (isomers), bromobenzene, dibromobenzene (isomers), chloronaphthalene, bromonaphthalene, nitrobenzene, and nitronaphthalene; polycyclic hydrocarbon compounds, such as diphenyl, substituted diphenyl, diphenylmethane, terphenyl, anthracene, and dibenzyltoluene (isomers); aliphatic hydrocarbons, such as cyclohexane, cyclopentane, cyclooctane, and ethylcyclohexane; ketones, such as methyl ethyl ketone and acetophenone; esters, such as dibutyl phthalate, dihexyl phthalate, dioctyl phthalate, and benzyl butyl phthalate; ethers and thioethers, such as tetrahydrofuran, 1,4-dioxane, 1,2-dimethoxyethane, diphenyl ether, and diphenyl sulfide; ketone compounds, such as acetone and methyl ethyl ketone; ester compounds, such as ethyl acetate and ethyl benzoate; and sulfoxides, such as dimethyl sulfoxide and diphenyl sulfoxide, can be preferably used as the reaction solvent.

ArOH corresponding to part of the diaryl carbonate structure is also preferably used as the reaction solvent.

When the aryloxytitanium composition obtained in the step (C) is used as a catalyst for a production of a diaryl carbonate, using, as a solvent, a compound used in the step of producing a diaryl carbonate is a preferred method.

Such a solvent is a compound used (produced as by-product in some cases) in the step of producing the diaryl carbonate, and alcohols, aromatic hydroxy compounds, dialkyl carbonates, alkylaryl carbonates, alkyl aryl ethers, diaryl ethers, high boiling point by-products, and the like are used.

An inert gas may also be used.

Oxygen is an unpreferred gas component because it has an oxidation action. It is preferred to replace oxygen, air, in the reactor (the apparatus for carrying out the step (C)) by an inert gas before the start of the step.

When the diaryl carbonate is evaporated, it may be evaporate by being entrained in an inert gas.

As the inert gas, for example, nitrogen, helium, argon, a carbonic acid gas, methane, ethane, and propane are used alone or in combination, and a method for introducing the inert gas is preferred.

The aryloxytitanium is easily hydrolyzed by moisture, and therefore, it is preferred to control the moisture content in the system in the step (C).

In this case, it is preferred to control the moisture content at 0.1 mole or less per mole of Ti atoms in the system in the step (C).

A reactor for performing the above step (C) is selected according to the above-described conditions.

Specifically, hitherto known reactors, such as an agitation tank, a pressure agitation tank, a reduced-pressure agitation tank, a column reactor, a distillation column, a packed column, and a film evaporator, can be used in combination, if necessary.

A type of a condenser provided in the reactor is not particularly limited, and a known condenser can be used.

For example, hitherto known condensers, such as a multitubular cylindrical condenser, a double-tube condenser, a single-tube condenser, and an air-cooled condenser, can be used in combination, if necessary.

The condenser may be provided inside the reactor, or may be provided outside the reactor and connected to the reactor through piping. Considering the types of the reactor and the condenser, the method for handling the condensate, and the like, various configurations are employed.

The materials for the reactor and the condenser are not particularly limited, and known materials can be used.

For example, glass, stainless steel, carbon steel, Hastelloy, a substrate subjected to glass lining, and a substrate coated with Teflon (registered trademark) can be used.

SUS304, SUS316, SUS316L, and the like are inexpensive and can be preferably used.

Instrumentation equipment, such as a flowmeter and a thermometer, and known process apparatuses, such as a reboiler, a pump, and a condenser, may be added as required. For heating, known methods, such as steam and a heater, may be used. Also for cooling, known methods, such as natural cooling, cooling water, and brine, can be used.

Other certain steps may be added to the step (C), as required.

For example, a range of steps and apparatuses that those skilled in the art and the engineers can assume, such as the step of dissolving the diaryl carbonate, the step of dissolving the aryloxytitanium, the step of separating the diaryl carbonate, the step of separating and/or purifying the aromatic hydroxy compound, and the step of burning up or discarding by-products and the like, may be added.

Next, a method for producing the alkyloxytitanium used in the above step (A) will be described.

The alkyloxytitanium can be produced by a known method.

The step (A) and further the step (B) may be carried out using a commercial alkyloxytitanium.

Examples of a preferred method for producing the alkyloxytitanium include a method comprising the following step (X) and step (Y), that is, a method for sequentially or simultaneously performing:

step (X) of adding water to a tetraalkoxytitanium to react the tetraalkoxytitanium with the water so as to obtain a partial hydrolysis reaction solution, and step (Y) of evaporating an alcohol as by-product, from the hydrolysis reaction solution.

<Tetraalkoxytitanium>

The tetraalkoxytitanium used in the above step (X) will be described.

The tetraalkoxytitanium is a tetravalent tetraalkoxytitanium represented by $Ti(OQ)_4$, wherein Q represents an alkyl group.

The tetraalkoxytitanium may be in a monomeric or associated form.

The preferred Q group is preferably a group having a small number of carbon atoms because of easy removal as an alcohol in the step (Y).

The Q group is preferably a group having 1 to 6 carbon atoms, more preferably an alkyl group having 2 to 6 carbon atoms, and particularly preferably an ethyl group, a propyl group (isomers), a butyl group (isomers), a pentyl group (isomers), or a hexyl group (isomers).

The above step (X) will be described.

When the above-described alkyloxytitanium, for example, a polytitanoxane having an alkoxy group having an average degree of polymerization of 2 or more, is produced in the step (X), the relationship between the tetraalkoxytitanium, the amount of water added, and the average degree of polymerization is a relationship shown by a partial hydrolysis reaction and a condensation reaction represented by the following formula (28) and/or formula (29).

A case where a polytitanoxane having an alkoxy group having an average degree of polymerization of less than 2 is produced will be described later.

The average degree of polymerization of the polytitanoxane having the alkoxy group obtained in the above step (X) can be obtained by the amount of water added and/or an amount of an alcohol liberated.

The polytitanoxane having the alkoxy group is preferably a polytitanoxane having an alkoxy group (or a polytitanoxane composition having an alkoxy group) having an average degree of polymerization obtained in such a manner.

In most cases, both the hydrolysis reaction and the condensation reaction proceed in the step (X), and the alkyloxytitanium composition can be obtained.

It is presumed that a hydroxy group as shown in the formula (28) remains partially, and a condensate as shown in the formula (29) is obtained in the step (Y).

These reactions are generally suggested when titanium oxide is produced by a sol-gel method.

The step (X) is often described herein as a hydrolysis-condensation step.

[Formula 25]

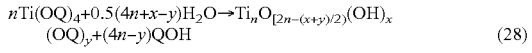

$$n\mathrm{Ti}(OQ)_4 + 0.5(4n+x-y)\mathrm{H}_2\mathrm{O} \rightarrow \mathrm{Ti}_n\mathrm{O}_{[2n-(x+y)/2]}(\mathrm{OH})_x(OQ)_y + (4n-y)Q\mathrm{OH} \quad (28)$$

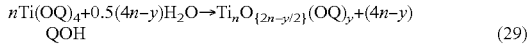

$$n\mathrm{Ti}(OQ)_4 + 0.5(4n-y)\mathrm{H}_2\mathrm{O} \rightarrow \mathrm{Ti}_n\mathrm{O}_{\{2n-y/2\}}(OQ)_y + (4n-y)Q\mathrm{OH} \quad (29)$$

In the formulas, Q is the above-described group, n represents an integer of 1 or more, x represents a number of 0 or more, and y represents a number of more than 0.

The average degree of polymerization roughly calculated from the above formula (29), and the amount of water added are brought together in the following Table 1.

In the case of the above formula (28), only the number of moles of the free alcohol changes, and the average degree of polymerization may be regarded as the same.

TABLE 1

Relationship between amount of water added and average degree of polymerization

| Average degree of polymerization (n) | Amount of water added (molar equivalents vs tetraalkoxytitanium) | Free alcohol (molar equivalents vs tetraalkoxytitanium) |
| --- | --- | --- |
| 2 | 0.500 | 2 |
| 2.2 | 0.545 | 2.4 |
| 3 | 0.667 | 4 |
| 4 | 0.750 | 6 |
| 5 | 0.800 | 8 |
| 6 | 0.833 | 10 |
| 7 | 0.857 | 12 |
| 8 | 0.875 | 14 |
| 9 | 0.889 | 16 |
| 10 | 0.900 | 18 |
| 11 | 0.909 | 20 |
| 12 | 0.917 | 22 |
| 13 | 0.923 | 24 |
| 14 | 0.929 | 26 |
| 15 | 0.933 | 28 |
| 16 | 0.938 | 30 |

The amount of water added in the step (X) is preferably 0.1 to 0.92 molar equivalents with respect to the tetraalkoxytitanium reacted because if the amount of water added increases, the flowability worsens significantly. In other words, the average degree of polymerization is preferably 12 or less.

A previously partially hydrolyzed and/or condensed alkoxytitanium, rather than the tetraalkoxytitanium, may be used for the starting material.

At the time, the amount of water is adjusted so that the average degree of polymerization is 12 or less.

The average degree of polymerization is more preferably 2 or more and 8 or less, considering flowability, stability, and use as a catalyst for a production of a diaryl carbonate.

It is presumed that when the average degree of polymerization is more than 1 and less than 2, partial hydrolysis occurs according to the following reaction formula (30). Assuming that the consumption of water is used for dimer production, and the remainder is a monomer, calculation should be performed.

A way of obtaining the average degree of polymerization at the time follows the above-described method, and thus, the amount of water added is adjusted.

[Formula 26]

$$2Ti(OQ)_4 + H_2O \rightarrow Ti_2O(OQ)_6 + 2QOH \quad (30)$$

Next, a method for adding water in the step (X) will be described.

As described above, the step (X) is the partial hydrolysis reaction of the tetraalkoxytitanium.

This hydrolysis reaction is widely known and can occur by a known method.

The average degree of polymerization should be in the above range. However, when the water added is not uniformly dispersed, a polytitanoxane having a significantly high degree of polymerization may be produced and solidified. Therefore, it is preferred to perform the hydrolysis reaction uniformly as much as possible to obtain a polytitanoxane having a narrow range of the degree of polymerization.

For such a method, it is preferred to dilute the tetraalkoxytitanium and/or the water added, with a solvent, and react them. More preferably, a method for diluting the tetraalkoxytitanium with a solvent, further also diluting water with the solvent, and then gradually adding the diluted water to the tetraalkoxytitanium solution is preferred.

The solvent should be a solvent inert to the tetraalkoxytitanium and water. A preferred solvent is an alcohol, more preferably the same type of alcohol as the alkoxy group of the tetraalkoxytitanium, that is, an alcohol having a structure in which hydrogen is added to the alkoxy group.

The concentration to be given by dilution can be appropriately determined by the tetraalkoxytitanium and the solvent used, and may be determined by the properties (flowability and the like) of the obtained alkyloxytitanium.

Preferably, the tetraalkoxytitanium is diluted so that it is 10 to 80% by mass.

If the concentration is low, the amount of the solvent evaporated increases. On the other hand, if the concentration is high, a significantly nonuniform composition may be generated as previously described. 50 to 80% by mass is more preferred.

The dilution of water may be appropriately determined by the solvent used and the addition method.

The preferred dilution concentration is 1 to 80% by mass, more preferably 3 to 50% by mass.

The purpose of the step (X) is to react the tetraalkoxytitanium with water, as described above, and addition and reaction may be performed by a known method.

Preferably, diluted water is gradually added to a diluted tetraalkoxytitanium solution, as described above.

A temperature of the step (X) can be in the range of −40° C. to 150° C. (or the boiling point or less of the solvent at ordinary pressure).

In order to increase the reaction rate, high temperature is preferred. On the other hand, at high temperature, an unpreferred reaction (for example, the production of a polytitanoxane having a significantly nonuniform degree of polymerization) may occur to produce a complicated polytitanoxane. At low temperature, it may be solid or poorly flowable. Therefore, the temperature is more preferably in the range of −20° C. to 100° C., even more preferably −10° C. to 100° C.

Depending on the compounds used, the melting point and the like vary, and therefore, the temperature may be changed in this range if necessary.

The step (X) is preferably carried out in a liquid state and is preferably carried out at a temperature at which the polytitanoxane produced is in a substantially uniform liquid state.

In order to keep the reaction temperature constant, a known cooling apparatus and heating apparatus may be installed in the reactor for performing the step (X).

The reaction pressure varies depending on the type of the compounds used, the composition of the reaction system, the reaction temperature, the reaction apparatus, and the like, but is usually preferably in the range of 0.01 kPa to 200 kPa (absolute pressure). Considering the ease of industrial practice, the reaction pressure is preferably in the range of 0.1 kPa to 150 kPa (absolute pressure).

A hydrolysis reaction time (residence time in the case of a continuous process) is not particularly limited and is usually 0.001 to 100 hours, preferably 0.01 to 80 hours, and more preferably 0.1 to 50 hours.

It is preferred to sample the reaction solution and continuously carry out the step until the liberated alcohol is in a desired range, and it is preferred to carry out the step while measuring the average degree of polymerization.

An inert gas may be used. Oxygen is an unpreferred gas component because it has an oxidation action. It is preferred to replace oxygen, air, in the reactor (the apparatus for carrying out the step (X)) by an inert gas before the start of the step.

As the inert gas, for example, nitrogen, helium, argon, a carbonic acid gas, methane, ethane, and propane are used alone or in combination, and a method for introducing the inert gas into the reactor is preferred.

A reactor for performing the above step (X) is selected according to the above-described conditions.

Specifically, hitherto known reactors, such as an agitation tank, a pressure agitation tank, a reduced-pressure agitation tank, a column reactor, a distillation column, a packed column, and a film evaporator, can be used in combination, if necessary.

A type of a condenser provided in the reactor is not particularly limited, and a known condenser can be used.

For example, hitherto known condensers, such as a multitubular cylindrical condenser, a double-tube condenser, a single-tube condenser, and an air-cooled condenser, can be used in combination, if necessary.

The condenser may be provided inside the reactor, or may be provided outside the reactor and connected to the reactor through piping. Considering the types of the reactor and the condenser, the method for handling the condensate, and the like, various configurations are employed.

A materials for the reactor and the condenser are not particularly limited, and known materials can be used.

For example, glass, stainless steel, carbon steel, Hastelloy, a substrate subjected to glass lining, and a substrate coated with Teflon (registered trademark) can be used.

SUS304, SUS316, SUS316L, and the like are inexpensive and can be preferably used.

Instrumentation equipment, such as a flowmeter and a thermometer, and known process apparatuses, such as a reboiler, a pump, and a condenser, may be added as required. For heating, known methods, such as steam and a heater, may be used. Also for cooling, known methods, such as natural cooling, cooling water, and brine, can be used.

Steps may be added as required.

For example, a range of steps and apparatuses that those skilled in the art and the engineers can assume, such as the step of dissolving the tetraalkoxytitanium, the step of dissolving water, the step of separating and/or purifying the alcohol, and the step of burning up or discarding by-products and the like, may be added.

Following the above-described step (X), the following step (Y) is performed.

The step (Y) is a step of evaporating an alcohol as by-product, from the hydrolysis reaction solution obtained in the above-described step (X).

As shown by the above formulas (28) to (30), when the tetraalkoxytitanium is hydrolyzed in the step (X), the alcohol derived therefrom is liberated. Although a structure as represented by the formula (28) is also partially produced, the structure of the formula (29) or (30) is mostly provided by carrying out the step (Y). The structure of the formula (28) may be partially included.

The step (Y) is often described herein as a concentration step.

When a solvent is used in the above step (X), it may be removed simultaneously with the alcohol in the step (Y) or separately.

To remove the alcohol, a known method can be used, but a method of distillation is preferred.

A temperature of the step (Y) can be in the range of $-40°$ C. to $250°$ C. (or the boiling point or less of the solvent at ordinary pressure).

In order to increase the rate of evaporation, high temperature is preferred. On the other hand, at high temperature, an unpreferred reaction (for example, the production of ethers) may occur to produce a complicated alkyloxytitanium. At low temperature, it may be solid or poorly flowable. Therefore, the temperature is more preferably in the range of $0°$ C. to $250°$ C., even more preferably $30°$ C. to $200°$ C.

Depending on the compounds used, the melting point and the like vary, and therefore, the temperature may be changed in this range if necessary.

The step (Y) is preferably carried out in a liquid state and is preferably carried out at a temperature at which the alkyloxytitanium produced is in a substantially uniform liquid state.

In order to keep the reaction temperature constant, a known cooling apparatus and heating apparatus may be installed in the reactor for performing the step (Y).

The reaction pressure varies depending on the type of the compounds used, the composition of the reaction system, the reaction temperature, the reaction apparatus, and the like, but is usually preferably in the range of 0.01 kPa to 200 kPa (absolute pressure). Considering the ease of industrial practice, the reaction pressure is preferably in the range of 0.01 kPa to 150 kPa (absolute pressure).

An evaporation time (residence time in the case of a continuous process) is not particularly limited and is usually 0.001 to 100 hours, preferably 0.01 to 80 hours, and more preferably 0.1 to 50 hours.

It is preferred to sample the evaporated liquid or the residual liquid and continuously carry out the step until the alcohol is in a desired range.

An inert gas may be used.

Oxygen is an unpreferred gas component because it has an oxidation action. It is preferred to replace oxygen, air, in the reactor (the apparatus for carrying out the step (Y)) by an inert gas before the start of the step.

As the inert gas, for example, nitrogen, helium, argon, a carbonic acid gas, methane, ethane, and propane are used alone or in combination, and a method for introducing the inert gas is preferred.

Also for a reactor for performing the above step (Y), one conforming to the conditions is selected.

Specifically, hitherto known reactors, such as an agitation tank, a pressure agitation tank, a reduced-pressure agitation tank, a column reactor, a distillation column, a packed column, and a film evaporator, can be used in combination, if necessary.

A type of a condenser provided in the reactor is not particularly limited, and a known condenser can be used.

For example, hitherto known condensers, such as a multitubular cylindrical condenser, a double-tube condenser, a single-tube condenser, and an air-cooled condenser, can be used in combination, if necessary.

The condenser may be provided inside the reactor, or may be provided outside the reactor and connected to the reactor through piping. Considering the types of the reactor and the condenser, the method for handling the condensate, and the like, various configurations are employed.

A materials for the reactor and the condenser are not particularly limited, and known materials can be used.

For example, glass, stainless steel, carbon steel, Hastelloy, a substrate subjected to glass lining, and a substrate coated with Teflon (registered trademark) can be used.

SUS304, SUS316, SUS316L, and the like are inexpensive and can be preferably used.

Instrumentation equipment, such as a flowmeter and a thermometer, and known process apparatuses, such as a reboiler, a pump, and a condenser, may be added as required. For heating, known methods, such as steam and a heater, may be used. Also for cooling, known methods, such as natural cooling, cooling water, and brine, can be used.

Certain steps may be added to the above step (Y), as required.

For example, a range of steps and apparatuses that those skilled in the art and the engineers can assume, such as the step of dissolving the tetraalkoxytitanium, the step of dissolving water, the step of separating and/or purifying the alcohol, and the step of burning up or discarding by-products and the like, may be added.

The aryloxytitanium composition is obtained by performing the above-described steps (A) and (B), and additionally the step (C), using the alkyloxytitanium composition obtained by performing the above-described steps (X) and (Y).

The above-described steps (1), (A), and (B) comprise the step of reacting the organic oxytitanium having the R—O—Ti linkage, the alkyloxytitanium, or the aryloxytitanium with the aromatic hydroxy compound or the diaryl carbonate, and evaporating the low boiling point compound. However, it is known to those skilled in the art that a reaction in which the Ti—O—Ti linkage is cut by the aromatic hydroxy compound or the diaryl carbonate generally does not occur, and it may be considered that the average degree of polymerization does not change.

<Component Having Lower Boiling Point than Diaryl Carbonate>

In the method for producing the aryloxytitanium composition in the present embodiment, it is extremely important to evaporate the component having the lower boiling point than that of the diaryl carbonate, together with the diaryl carbonate.

However, an identification of this component having a lower boiling point than that of the diaryl carbonate is difficult.

The low boiling component also includes an alcohol and the like, but the main point in the present embodiment is that the low boiling component is a component containing a Ti atom, having the lower boiling point than that of the diaryl carbonate.

If the aryloxytitanium composition containing the above component having the lower boiling point than that of the diaryl carbonate is used as a catalyst for a production of a diaryl carbonate, problems may occur, for example, the targeted diaryl carbonate is colored, and when the diaryl carbonate is used as a raw material for a melt process polycarbonate, the polymerization rate is slow, and the molecular weight does not reach a desired molecular weight.

In the present embodiment, the above-described problems can be surprisingly solved by evaporating the component having the lower boiling point than that of the diaryl carbonate.

The above component having the lower boiling point than that of the diaryl carbonate often comprises a halogen atom, in addition to a Ti atom. The above component having the lower boiling point than that of the diaryl carbonate is a compound comprising a Ti atom and/or a halogen atom, having the lower boiling point than that of the diaryl carbonate (the boiling point may be the boiling point at ordinary pressure but represents the boiling point at the pressure during evaporation).

[Aryloxytitanium Composition]

The aryloxytitanium composition in the present embodiment is an aryloxytitanium composition comprising an aryloxytitanium, and a diaryl carbonate, wherein a content of titanium atoms constituting the above aryloxytitanium is 1% by mass or more and 15% by mass or less.

The aryloxytitanium composition is also simply referred to as an "aryloxytitanium composition" below.

The components of the aryloxytitanium composition in the present embodiment will be described below.

(Aryloxytitanium)

An organic aryloxytitanium is preferably used as the aryloxytitanium constituting the aryloxytitanium composition in the present embodiment.

The aryloxytitanium constituting the aryloxytitanium composition in the present embodiment is preferably an aryloxytitanium having at least one Ti—O—Ar linkage (Ar represents an aromatic group and is specifically as described above).

The aryloxy group (Ar—O— group) is as described above.

When the aryloxytitanium composition in the present embodiment is used as a catalyst for a production of a diaryl carbonate described later, it is preferred that the aryl group constituting the diaryl carbonate, and the above aryl group are the same type of aryl group.

In other words, it is preferred that the aryloxy group is the same aryloxy group as the aryloxy group constituting the diaryl carbonate.

The aryloxytitanium composition in the present embodiment contains one or more aryloxytitaniums.

The aryloxytitanium composition in the present embodiment may comprise a plurality of types of aryloxytitanium. This is based on the fact that it is difficult to identify the exact structure of an aryloxytitanium.

The aryloxytitanium is an aryloxytitanium composed of a tetravalent Ti atom, and can be represented as $(ArO)_4Ti$ when one Ti atom is present in the compound.

The aryloxytitanium contained in the aryloxytitanium composition in the present embodiment is an aryloxytitanium having at least one Ar—O—Ti linkage and may be a polytitanoxane having an aryloxy group.

The above-described polytitanoxane having an Ar—O—Ti linkage can be preferably used as the aryloxytitanium contained in the aryloxytitanium composition in the present embodiment. As described above, it is extremely difficult to isolate the polytitanoxane for determining the structure. Therefore, the polytitanoxane having the Ar—O—Ti linkage herein is a polytitanoxane composition having an Ar—O—Ti linkage, containing at least one or more types of polytitanoxane having an Ar—O—Ti linkage.

A monomer structure having an $(Ar—O—)_4Ti$ structure may be contained in this composition.

The above polytitanoxane composition having the Ar—O—Ti linkage contained in the aryloxytitanium composition in the present embodiment is preferably a composition such that the mole average degree of polymerization is 1.1 or more and 12 or less. Here, the mole average degree of polymerization is determined as described above.

When the aryloxytitanium composition in the present embodiment is used as a catalyst for a production of a diaryl carbonate, the aryloxytitanium composition in the present embodiment preferably contains a polytitanoxane having an Ar—O—Ti linkage comprising small molecules as little as possible and having a high mole average degree of polymerization. When flowability is considered, the degree of polymerization is preferably not very high.

Therefore, the above-described mole average degree of polymerization is preferably in the range of 1.1 or more and 12 or less, more preferably 2 or more and 8 or less.

As the mole average degree of polymerization increases, the structure is more varied as previously described.

The aryloxytitanium constituting the aryloxytitanium composition in the present embodiment is preferably the polytitanoxane having the Ar—O—Ti linkage represented by the above formula (21).

The aryloxytitanium constituting the aryloxytitanium composition in the present embodiment is more preferably the polytitanoxane having the Ar—O—Ti linkage represented by the above formula (22).

As described above, the polytitanoxane having the Ar—O—Ti linkage that can be applied as the aryloxytitanium constituting the aryloxytitanium composition in the present embodiment is theoretically a particular polytitanoxane having an Ar—O—Ti linkage obtained from the mole average degree of polymerization represented by the above mathematical expression (1).

However, as described above, actual identification of the structure of an individual polytitanoxane is extremely difficult by the current analysis method.

Therefore, the polytitanoxane having the Ar—O—Ti linkage that can be applied as the aryloxytitanium contained in the aryloxytitanium composition in the present embodiment is preferably the particular polytitanoxane having the Ar—O—Ti linkage represented by the above formula (21) and/or the above formula (22).

The polytitanoxane having the Ar—O—Ti linkage contained in the aryloxytitanium composition in the present embodiment may be in the form of an adduct to or a mixture with ArOH, wherein Ar represents the above-described group.

(Diaryl Carbonate)

The diaryl carbonate contained in the aryloxytitanium composition in the present embodiment is shown in the above formula (25).

When the aryloxytitanium composition in the present embodiment is used as a catalyst for a production of a diaryl carbonate, it is preferred that the aryl group constituting the targeted diaryl carbonate, and the aryl group constituting the above-described aryloxytitanium are the same type of aryl group.

The above-described diaryl carbonate preferably has high purity.

Examples of impurities that can be contained in the diaryl carbonate include aromatic hydroxy compounds, water, alkylaryl carbonates, and dialkyl carbonates.

Their contents can be determined by checking the solubility of the targeted aryloxytitanium in the diaryl carbonate containing the above impurities, and the hydrolyzability of the aryloxytitanium.

On the other hand, examples of compounds unpreferred as impurities include aromatic polyhydroxy compounds, phenyl salicylate, and phenyl salicylate carbonate. A content of these compounds is preferably 0.5% by mass or less, more preferably 0.2% by mass or less.

The diaryl carbonate may also contain a Ti-containing compound having a lower boiling point than that of the diaryl carbonate. The Ti-containing compound can be removed during the step of evaporation together with the diaryl carbonate. That diaryl carbonate may also contain an aryloxytitanium. The aryloxytitanium is preferably the same type of aryloxytitanium as the aryloxytitanium.

(Method for Producing Aryloxytitanium)

A method for producing the aryloxytitanium contained in the aryloxytitanium composition in the present embodiment will be described.

To produce the aryloxytitanium, known methods can be used.

For example, a method for obtaining an aryloxytitanium by dehydrochlorinating titanium tetrachloride and an aromatic hydroxy compound, and a method for obtaining an aryloxytitanium by dealcoholizing an alkyloxytitanium and an aromatic hydroxy compound can be preferably used.

Among them, the method using an alkyloxytitanium can be preferably used.

<Method for Producing Aryloxytitanium from Alkyloxytitanium>

This method is a method for carrying out the following step (a) of reacting an alkyloxytitanium having an R—O—Ti linkage, wherein R is an alkyl group, with an aromatic hydroxy compound, to substitute an alkoxy group by an aryloxy group:

the step (a) of reacting an alkyloxytitanium with an aromatic hydroxy compound and evaporating an alcohol as by-product, by distillation, so as to obtain an aryloxytitanium.

When the above step (a) is carried out, the boiling points of ROH derived from the alkoxy group and the aromatic hydroxy compound are compared, and the alkyloxytitanium and the aromatic hydroxy compound used are selected.

A tetraalkoxytitanium, and a polytitanoxane having an alkoxy group can be used as the above alkyloxytitanium.

For the polytitanoxane having the alkoxy group, those in which the Ar group described for the above-described polytitanoxane having the aryloxy group is replaced by an R group can be preferably used.

The Ti atom of the alkyloxytitanium is a tetravalent Ti atom, and the Ti atom is bonded to four oxygen atoms.

The R group is preferably an alkyl group containing 1 to 6 carbon atoms, more preferably 2 to 6 carbon atoms. Still more preferred examples include an ethyl group, an isopropyl group, and an n-butyl group.

For the above aromatic hydroxy compound, an aromatic hydroxy compound having a structure in which a hydrogen atom is added to the above-described aryloxy group (that is, representing an ArOH structure) can be preferably used. More preferred examples are phenols and cresol (isomers).

As described above, the boiling points of ROH and the aromatic hydroxy compound (ArOH) are compared, and a combination in which ROH has a boiling point equal to or less than the boiling point of ArOH is selected.

The boiling point is the boiling point at the pressure in carrying out this step and is selected so that ROH produced as by-product can be evaporated by distillation.

The reaction conditions and the like of the step (a) are similar to those of the above-described step (A).

The aryloxytitanium contained in the aryloxytitanium composition in the present embodiment is preferably a polytitanoxane having an aryloxy group.

The polytitanoxane having the aryloxy group is preferably a polytitanoxane having an aryloxy group obtained by aryloxy substitution of a polytitanoxane having an alkoxy group in the above-described step (a).

Particularly, the reaction of the partially hydrolytic condensation of a tetraalkoxytitanium, including the above-described step (X) and step (Y), is easily controlled and provides an alkyloxytitanium having a stable quality.

The alkyloxytitanium used to obtain the aryloxytitanium is preferably the alkyloxytitanium obtained in the step comprising the above-described step (X) and step (Y).

The aryloxytitanium contained in the aryloxytitanium composition in the present embodiment is obtained by performing the above-described step (a), using the alkyloxytitanium obtained by performing the above-described step (X) and step (Y). When a polytitanoxane having an alkoxy group is used, an aryloxypolytitanoxane is obtained.

The step (a) comprises the step of reacting it with the aromatic hydroxy compound and evaporating the alcohol. However, it is known to those skilled in the art that cleavage of the Ti—O—Ti linkage by the aromatic hydroxy compound generally does not occur, and it may thus be considered that the average degree of polymerization does not change.

The aryloxytitanium composition in the present embodiment is suited for storage and/or transfer.

Generally, an aryloxytitanium has a very high melting point and is essentially difficult to transfer.

Usually, when a large amount of an aryloxytitanium is used, the aryloxytitanium can be transferred to a use destination (for example, a facility for producing a diaryl carbonate) which is adjacent to a plant using it through piping traced by a heat medium or the like. However, for example, transfer to a place where the installation of piping is difficult is difficult.

This is because the aryloxytitanium has a very high melting point, as described above, and high heat must be applied for a long time to melt the aryloxytitanium once solidified, and at the time, the aryloxytitanium may be degraded by heat.

In addition, the solidified aryloxytitanium is very hard, and an expensive facility is also necessary to pulverize the solidified aryloxytitanium to make heat conduction better.

Further, an aryloxytitanium composition containing a component having a lower boiling point than that of a diaryl carbonate is often more susceptible to thermal degradation, and the low boiling component may also adversely affect the container and the like used for transfer.

The aryloxytitanium composition in the present embodiment is intended to solve the problems during the storage and/or transfer of the aryloxytitanium when it is used on an industrial scale, and is suited as a composition for storage to be stored in a container (a container indicates a container for transporting the composition by land or by sea) having an internal volume of 200 L or more, and a composition for transfer to be transferred in a container (a container indicates a container for transporting the composition by land or by sea) having an internal volume of 200 L or more.

The aryloxytitanium composition in the present embodiment is a composition comprising at least one aryloxytitanium and further comprising a diaryl carbonate.

The at least one aryloxytitanium is selected from a tetraaryloxytitanium and a polytitanoxane having at least one Ar—O—Ti linkage.

As described above, the polytitanoxane constituting the above polytitanoxane composition preferred as the aryloxytitanium contained in the aryloxytitanium composition in the present embodiment is the polytitanoxane having the Ar—O—Ti linkage represented by the above formula (21).

The polytitanoxane constituting the above polytitanoxane composition preferred as the aryloxytitanium constituting the aryloxytitanium composition in the present embodiment is more preferably the polytitanoxane having the Ar—O—Ti linkage represented by the above general formula (22).

Substantially, the polytitanoxane having the Ar—O—Ti linkage that can be applied as one preferred in the aryloxytitanium constituting the aryloxytitanium composition in the present embodiment is presumed to be a plurality of polytitanoxane compositions having the Ar—O—Ti linkage represented by the above formula (21) and/or the above formula (22), as described above.

The aryloxytitanium in the aryloxytitanium composition in the present embodiment is preferably an aryloxypolytitanoxane. As described above, the aryloxypolytitanoxane is substantially an aryloxypolytitanoxane composition containing one or more types of aryloxytitanium having at least one Ti—O—Ti linkage in one molecule.

Preferably, the average degree of polymerization (h or p) is preferably 12 or less.

The average degree of polymerization is more preferably 2 or more and 8 or less, considering flowability, stability, and use as a catalyst for a production of a diaryl carbonate.

The aryloxytitanium composition in the present embodiment is a composition comprising the above described aryloxytitanium and diaryl carbonate, in which the content of titanium atoms in the composition is adjusted to be in the range of 1% by mass or more and 15% by mass or less, preferably in the range of 5% by mass or more and 10% by mass or less.

The aryloxytitanium composition in the present embodiment is a composition in which the content of the diaryl carbonate is adjusted preferably to 20% by mass or more, more preferably to 50% by mass or more, in the aryloxytitanium composition. The upper limit value of the content is not particularly limited, but is, for example, 95% by mass or less.

When the aryloxytitanium composition in the present embodiment is used as a composition for transfer, the content of the diaryl carbonate in the composition is preferably 20% by mass or more, more preferably 50% by mass or more, and even more preferably 50% by mass or more and 95% by mass or less, in terms of the ease of dissolution when the aryloxytitanium composition is solidified. If the content of the diaryl carbonate is low, high temperature is required on dissolving the composition, where an unpreferred reaction may occur (for example, Fries rearrangement), and the quality of the composition may degrade (for example, a decrease in catalytic activity). Therefore, the content of the diaryl carbonate is particularly preferably 60% by mass or more.

When the aryloxytitanium composition in the present embodiment is a composition for storage and/or transfer, a content of a compound having a salicylate ester structure in the aryloxytitanium composition in the present embodiment is preferably 1% by mass or less. The lower limit value of the content is not particularly limited, but is, for example, 0.02% by mass or more.

It is preferred that in the aryloxytitanium composition in the present embodiment, a content of the above diaryl carbonate is 50% by mass or more and 95% by mass or less, and a content of the compound having the boiling point of 150° C. or less is 1000 ppm or less. Such an aryloxytitanium composition can prevent the clogging of the storage tank, the piping, the pump, and the like during storage and transfer, can prevent a decrease in catalytic activity which occurs during long-term storage, and is preferred as a catalyst for a production of a diaryl carbonate.

Examples of the compound having the boiling point of 150° C. or less include alcohols, such as methanol, ethanol, propanol (isomers), butanol (isomers), and pentanol (isomers), water, and titanium tetrachloride. The above alcohols are, for example, impurities contained in the alkyloxytitanium, and those produced by the reaction of the alkyloxytitanium with the aromatic monohydroxy compound.

The content of the compound having the boiling point of 150° C. or less is more preferably 0.001 to 1000 ppm, even more preferably 0.1 to 500 ppm.

The aryloxytitanium composition as described above can be obtained, for example, by the above-described method for producing the aryloxytitanium composition.

The aryloxytitanium composition produced by the method for producing the aryloxytitanium composition, comprising the step (1) as described above, has the property that even if it is transferred and melted, thermal degradation, for example, discoloration, a decrease in catalytic activity as a catalyst for a production of a diaryl carbonate, and the like are less likely to occur, and degradation during storage, for example, discoloration, a decrease in catalytic activity as a catalyst for a production of a diaryl carbonate, and the like are also less likely to occur.

Further, an aryloxytitanium composition more suitable for storage and/or transfer is obtained by carrying out the above-described step (C) in addition to the step (1) or the steps (A) and (B).

Of course, it is preferred to use the alkyloxytitanium composition obtained in the step (X) and the step (Y), in carrying out the above-described step (1) or step (A).

The aryloxytitanium composition obtained by the above-described production method is preferably an aryloxytitanium composition represented by the following formulas (23) and/or (24).

[Formula 27]

$$Ti_hO_i(OH)_j(OAr)_k \quad (23)$$

In the above formula (23), ArO represents the group represented by the above-described formula (ArO), h represents a positive number of 1 or more, j is a positive number of 0 or more, k is a positive number of 1 or more, and i is a positive number of more than 0, and h, j, and k satisfy 4h=2j+i+k and 2h+2=j+k.

[Formula 28]

$$Ti_pO_q(OAr)_r \quad (24)$$

In the above formula (24), ArO represents the group represented by the above-described formula (ArO), p represents a positive number of 1 or more, r is a positive number of 1 or more, and q is a positive number of 1 or more, and p, q, and r satisfy 4p=2q+r and 2p+2=r.

The aryloxytitanium composition in the present embodiment is more preferably an aryloxytitanium composition comprising the aryloxytitanium composition produced by the above-described method for producing the aryloxytitanium composition, and a diaryl carbonate.

The form in transferring the aryloxytitanium composition in the present embodiment may be a solid form, a liquid form, or a slurry form.

Preferably, in terms of the ease of removal from the container after transfer, the form is any of a flake form, a pellet form, a powder form (that is, when the aryloxytitanium composition is solid, a state such that one lump is 100 g or less is preferred), and a liquid form.

The storage temperature is in the range of −40° C. to 200° C. At high temperature, an unpreferred reaction, for example, Fries rearrangement, may occur. Therefore, the storage temperature is preferably in the range of −40° C. to 180° C., more preferably in the range of −40° C. to 120° C.

The storage time is not limited and should be in the range of 0.01 hours to 60,000 hours.

If storage is continued over too long a period, an unpreferred reaction may occur. Therefore, the storage time is preferably 0.01 hours to 50,000 hours, more preferably in the range of 0.01 hours to 40,000 hours.

The transfer temperature is in the range of −40° C. to 200° C., though it also depends on the composition ratio of the aryloxytitanium composition, the structure of the aryloxytitanium, and the like. At high temperature, an unpreferred reaction, for example, Fries rearrangement, may occur. Therefore, the transfer temperature is preferably in the range of −40° C. to 180° C., more preferably in the range of −40° C. to 120° C.

The transfer time is not limited and may be in the range of 0.01 hours to 20,000 hours.

If transfer is over too long a period, an unpreferred reaction may occur gradually. Therefore, the transfer time is preferably 0.01 hours to 10,000 hours, more preferably in the range of 0.01 hours to 5,000 hours.

The state of the aryloxytitanium composition in transfer may be solid or liquid.

<Method for Adjusting Aryloxytitanium Composition>

The aryloxytitanium composition in the present embodiment is a composition containing an aryloxytitanium and a diaryl carbonate, as described above.

The content of each component may thus be adjusted by a known method.

As a preferred adjustment method, the following step (c) will be described:

the step (c) of adjusting the component ratio of the aryloxytitanium and the diaryl carbonate.

In order to stably use the aryloxytitanium, the component ratio is adjusted.

A content of titanium atoms contained in the aryloxytitanium is adjusted to be in the range of 1% by mass or more and 15% by mass or less, preferably in the range of 5% by mass or more and 10% by mass or less.

A content of the diaryl carbonate is preferably adjusted to 20% by mass or more, more preferably to 50% by mass or more, in the aryloxytitanium composition. The upper limit value of the content is not particularly limited, but is, for example, 95% by mass or less. The content may be adjusted only by the diaryl carbonate and the aryloxytitanium, which is a preferred method.

The content may be adjusted by adding another component (a solvent or the like).

The conditions and the like of the step (c) are similar to those of the above-described step (C).

[Method for Stabilizing Aryloxytitanium]

A method for stabilizing an aryloxytitanium in the present embodiment comprises a step of reacting an alkyloxytitanium composition with an aromatic hydroxy compound and evaporating an alcohol as by-product, by distillation, so as to obtain a crude aryloxytitanium composition (step (A)); and a step of adding a diaryl carbonate to the above crude aryloxytitanium composition and evaporating a component having a lower boiling point than that of the diaryl carbonate, together with the diaryl carbonate, so as to obtain an aryloxytitanium composition (step (B)), wherein an amount of the above diaryl carbonate used in the above step (B) is 0.1 to 50 molar equivalents with respect to total moles of Ti atoms contained in the above crude aryloxytitanium composition, and the temperature in evaporating the component having the lower boiling point than that of the diaryl carbonate in the above step (B) is in the range of 50° C. to 250° C.

In the method for stabilizing the aryloxytitanium in the present embodiment, in the aryloxytitanium composition obtained in the above step (B), a content of titanium atoms is 1% by mass or more and 15% by mass or less, and a content of the diaryl carbonate is preferably 20% by mass or more, more preferably 50% by mass or more and 95% by mass or less.

The amount of the above diaryl carbonate used in the above step (B) is preferably 0.1 to 50 molar equivalents, more preferably 1 to 20 molar equivalents, with respect to the total moles of Ti atoms contained in the above crude aryloxytitanium composition.

A temperature in evaporating the component having a lower boiling point than that of the diaryl carbonate in the above step (B) is preferably in the range of 50° C. to 250° C., more preferably in the range of 80 to 250° C.

In the aryloxytitanium composition obtained in the above step (B), it is preferred that the content of titanium atoms is 1% by mass or more and 15% by mass or less, and the content of the diaryl carbonate is 20% by mass or more, it is more preferred that the content of titanium atoms is 1% by mass or more and 15% by mass or less, and the content of the diaryl carbonate is 50% by mass or more and 95% by mass or less, and it is further preferred that the content of titanium atoms is 1% by mass or more and 15% by mass or less, and the content of the diaryl carbonate is 60% by mass or more and 95% by mass or less.

The steps (A) and (B) are as described above. The method for stabilizing the aryloxytitanium in the present embodiment may comprise the above-described step (C). Further, the above alkyloxytitanium composition may be the alkyloxytitanium composition obtained by sequentially or simultaneously performing the above step (X) and step (Y).

According to the above-described stabilization method, when the aryloxytitanium composition is stored or transferred, the clogging of the storage tank, the piping, the pump, and the like can be suppressed, and the activity of the aryloxytitanium composition as a catalyst is maintained for a long period.

<Method for Producing Diaryl Carbonate>

Next, a step of producing a diaryl carbonate, which is one application of the aryloxytitanium composition in the present embodiment, will be described.

A method for producing a diaryl carbonate in the present embodiment is a method for producing a diaryl carbonate, using the above-described aryloxytitanium composition as a catalyst, comprising performing transesterification and disproportionation reactions, using a dialkyl carbonate, an aromatic hydroxy compound, and the above aryloxytitanium composition, so as to produce a diaryl carbonate. By using the above-described aryloxytitanium composition as a catalyst, a diaryl carbonate can be efficiently produced.

The aryloxytitanium composition can be used without being limited to the following conditions.

First, compounds used will be described.

A diaryl carbonate is obtained by reactions including formulas (E1) to (E4) described later, using a dialkyl carbonate and an aromatic hydroxy compound as raw materials.

It is known that using a catalyst at the time is effective to improve productivity, and the aryloxytitanium composition in the present embodiment can be preferably used as the catalyst. It is more preferred to use the aryloxytitanium composition obtained by the production method in the present embodiment, as the catalyst. By using such a catalyst, the productivity of the diaryl carbonate can be improved.

(Aromatic Monohydroxy Compound)

The aromatic monohydroxy compound used in the method for producing the diaryl carbonate is represented by the following general formula (31).

[Formula 29]

$$Ar^1OH \qquad (31)$$

In the above formula (31), $Ar^1$ represents an aromatic group having 5 to 30 carbon atoms.

Examples of such an aromatic group include a phenyl group and various alkylphenyl groups, such as phenyl, tolyl (isomers), xylyl (isomers), trimethylphenyl (isomers), tetramethylphenyl (isomers), ethylphenyl (isomers), propylphenyl (isomers), butylphenyl (isomers), diethylphenyl (isomers), methylethylphenyl (isomers), pentylphenyl (isomers), hexylphenyl (isomers), and cyclohexylphenyl (isomers); various alkoxyphenyl groups, such as methoxyphenyl (isomers), ethoxyphenyl (isomers), and butoxyphenyl (isomers); various halogenated phenyl groups, such as fluorophenyl (isomers), chlorophenyl (isomers), bromophenyl (isomers), chloro(methyl)phenyl (isomers), and dichlorophenyl (isomers); and various substituted phenyl groups represented by the following general formula (32).

[Formula 30]

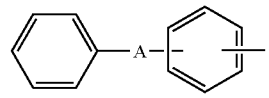

(32)

In the formula (32), A represents a single bond, a divalent group, such as —O—, —S—, —CO—, or —SO$_2$—, an alkylene group or a substituted alkylene group represented by the following (33), or a cycloalkylene group represented by the following (34).

The aromatic ring may be substituted by a substituent, such as a lower alkyl group, a lower alkoxy group, an ester group, a hydroxy group, a nitro group, a halogen, or a cyano group.

[Formula 31]

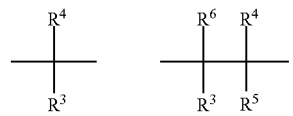

(33)

In the formula (33), $R^3$, $R^4$, $R^5$, and $R^6$ are each independently a hydrogen atom, a lower alkyl group, a cycloalkyl group, an aryl group, or an aralkyl group, and may be optionally substituted by a halogen atom or an alkoxy group.

[Formula 32]

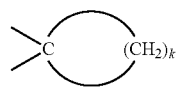

(34)

In the above formula (34), k is an integer of 3 to 11, and the hydrogen atom may be replaced by a lower alkyl group, an aryl group, a halogen atom, or the like.

Examples of the compound shown in the above formula (32) include a naphthyl group and various substituted naphthyl groups, such as naphthyl (isomers), methylnaphthyl (isomers), dimethylnaphthyl (isomers), chloronaphthyl (isomers), methoxynaphthyl (isomers), and cyanonaphthyl (isomers); and various substituted and unsubstituted hetero aromatic groups, such as pyridine (isomers), coumaryl (isomers), quinolyl (isomers), methylpyridyl (isomers), chloropyridyl (isomers), methylcoumaryl (isomers), and methylquinolyl (isomers).

Preferred examples include phenols and cresol. A preferred aromatic monohydroxy compound is an aromatic monohydroxy compound comprising the same type of aryl group as the aryl group constituting the aryloxytitanium composition.

(Dialkyl Carbonate)

The dialkyl carbonate (hereinafter also often described as an aliphatic carbonate) used in the step of producing the diaryl carbonate is represented by the following formula (35).

[Formula 33]

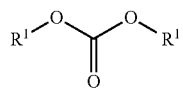
(35)

In the above formula (35), $R^1$ represents an alkyl group having 1 to 10 carbon atoms, an alicyclic group having 3 to 10 carbon atoms, or an aralkyl group having 6 to 10 carbon atoms.

Examples of such a dialkyl carbonate having $R^1$ include dimethyl carbonate, diethyl carbonate, dipropyl carbonate (isomers), dibutenyl carbonate (isomers), dibutyl carbonate (isomers), dipentyl carbonate (isomers), dihexyl carbonate (isomers), diheptyl carbonate (isomers), dioctyl carbonate (isomers), dinonyl carbonate (isomers), didecyl carbonate (isomers), dicyclopentyl carbonate, dicyclohexyl carbonate, dicycloheptyl carbonate, dibenzyl carbonate, diphenethyl carbonate (isomers), di(phenylpropyl) carbonate (isomers), di(phenylbutyl) carbonate (isomers), di(chlorobenzyl) carbonate (isomers), di(methoxybenzyl) carbonate (isomers), di(methoxymethyl) carbonate, di(methoxyethyl) carbonate (isomers), di(chloroethyl) carbonate (isomers), and di(cyanoethyl) carbonate (isomers).

Among these dialkyl carbonates, those in which $R^1$ is an alkyl group having 1 to 6 carbon atoms are preferred, and dimethyl carbonate, diethyl carbonate, dipropyl carbonate (isomers), dibutyl carbonate (isomers), dipentyl carbonate (isomers), and dihexyl carbonate (isomers) are more preferred.

(Alkylaryl Carbonate)

The alkylaryl carbonate is produced as an intermediate in the step of producing the diaryl carbonate.

The alkylaryl carbonate that is the intermediate is represented by the following general formula (36). The alkylaryl carbonate is also often described as an "aliphatic aromatic carbonate" herein.

[Formula 34]

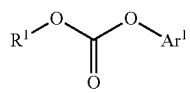
(36)

In the formula (36), $Ar^1$ represents an aromatic group having 5 to 30 carbon atoms. $R^1$ represents an alkyl group having 1 to 10 carbon atoms, an alicyclic group having 3 to 10 carbon atoms, or an aralkyl group having 6 to 10 carbon atoms.

An aliphatic alcohol as by-product is removed in a gas state, and aromatic carbonates produced are removed in a liquid state from the lower portion of the column.

Therefore, it is preferred to carry out the reactions, with a combination in which a boiling point of the aliphatic alcohol as by-product is lower than any of the respective boiling points of the aliphatic carbonate that is a starting material, the aromatic monohydroxy compound that is a reactant, and the aromatic carbonate that is a product.

An example of such a combination is a combination in which the aromatic monohydroxy compound is a phenol, and the $R^1$ of the aliphatic carbonate is a saturated aliphatic group having 4 to 6 carbon atoms.

When the boiling point of the alcohol as by-product decreases, the temperature difference between the top and the bottom of the distillation column increases, and thus, the reaction rate may be largely different between the stages of the distillation column. In order to obtain the aromatic carbonate in a higher yield, a combination in which the aromatic monohydroxy compound is a phenol, and the $R^1$ of the aliphatic carbonate is a saturated aliphatic group having 1 to 6 carbon atoms is more preferred.

The above-described production method is a method for producing an aromatic carbonate continuously produced, and therefore, a small amount of reaction products and the like may be fed together to a continuous multistage distillation column, together with the aliphatic carbonate and the aromatic monohydroxy compound.

Examples of such reaction products include the same type of alcohol as the alcohol as by-product, aliphatic aromatic carbonate, diaryl carbonate, ethers subjected to a decarboxylation reaction, and a Fries rearrangement product of the aromatic carbonate.

An amount of the aromatic monohydroxy compound that is a reactant in producing the diaryl carbonate can be in the range of 0.01 times or more and 1000 times or less an amount of the aliphatic carbonate that is a starting material, in a molar ratio.

The reaction of the aromatic monohydroxy compound with the aliphatic carbonate is mainly an equilibrium reaction, and therefore, the amount of the aromatic monohydroxy compound is advantageously larger. However, if the amount of the aromatic monohydroxy compound used increases, a reactor having a large volume is required, and a large distillation column and the like are also required for the subsequent separation of the product. Therefore, the amount ratio of the reactant to the starting material is preferably in the range of 0.1 times to 5 times, more preferably in the range of 0.5 times to 5 times, as expressed by molar ratio of the reactant/starting material.

As described in Japanese Patent Laid-Open No. 2000-307400, when a starting material, a reactant, and a catalyst are fed to a middle stage of a multistage distillation column in the production of the aromatic carbonate, precipitation and clogging may occur in the multistage distillation column.

The reaction for producing the diaryl carbonate is an equilibrium reaction as described above, and a reaction distillation method using a multistage distillation column is thus suitable in which the equilibrium can be gradually shifted by removing the alcohol as by-product from the reaction system. In order to carry out the method, it is essential that the catalyst is present not only in the column bottom of the multistage distillation column, but also in multiple, i.e., two or more stages of the continuous multistage distillation column.

On the other hand, as described above, when the catalyst is fed to a stage above the column bottom of the multistage distillation column, precipitation and clogging may occur in the multistage distillation column.

The present inventors have studied diligently, and as a result, surprisingly found that in a case where an aliphatic carbonate, an aromatic monohydroxy compound, and a catalyst are used, even if the starting material, the reactant, and the catalyst are fed together to a stage above the bottom of a multistage distillation column in a certain range of the feed ratio of the aliphatic carbonate that is the starting material and the aromatic monohydroxy compound, the clogging of the multistage distillation column resulting from the catalyst, and the formation of a precipitate in the multistage distillation column structure are far less likely to occur, and reaction distillation can be carried out, and therefore, the yield of the aromatic carbonate can be increased.

In other words, it has been found that by feeding a particular aliphatic carbonate, aromatic monohydroxy compound, and catalyst to a stage above the column bottom of a multistage distillation column, and continuously removing an aromatic carbonate corresponding to the starting material and the reactant, in a liquid state, from the lower portion of the column, while continuously removing a low boiling component, such as an alcohol as by-product in the reaction, in a gas state, out of the reaction system, the clogging of the multistage distillation column is extremely less likely to occur, and reaction distillation can be advantageously carried out without the azeotropy of the aliphatic carbonate and the alcohol as by-product, and the aromatic carbonate can be produced in a high yield.

The amount ratio of the reactant to the starting material fed to the multistage distillation column is preferably in the range of molar ratio of 0.5 to 5.

The alcohol, the aliphatic aromatic carbonate, and the diaryl carbonate, and the like that are all products may be included in the raw materials fed to the reactor. However, the reaction is a reversible reaction, and therefore, if the concentrations of these products are too high, the reaction rate of the raw material is decreased, which may be unpreferred.

As described above, the reaction for producing aromatic carbonate is mainly related to (E1) and/or (E2), among reactions represented by the following reaction formulas (E1 to E4). In order to produce an industrially useful diaryl carbonate, it is preferred to add and perform the step of carrying out the following (E3) and (E4).

[Formula 21]

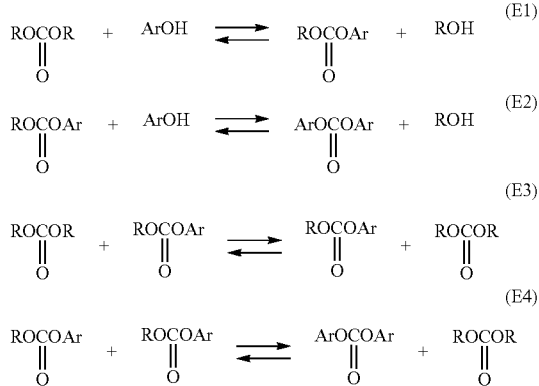

wherein R represents an aliphatic group, and Ar represents an aromatic group.

The reaction formulas (E3) and (E4) are each a transesterification reaction between molecules of the same type, and the reaction formula (E4) is usually also referred to as a disproportionation reaction.

When each of the reactions of the above reaction formulas (E1) to (E4) is performed in the step of producing the diaryl carbonate, one of each of the aliphatic carbonate and the aliphatic aromatic carbonate may be used, or two or more of each of the aliphatic carbonate and the aliphatic aromatic carbonate may be mixed and used.

In addition, one aromatic monohydroxy compound may be used, or two or more aromatic monohydroxy compounds may be mixed and used.

Further, as shown by the above presumed reaction formulas, the aromatic carbonate is produced by mainly feeding the aliphatic carbonate, the aromatic monohydroxy compound, and the catalyst, but a solvent, impurities, and by-products that do not so adversely affect the reaction may be present.

The alcohol as by-product by the reactions represented by the above reaction formulas (E1) and/or (E2) may be recovered for recycling and is preferably used for a synthesis of an aliphatic carbonate.

The aliphatic carbonate is obtained by a hitherto known method.

In terms of the effective use of the compounds, it is preferred that the aliphatic carbonate produced by the reaction represented by the above reaction formulas (E3) and/or (E4), more importantly the above formula (E4), is recovered for recycling, recirculated, and used again for the reaction represented by the above reaction formulas (E1) and/or (E3), more importantly the above formula (E1).

In other words, it is preferred to add the step of performing the transesterification reactions represented mainly by the above formulas (E1) and (E2) in a first multistage distillation column, then feeding the reaction solution comprising the aromatic carbonate removed from the lower portion of the column, to a second multistage distillation column, as it is, or after removing the starting material and the reactant, performing the disproportionation reaction represented mainly by the above formula (E4) so as to produce the useful diaryl carbonate, removing the aliphatic carbonate produced as by-product at the time, in a gas state, by distillation, from the upper portion of the distillation column, and reusing the aliphatic carbonate as the starting material in the above formula (E1) after purifying it if necessary.

An amount of the catalyst used in the above step of producing the diaryl carbonate is usually set at 0.0001 to 50% by mass as expressed by a proportion with respect to the total weight of the aliphatic carbonate and the aromatic monohydroxy compound that are feed raw materials, though it also varies depending on the type of the catalyst used, the type of the reactor, the type and amount ratio of the carbonate and the aromatic hydroxy compound, and the reaction conditions, such as reaction temperature and reaction pressure, and the like.

The catalyst used in the step of producing the diaryl carbonate described above is the above-described aryloxytitanium composition, preferably, the aryloxytitanium composition obtained by the above-described production method. The composition can also be used as the catalyst for the disproportionation reaction performed in the second multistage distillation column.

The catalyst component may be one previously reacted with the organic compounds present in the reaction system, for example, aliphatic alcohols, aromatic monohydroxy compounds, alkylaryl carbonates, diaryl carbonates, and dialkyl carbonates, one heat-treated with the raw materials and the products prior to the reaction, or one left by evaporating the low boiling point substance in the heat treatment.

The catalyst for the production of a diaryl carbonate in the present embodiment comprises an aryloxytitanium and a diaryl carbonate, wherein the content of titanium atoms constituting the above aryloxytitanium is 1% by mass or more and 15% by mass or less.

The method for producing a diaryl carbonate in the present embodiment is preferably a method comprising performing transesterification and disproportionation reactions, using a dialkyl carbonate and an aromatic hydroxy compound, in the presence of the above-described catalyst for the production of the diaryl carbonate, so as to produce a diaryl carbonate. With such a production method, the diaryl carbonate can be efficiently produced.

The method for producing the diaryl carbonate in the present embodiment more preferably comprises a step of separating the diaryl carbonate from a reaction product obtained by the above disproportionation reaction, and particularly preferably further comprises a step of recycling the reaction product, from which the diaryl carbonate is separated, into the transesterification or disproportionation reaction. When the method for producing the diaryl carbonate comprises such steps, the diaryl carbonate can be more efficiently produced.

In the step of producing the diaryl carbonate, suitable inert solvents, for example, ethers, aliphatic hydrocarbons, aromatic hydrocarbons, and halogenated aromatic hydrocarbons, may be used as the reaction solvent, for the purposes of making the reaction operation easy, completing the reaction, and the like.

An inert gas, such as nitrogen, helium, or argon, may coexist, as a substance inert to the reaction, in the reaction system, or the above inert gas and a low melting point organic compound inert to the reaction may be introduced in a gas state from the lower portion of the continuous multistage distillation column for the purpose of accelerating the evaporation of the produced low boiling point by-product.

The aromatic carbonates produced by the step of producing the diaryl carbonate described above are an aliphatic aromatic carbonate (alkylaryl carbonate) represented by the following formula (37) and/or a diaryl carbonate represented by the following formula (38).

[Formula 36]

 (37)

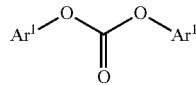 (38)

In the above formulas (37) and (38), $Ar^1$ represents an aromatic group having 5 to 30 carbon atoms. $R^1$ represents an alkyl group having 1 to 10 carbon atoms, an alicyclic group having 3 to 10 carbon atoms, or an aralkyl group having 6 to 10 carbon atoms.

A reactor used in the step of producing the diaryl carbonate described above is preferably a multistage distillation column, in terms of efficiently shifting the equilibrium to the production system side. It is particularly preferred to apply a continuous process using a multistage distillation column.

The multistage distillation column is a distillation column having multiple stages in which the theoretical plate number of distillation is 2 or more, and may be of any type as long as continuous distillation is possible.

Such a multistage distillation column may be of any type usually used as a multistage distillation column, for example, a plate column type using trays, such as a bubble cap tray, a perforated plate tray, a valve tray, a chimney tray, and a countercurrent tray, and a packed column type packed with various packings, such as a Raschig ring, a Lessing ring, a Pall ring, a Berl saddle, an Intalox saddle, a Dixon packing, a Mcmahon packing, a Heli pack, a Sulzer packing, and Mellapak.

Further, a plate-packed column type having both a plate portion and a portion packed with a packing is also preferably used.

When the continuous process is carried out using the multistage distillation column, aromatic carbonates are produced by continuously feeding the starting material and the reactant into a continuous multistage distillation column, and allowing the reaction between both of the substances in a liquid phase or a gas-liquid phase in the presence of a metal-containing catalyst in the distillation column, while on the one hand removing a high boiling point reaction mixture comprising a produced aromatic carbonate or aromatic carbonate mixture, in a liquid state, from the lower portion of the distillation column, and on the other hand continuously removing a low boiling point reaction mixture comprising a produced by-product, in a gas state, by distillation from the upper portion of the distillation column.

In the step of producing the diaryl carbonate described above, the reaction occurs in the multistage distillation column in which the catalyst is present, and therefore, an amount of the resulting reaction products usually depends on the holdup in the distillation column.

In other words, when distillation columns having the same column height and the same column diameter are compared for use, a distillation column having a larger holdup is preferred in that the residence time, that is, reaction time, of the reaction solution can be longer.

However, if the holdup is too large, the residence time is long, and, it is thus likely that a side reaction proceeds and flooding occurs.

Therefore, the holdup of the distillation column is usually 0.005 to 0.75 as expressed by the ratio of the volume of the holdup to the empty column volume of the multistage distillation column, though it can also change depending on the distillation conditions and the type of the distillation column.

In the step of producing the diaryl carbonate described above, when a reflux ratio is increased, an effect of distilling the aliphatic alcohol into a vapor phase increases, and therefore, a concentration of the aliphatic alcohol in the removed vapor can be increased.

However, if the reflux ratio is increased too much, the required thermal energy is excessive, which is unpreferred.

The aliphatic alcohol may be concentrated after extraction from the distillation column, and therefore, refluxing is not always necessary.

The reflux ratio is thus usually 0 to 20, preferably 0 to 10.

Specifically, when the transesterification reaction typically represented by the above-described reaction formula (E1) is carried out, the aliphatic carbonate, the aromatic monohydroxy compound, and the catalyst are fed to the multistage distillation column, after being mixed or from separate places, and the aromatic carbonate that is a product is continuously removed in a liquid state from the bottom of the distillation column, while the low boiling component, such as the alcohol as by-product, is continuously removed in a gas state by distillation from the upper portion of the distillation column.

At this time, the catalyst may be fed from any place of the multistage distillation column, but is preferably fed at a position above the column bottom of the distillation column, and is more preferably fed at a position above the middle of the distillation column.

When the disproportionation reaction typically represented by the above formula (E4) that can be additionally performed is carried out, the aliphatic aromatic carbonate and the catalyst are fed to the multistage distillation column, and the diaryl carbonate that is a product is continuously removed in a liquid state from the bottom of the distillation column, while the low boiling component, such as the aliphatic carbonate produced as by-product, is continuously removed in a gas state by distillation from the upper portion of the distillation column.

The reaction temperature in the step of producing the diaryl carbonate described above varies depending on a type of the starting material, the reactant, and the catalyst used. However, usually, the temperature at the column bottom of the multistage distillation column is in the range of 50 to 350° C., preferably 150 to 250° C.

The reaction pressure may be any of reduced pressure, ordinary pressure, and increased pressure, and is usually in the range of 0.1 to $2.0 \times 10^7$ Pa, though it varies depending on a type of the raw feed compounds used, the reaction temperature, and the like.

The step of producing the diaryl carbonate described above is characterized by producing a diaryl carbonate by continuously feeding an aliphatic carbonate as a starting material, an aromatic monohydroxy compound, and a metal-containing catalyst to a multistage distillation column to react them, and continuously removing aromatic carbonates corresponding to the starting material and the reactant, in a liquid state, from the lower portion of the column, while continuously removing a low boiling component, such as an alcohol as by-product in the reaction, in a gas state, out of the reaction system. Further, it is possible to add a step of continuously feeding the reaction solution removed from the lower portion of the column, to a second multistage distillation column, as it is, or after removing the starting material and/or the reactant, to carry out a disproportionation reaction, continuously removing a low boiling component, such as an aliphatic carbonate produced as by-product in the disproportionation reaction, in a gas state, by distillation out of the reaction system, and continuously removing aromatic carbonates including a diaryl carbonate, in a liquid state, from the lower portion of the column.

It is preferred to carry out the step of continuously removing aromatic carbonates including a diaryl carbonate, in a liquid state, from the lower portion of the column described above in order to increase the yield of the diaryl carbonate and also recycle the aliphatic carbonate produced as by-product in the disproportionation reaction.

The liquid material comprising the diaryl carbonate removed from the lower portion of the above second distillation column is usually introduced into a distillation column to purify the diaryl carbonate by distillation.

The diaryl carbonate is removed in a gas state from the upper portion of the column, and high boiling point substances, such as by-products, a Fries rearrangement product of the aromatic carbonate, and the catalyst component, are removed from the lower portion of the column.

The high boiling point substances may be blown down as they are, or it is possible to blow down only part of the high boiling point substances and recycle the remainder as the catalyst component again.

In recycle use, the catalyst component may be used after removing the solids or purification, and may be mixed with a newly prepared catalyst before use.

As described above, the aryloxytitanium composition in the present embodiment, for example, the aryloxytitanium composition obtained by the above-described production method, is extremely useful as a composition for storage and/or transfer, and in the production of the diaryl carbonate, using the composition, a diaryl carbonate having high quality can be obtained, and the aryloxytitanium composition is industrially extremely useful.

EXAMPLES

The present invention will be specifically described by way of the following examples and comparative examples, although the present invention is not limited to the following examples.

First, analysis methods applied to the examples and the comparative examples will be described below.

<Analysis>
(NMR Analysis)
Measuring apparatus: JNM-A400 FT-NMR system, manufactured by JEOL Ltd., Japan
(1) Preparation of $^1$H and $^{13}$C-NMR Analysis Samples About 0.3 g of a sample solution was weighed, and about 0.7 g of deuterated chloroform (99.8%, manufactured by Aldrich Chemical Co., U.S.A.) and, as an internal reference, 0.05 g of tetramethyltin (Wako first grade, manufactured by Wako Pure Chemical Industries, Ltd., Japan) were then added thereto. The resulting solution was uniformly mixed for use as an NMR analysis sample.

(2) Quantitative Analysis

Analysis was carried out for each reference material. Quantitative analysis of the analysis sample solution was then carried out based on the resulting calibration curve.

(Liquid Chromatography Analysis)
Measuring apparatus: LC-10AT system, manufactured by Shimadzu Corporation, Japan
Column: two Inertsil-ODS columns connected in series, manufactured by GL Sciences, Inc., Japan
Developing solvent: Mixture of water (liquid A) and acetonitrile (liquid B)
Developing solvent flow rate: 1 mL/min
Column temperature: 35° C.
Detector: R.I. detector (refractometer) and PDA detector (photo diode array detector), measurement wavelength range from 200 nm to 300 nm
(1) Liquid Chromatography Analysis Samples About 0.1 g of a sample was weighed followed by the addition of about 1 g of tetrahydrofuran (dry, manufactured by Wako Pure Chemical Industries, Ltd., Japan) and about 0.02 g of an internal reference and mixing to uniformity to obtain a solution used as a liquid chromatography analysis sample.

(2) Quantitative Analysis

Analysis was carried out for each reference material, and quantitative analysis was carried out for the analysis sample solution based on the resulting calibration curve.

(Water Analysis)
Measuring apparatus: CA-21 trace moisture meter, manufactured by Mitsubishi Chemical Analytech Co., Ltd., Japan
(1) Quantitative Analysis About 1 g of a sample was weighed followed by the injection of the sample into the trace moisture meter and quantifying a moisture content for the sample.

(Analysis of Ti Concentrations in Liquid and Solid)
Apparatus: Ion Chromatography IC 2001 (manufactured by Toso Corporation, Japan)
Column: SuperIC-CR
Developing liquid: A solution was used, which was obtained by mixing 1 L of water, about 0.25 g of 18-crown-6 (manufactured by Wako Pure Chemical Industries, Ltd., Japan), and about 2.1 mL of 2 mol/L methanesulfonic acid (manufactured by Wako Pure Chemical Industries, Ltd., Japan).

(1) Ion Chromatography Analysis Sample

About 0.15 g of a sample was weighed. About 1 g of toluene and about 15 g of a 2 mmol/L aqueous solution of nitric acid were added thereto, and they were sufficiently stirred. The resulting solution was then left still for about 2 hours. The water layer was separated, and used as an ion chromatography analysis sample.

(2) Quantitative Analysis

A calibration curve was prepared by using reference solutions. A Ti amount in an analysis sample solution was quantified based on the calibration curve.

The names of compounds in the following examples may be given according to not only the nomenclature defined by IUPAC but also popular naming.

A trace moisture meter analyzed the reaction solution with time, and it was confirmed that the added water was consumed in a hydrolysis reaction and the analyzed value became constant.

Production Examples 2 to 9

A hydrolytic condensation step of tetraalkoxytitanium was carried out in the same manner as in the above-mentioned [production example 1] except that tetraalkoxytitanium to be used, an alcohol type, a dilution concentration, an added amount of water, and a temperature were changed.

The tetraalkoxytitanium used, the alcohol type, a moisture content of the alcohol, the temperature condition, an addition time, and an added amount of water to Ti are shown in the following Table 2.

TABLE 2

| | Tetraalkoxytitanium | Used amount | Alcohol | Used amount | Hydrous alcohol | Addition temperature | Addition time | Added amount of water (mol per mol of Ti) |
|---|---|---|---|---|---|---|---|---|
| Production example 2 | Tetraethoxytitanium | 228 Kg | Ethanol | 460 Kg | Ethanol (containing 80% by mass of water) | 0° C. | 1 hour | 0.5 |
| Production example 3 | Tetra-(n-butoxy)titanium | 340 Kg | n-butanol | 222 Kg | n-butanol (containing 2% by mass of water) | 50° C. | 20 hours | 0.2 |
| Production example 4 | Tetra-(n-butoxy)titanium | 170 Kg | n-butanol | 222 Kg | n-butanol (containing 2% by mass of water) | 10° C. | 5 hours | 0.8 |
| Production example 5 | Tetra-(n-butoxy)titanium | 340 Kg | n-butanol | 148 Kg | n-butanol (containing 5% by mass of water) | 0° C. | 4 hours | 0.67 |
| Production example 6 | Tetra-(n-butoxy)titanium | 340 Kg | n-butanol | 148 Kg | n-butanol (containing 4% by mass of water) | 0° C. | 2 hours | 0.91 |
| Production example 7 | Tetra-(n-butoxy)titanium | 340 Kg | n-butanol | 148 Kg | n-butanol (containing 5% by mass of water) | 0° C. | 0.5 hours | 0.83 |
| Production example 8 | Tetra-(n-butoxy)titanium | 340 Kg | n-butanol | 148 Kg | n-butanol (containing 7% by mass of water) | 30° C. | 10 hours | 0.66 |
| Production example 9 | Tetraisopropoxytitanium | 284 Kg | Isopropanol | 120 Kg | Isopropanol (containing 20% by mass of water) | −10° C. | 0.1 hour | 0.75 |

(Analysis of Presence of Ti—O—Ti Linkage)

X-ray crystal structure analysis of a solid aryloxytitanium composition was performed using the following measuring apparatus to determine an interatomic distance. Presence of a Ti—O—Ti linkage was determined by an interaction between atoms when the interatomic distance is smaller than the sum of ion radii. The sum of ion radii of a titanium atom and an oxygen atom is 2.87 angstrom.

Measuring apparatus: Automatic Single Crystal X-Ray Crystal Structure Analysis System RASA-7 (manufactured by Rigaku Corporation).

Production Example 1

Step X: Hydrolytic Condensation Step of Tetraalkoxytitanium 340 kg of tetrabutoxytitanium (Tyzor BTP, manufactured by E. I. du Pont de Nemours & Company) was introduced to a reactor equipped with a stirrer. The reactor was equipped with a cooling coil, a heating jacket, and a distillation column. 148 kg of butanol was then introduced thereto, and an internal liquid temperature was adjusted to 0° C.

Hydrous butanol having a water concentration set to 5% by mass (% by weight) was adjusted to 0° C. in another reactor equipped with a stirrer. The reactor was equipped with a cooling coil, a heating jacket, and a distillation column.

The hydrous butanol was added into the reactor under stirring through a line.

The addition time was set to 1 hour, and an added amount of water was set to 0.5 mol per mol of Ti atoms in the reactor.

Production Example 10

Step Y: Concentration Step

The reaction solution obtained in the [production example 1] was heated under stirring, and n-butanol was evaporated using the distillation column after the reaction solution reached 150° C.

A composition of the evaporated liquid was analyzed by gas chromatography, and it was confirmed that the evaporated increment was nearly zero. The distillation was then completed.

When a transparent and colorless liquid left in the reactor was analyzed to determine Ti content and alkoxy group contents, it was found that butoxy polytitanoxane having an average degree of polymerization of 2 had been produced.

Production Examples 11 to 18

A concentration step was performed in the same manner as in the production example 10 except that the reaction solutions obtained in the above-mentioned [production examples 2 to 9] were used.

The reaction solutions used and the average degrees of polymerization of the obtained polytitanoxane having the alkoxy group are shown in the following Table 3.

TABLE 3

| | Reaction solution used | Average degree of polymerization |
|---|---|---|
| Production example 11 | Reaction solution produced in production example 2 | 1.98 |
| Production example 12 | Reaction solution produced in production example 3 | 1.25 |
| Production example 13 | Reaction solution produced in production example 4 | 7.9 |
| Production example 14 | Reaction solution produced in production example 5 | 4 |
| Production example 15 | Reaction solution produced in production example 6 | 12 |
| Production example 16 | Reaction solution produced in production example 7 | 6 |
| Production example 17 | Reaction solution produced in production example 8 | 2.9 |
| Production example 18 | Reaction solution produced in production example 9 | 4 |

Example 1

In this example, as a step A, polytitanoxane having an alkoxy group and an aromatic hydroxy compound were reacted, and an alcohol produced as by-product was evaporated by distillation so as to obtain a crude polytitanoxane composition having an aryloxy group.

About 194 kg of light yellow transparent polytitanoxane having a butoxy group (B4, manufactured by Nippon Soda Co., Ltd.) was introduced to a reactor equipped with a stirrer. The reactor was equipped with a cooling coil, a heating jacket, and a distillation column. The polytitanoxane was then adjusted to 120° C.

About 500 kg of phenol of 80° C. was then introduced thereto through a line. An internal liquid temperature was adjusted to 120° C.

The addition time was 1 hour, and stirring was then continued for about 4 hours to evaporate butanol produced as by-product using the distillation column.

From the analysis of the distillate liquid, it was confirmed that the amount of butanol produced as by-product (nearly the same amount as that of the butoxy group contained in the fed polytitanoxane composition) was evaporated. A temperature and a pressure were then adjusted so that the internal liquid temperature of the reactor was set to 180° C., and the distillation of phenol was started. In this case, the pressure within the system was finally about 26 kPa.

Once it was confirmed that no or little more distillate was produced, the reaction was completed.

Red polytitanoxane having a phenoxy group was produced in the system. From the analysis, the butoxy group was not left, and polytitanoxane having the phenoxy group, where it was replaced by the phenoxy group, having an average degree of polymerization of about 4 was obtained. As a result of the X-ray structure analysis of the polytitanoxane having the phenoxy group, a Ti—O—Ti linkage was confirmed.

Examples 2 to 10

Polytitanoxane compositions having an aryloxy group were obtained in the same manner as in the [example 1] except that the reaction solutions obtained in the above-mentioned [production examples 10 to 18] were used, and aromatic hydroxy compounds shown in the following Table 4 were used.

The obtained polytitanoxane compositions having the aryloxy group are shown in the following Table 4.

Change in an average degree of polymerization exceeding an analysis error before and after the step (A) was not observed in each case. As a result of the X-ray structure analysis of the polytitanoxane composition having the aryloxy group, a Ti—O—Ti linkage was confirmed.

TABLE 4

| | Reaction solution used | Aromatic hydroxy compound (ArOH) | Molar equivalents of ArOH with respect to alkoxy group | Obtained polytitanoxane having aryloxy group |
|---|---|---|---|---|
| Example 2 | Reaction solution produced in production example 10 | Phenol | 5 | polytitanoxane having phenoxy group |
| Example 3 | Reaction solution produced in production example 11 | p-cresol | 15 | polytitanoxane having p-cresyloxy group |
| Example 4 | Reaction solution produced in production example 12 | Phenol | 20 | polytitanoxane having phenoxy group |
| Example 5 | Reaction solution produced in production example 13 | Phenol | 30 | polytitanoxane having phenoxy group |
| Example 6 | Reaction solution produced in production example 14 | Phenol | 50 | polytitanoxane having phenoxy group |
| Example 7 | Reaction solution produced in production example 15 | Phenol | 10 | polytitanoxane having phenoxy group |
| Example 8 | Reaction solution produced in production example 16 | Phenol | 10 | polytitanoxane having phenoxy group |
| Example 9 | Reaction solution produced in production example 17 | Phenol | 10 | polytitanoxane having phenoxy group |
| Example 10 | Reaction solution produced in production example 18 | Phenol | 10 | polytitanoxane having phenoxy group |

Example 11

This example comprised a step of adding a diaryl carbonate to a polytitanoxane composition having an R—O—Ti linkage, and evaporating a component having a lower boiling point than that of the diaryl carbonate, together with the diaryl carbonate, so as to obtain a polytitanoxane composition having an aryloxy group in a step (1), or a step of adding a diaryl carbonate to a crude polytitanoxane composition having an aryloxy group and evaporating a component having a lower boiling point than that of the diaryl carbonate, together with the diaryl carbonate, so as to obtain a polytitanoxane composition having an aryloxy group in a step (B).

After the reaction solution obtained in the above-mentioned [example 1] was returned to a normal pressure with nitrogen, diphenyl carbonate was added under stirring in an amount of 2.5 mol per mol of Ti atoms contained in the reaction solution.

In this case, an internal liquid temperature of the reactor was 150° C., and diphenyl carbonate was also added in a molten state of about 150° C.

The addition time was about 1 hour.

The temperature of the liquid of the reactor was gradually raised, and the internal pressure of the reactor was gradually lowered, thereby starting the distillation of a component having a lower boiling point than that of the diphenyl carbonate, together with the diphenyl carbonate from the distillation column.

After the pressure within the system was gradually returned to a normal pressure with nitrogen gas when about a half amount of the added diphenyl carbonate was distilled (finally, the temperature within the system was about 210° C., and the pressure was 3 kPa), diphenyl carbonate of about a half amount of that of the previously added diphenyl carbonate was added again.

The diphenyl carbonate was added in a molten state of about 150° C.

The addition time was about 1 hour.

The temperature of the reaction solution was then set to about 210° C., and the internal pressure of the reactor was gradually lowered, thereby starting the distillation of a component having a lower boiling point than that of the diphenyl carbonate, together with the diphenyl carbonate from the distillation column.

The pressure within the system was gradually returned to a normal pressure with nitrogen gas when diphenyl carbonate in nearly the same amount as that of the diphenyl carbonate added at the second time was distilled (finally, the temperature within the system was about 210° C., and the pressure was 3 kPa).

A component containing the diaryl carbonate evaporated at the first time was colored in yellow, and contained about 120 ppm of Ti atoms.

The component also contained about 400 ppm of a chlorine component.

A component containing the diaryl carbonate evaporated at the second time was a transparent and colorless liquid (a white solid when the liquid was cooled), and had less than 1 ppm of Ti atoms.

A chlorine component was also 10 ppm or less. An average degree of polymerization of the polytitanoxane composition and a Ti—O—Ti linkage were not changed before and after the step.

Examples 12 to 20

Polytitanoxane (or composition) having an aryloxy group and a diaryl carbonate to be used were changed as shown in the following Table 5.

Polytitanoxane having an aryloxy group was obtained in the same manner as in the above-mentioned [example 11] with the exception of the change.

The reaction solution used, the diaryl carbonate, the added amount of the diaryl carbonate, Ti in the component evaporated, and the chlorine content are shown in the following Table 5.

Change in the average degree of polymerization of the polytitanoxane composition and the Ti—O—Ti linkage exceeding an analysis error before and after a step (A) was not observed in each case.

Although both the Ti content and the chlorine content were high in the component containing the diaryl carbonate obtained in the first distillation, the Ti content and the chlorine content were less in the second evaporated component.

TABLE 5

| | | | Added amount of diaryl carbonate (molar equivalents with respect to Ti atoms in feeding reaction solution) | | | Ti and chlorine contents in component evaporated (ppm) | | | | | |
|---|---|---|---|---|---|---|---|---|---|---|---|
| | | | | | | First time | | Second time | | Third time | |
| | Reaction solution used | Diaryl carbonate | First time | Second time | Third time | Ti | Chlorine | Ti | Chlorine | Ti | Chlorine |
| Example 12 | Reaction solution produced in example 2 | Diphenyl carbonate | 3.2 | 1.6 | Not carried out | 150 | 750 | <1 | 10 | Not carried out | Not carried out |
| Example 13 | Reaction solution produced in example 3 | Bis(p-cresyl)carbonate | 3.5 | 1.7 | Not carried out | 310 | 400 | <1 | 5 | Not carried out | Not carried out |
| Example 14 | Reaction solution produced in example 4 | Diphenyl carbonate | 3.5 | 1.7 | Not carried out | 100 | 250 | 5 | 6 | Not carried out | Not carried out |
| Example 15 | Reaction solution produced in example 5 | Diphenyl carbonate | 2.4 | 1 | Not carried out | 120 | 360 | 1 | 15 | Not carried out | Not carried out |
| Example 16 | Reaction solution produced in example 6 | Diphenyl carbonate | 5 | 3 | Not carried out | 5 | 240 | 3 | 20 | Not carried out | Not carried out |
| Example 17 | Reaction solution produced in example 7 | Diphenyl carbonate | 1 | 2 | 2 | 600 | 800 | 120 | 200 | 2 | 15 |
| Example 18 | Reaction solution produced in example 8 | Diphenyl carbonate | 4 | 1 | Not carried out | 80 | 550 | 1 | 10 | Not carried out | Not carried out |
| Example 19 | Reaction solution produced in example 9 | Diphenyl carbonate | 10 | Not carried out | Not carried out | 30 | 110 | Not carried out | Not carried out | Not carried out | Not carried out |
| Example 20 | Reaction solution produced in example 10 | Diphenyl carbonate | 5 | 1 | Not carried out | 10 | 230 | <1 | 30 | Not carried out | Not carried out |

TABLE 6

|  | Titanium content (% by mass) | Diaryl carbonate (% by mass) | Compound having boiling point of 150° C. or less (alcohols, water) (ppm) |
|---|---|---|---|
| Example 11 | 8.6 | 50 | 1 |
| Example 12 | 7.0 | 52 | 2 |
| Example 13 | 5.9 | 54 | 0.3 |
| Example 14 | 6.5 | 51 | 1 |
| Example 15 | 9.0 | 50 | 1 |
| Example 16 | 5.7 | 65 | 2 |
| Example 17 | 6.0 | 68 | 2 |
| Example 18 | 5.9 | 67 | 1 |
| Example 19 | 3.5 | 79 | 2 |
| Example 20 | 5.8 | 65 | 0.5 |

Example 21

This example performed a step of adding a diaryl carbonate to a polytitanoxane composition having an R—O—Ti linkage and evaporating a component having a lower boiling point than that of the diaryl carbonate, together with the diaryl carbonate, so as to obtain a polytitanoxane composition having an aryloxy group in a step (1).

After a butyl titanate dimer (B2, manufactured by Nippon Soda Co., Ltd.) was put into a reactor, and was returned to a normal pressure with nitrogen, the diphenyl carbonate was added in an amount of 10 mol per mol of Ti atoms contained in the reaction solution, under stirring.

In this case, an internal liquid temperature of the reactor was 150° C., and the diphenyl carbonate was also added in a molten state of about 150° C.

The addition time was about 1 hour.

The temperature of the liquid of the reactor was gradually raised, and the internal pressure of the reactor was gradually lowered, thereby starting the distillation of a component having a lower boiling point than that of the diphenyl carbonate, together with the diphenyl carbonate from the distillation column.

After the pressure within the system was gradually returned to a normal pressure with nitrogen gas when about a half amount of the added diphenyl carbonate was distilled (finally, the temperature within the system was about 210° C., and the pressure was 3 kPa), diphenyl carbonate of about a half amount of that of the previously added diphenyl carbonate was added again.

The diphenyl carbonate was added in a molten state at about 140° C.

The addition time was about 1 hour.

The temperature of the solution in the reactor was then set to about 210° C., and the internal pressure of the reactor was gradually lowered, thereby starting the distillation of a component having a lower boiling point than that of the diphenyl carbonate, together with the diphenyl carbonate from the distillation column.

The pressure within the system was gradually returned to a normal pressure with nitrogen gas when diphenyl carbonate in nearly the same amount as that of the diphenyl carbonate added at the second time was distilled (finally, the temperature within the system was about 210° C., and the pressure was 3 kPa). A component containing the diaryl carbonate evaporated at the first time was colored in yellow, and contained about 120 ppm of Ti atoms. The component also contained about 400 ppm of a chlorine component. A component containing the diaryl carbonate evaporated at the second time was a transparent and colorless liquid (a white solid when the liquid was cooled), and had less than 10 ppm of Ti atoms. A chlorine component was also 10 ppm or less.

An average degree of polymerization was not changed before and after the step. As the remaining liquid, polytitanoxane (an average degree of polymerization of 2) having a phenoxy group was obtained. It was presumed to have a $(PhO)_3$—Ti—O—Ti—$(OPh)_3$ structure.

The content of titanium atoms in the composition obtained in this example was 3.4% by mass; the content of the diaryl carbonate was 75% by mass; and the content of the compound having the boiling point of 150° C. or less (n-butanol, water) was 2 ppm.

Reference Example 1

Tetraaryloxytitanium was synthesized in this example.

About 170 kg of transparent and colorless tetrabutoxytitanium (manufactured by Nippon Soda Co., Ltd.) was introduced to a reactor equipped with a stirrer. The reactor was equipped with a cooling coil, a heating jacket, and a distillation column. The tetrabutoxytitanium was adjusted to 120° C.

About 500 kg of phenol of 80° C. was then introduced thereto through a line. An internal liquid temperature was adjusted to 120° C.

The addition time was set to 1 hour, and stirring was then continued for about 4 hours to evaporate butanol produced as by-product using the distillation column.

From the analysis of the distillate liquid, it was confirmed that the amount of butanol produced as by-product (nearly the same amount as that of the butoxy group contained in the fed polytitanoxane composition) was evaporated. A temperature and a pressure were then adjusted so that the internal liquid temperature of the reactor was set to 180° C., and the distillation of phenol was started (in this case, the pressure within the system was finally about 26 kPa).

Once it was confirmed that no or little more distillate was produced, the reaction was completed.

From the analysis, the butoxy group was not left in the system, and tetraphenoxytitanium where it was replaced by the phenoxy group was obtained. The content of titanium atoms in the composition obtained in this reference example was 11% by mass; the content of diaryl carbonate was 0% by mass; and the content of the compound having the boiling point of 150° C. or less (n-butanol, water) was 3 ppm.

Example 22

After the reactor containing the tetraphenoxytitanium obtained in the above-mentioned [reference example 1] was returned to a normal pressure with nitrogen, diphenyl carbonate was added in an amount of 3 mol per mol of Ti atoms contained in the reaction solution, under stirring.

In this case, an internal liquid temperature of the reactor was 150° C., and the diphenyl carbonate was also added in a molten state of about 140° C.

The addition time was about 1 hour.

The temperature of the liquid of the reactor was gradually raised, and the internal pressure of the reactor was gradually lowered, thereby starting the distillation of a component having a lower boiling point than that of the diphenyl carbonate, together with the diphenyl carbonate from the distillation column.

After the pressure within the system was gradually returned to a normal pressure with nitrogen gas when about a half amount of the added diphenyl carbonate was distilled (finally, the temperature within the system was about 210° C., and the pressure was 3 kPa), diphenyl carbonate of about a half amount of that of the previously added diphenyl carbonate was added again.

The diphenyl carbonate was added in a molten state of about 150° C.

The addition time was about 1 hour.

The temperature of the solution in the reactor was then set to about 210° C., and the internal pressure of the reactor was gradually lowered, thereby starting the distillation of a component having a lower boiling point than that of the diphenyl carbonate, together with the diphenyl carbonate from the distillation column.

The pressure within the system was gradually returned to a normal pressure with nitrogen gas when diphenyl carbonate in nearly the same amount as that of the diphenyl carbonate added at the second time was distilled (finally, the temperature within the system was about 210° C., and the pressure was 3 kPa).

A component containing a diaryl carbonate evaporated at the first time was colored in yellow, and contained about 120 ppm of Ti atoms.

The component also contained about 400 ppm of a chlorine component. A component containing a diaryl carbonate evaporated at the second time was a transparent and colorless liquid (a white solid when the liquid was cooled), and had less than 10 ppm of Ti atoms. A chlorine component was also 10 ppm or less. The tetraphenoxytitanium was left in the system. The content of titanium atoms in the composition obtained in the example was 5.6% by mass; the content of the diaryl carbonate was 50% by mass; and the content of the compound having the boiling point of 150° C. or less (n-butanol, water) was 1 ppm.

Example 23

In this example, a step for adjusting a component ratio of a polytitanoxane composition having an aryloxy group and a diaryl carbonate was performed in a step (C).

Diphenyl carbonate was added in the form of a liquid into the remaining liquid obtained in the above-mentioned [example 22] under stirring, so as to obtain a polytitanoxane composition having an aryloxy group, adjusted so that a concentration of Ti atoms was 5% by mass.

The content of titanium atoms in the composition obtained in the example was 5% by mass; the content of the diaryl carbonate was 56% by mass; and the content of the compound having the boiling point of 150° C. or less (n-butanol, water) was 2 ppm.

Examples 24 to 33

Polytitanoxane compositions having an aryloxy group were obtained in the same manner as in the [example 23] except that types of a titanium compound to be used and a diaryl carbonate and an adjusted concentration were different.

The amount of diaryl carbonate was adjusted either by adding the diaryl carbonate if it was insufficient, or by evaporating it if it was in excess.

The reaction solution used, diaryl carbonate, a concentration of Ti atoms in the adjusted composition (% by mass), a content of the diaryl carbonate, and a content of a compound having a boiling point of 150° C. or less are shown in the following Table 7.

TABLE 7

|  |  |  | In adjusted composition | | |
| --- | --- | --- | --- | --- | --- |
|  | Reaction solution used | Diaryl carbonate | Content of Ti atoms (% by mass) | Content of diaryl carbonate (% by mass) | Compound having boiling point of 150° C. or less (ppm) |
| Example 24 | Reaction solution produced in example 11 | Diphenyl carbonate | 1 | 94 | 1 |
| Example 25 | Reaction solution produced in example 12 | Diphenyl carbonate | 4 | 73 | 2 |
| Example 26 | Reaction solution produced in example 13 | Bis(p-cresyl)carbonate | 5 | 61 | 1 |
| Example 27 | Reaction solution produced in example 14 | Diphenyl carbonate | 10 | 25 | 4 |
| Example 28 | Reaction solution produced in example 15 | Diphenyl carbonate | 12 | 33 | 2 |
| Example 29 | Reaction solution produced in example 16 | Diphenyl carbonate | 13 | 20 | 5 |
| Example 30 | Reaction solution produced in example 17 | Diphenyl carbonate | 10 | 47 | 2 |
| Example 31 | Reaction solution produced in example 18 | Diphenyl carbonate | 2 | 89 | 1 |
| Example 32 | Reaction solution produced in example 19 | Diphenyl carbonate | 8 | 52 | 5 |
| Example 33 | Reaction solution produced in example 20 | Diphenyl carbonate | 3 | 82 | 2 |

Reference Examples 2 to 12

A polytitanoxane composition having an aryloxy group was produced without evaporating a composition having a lower boiling point than that of a diaryl carbonate.

The polytitanoxane composition having the aryloxy group was obtained in the same manner as in the above-mentioned [reference example 1] except for the condition.

The reaction solution used, the diaryl carbonate, the concentration of Ti atoms in the composition (% by mass), the content of the diaryl carbonate, and the content of the compound having the boiling point of 150° C. or less are shown in the following Table 8.

TABLE 8

|  | Reaction solution used | Diaryl carbonate | In adjusted composition | |
|---|---|---|---|---|
|  |  |  | Content of Ti atoms (% by mass) | Content of diaryl carbonate (% by mass) |
| Reference example 2 | Reaction solution produced in example 1 | Diphenyl carbonate | 1 | 94 |
| Reference example 3 | Reaction solution produced in example 2 | Diphenyl carbonate | 1 | 93 |
| Reference example 4 | Reaction solution produced in example 3 | Bis(p-cresyl)carbonate | 5 | 61 |
| Reference example 5 | Reaction solution produced in example 4 | Diphenyl carbonate | 10 | 25 |
| Reference example 6 | Reaction solution produced in example 5 | Diphenyl carbonate | 12 | 33 |
| Reference example 7 | Reaction solution produced in example 6 | Diphenyl carbonate | 13 | 20 |
| Reference example 8 | Reaction solution produced in example 7 | Diphenyl carbonate | 10 | 46 |
| Reference example 9 | Reaction solution produced in example 8 | Diphenyl carbonate | 2 | 89 |
| Reference example 10 | Reaction solution produced in example 9 | Diphenyl carbonate | 8 | 52 |
| Reference example 11 | Reaction solution produced in example 10 | Diphenyl carbonate | 3 | 82 |
| Reference example 12 | Reaction solution produced in reference example 1 | Diphenyl carbonate | 5 | 54 |

Examples 34 to 44

In these examples, polytitanoxane compositions having an aryloxy group, which are storage compositions were obtained.

About 900 L of each of the polytitanoxane compositions having an aryloxy group, obtained in the above-mentioned [examples 23 to 33] was put into a transport container (made of SUS304 and having two nozzles provided at upper and lower positions) of 1000 L, and was cooled for storage.

Although some of the polytitanoxane compositions were completely solidified into their insides, some other were in a liquid form.

The polytitanoxane compositions were stored for about three years (from January, 2006 to January, 2009).

The polytitanoxane compositions were stored in a temperature range from as low as −2° C. to as high as about 65° C. in a warehouse throughout the three years.

The inside of each container after the storage was checked, and a portion of the composition near the wall surface of the container was sampled and subjected to metal analysis. Concentrations of metals other than Ti were kept almost constant before and after the storage.

TABLE 9

| | Stored composition | Increase of metal components other than Ti |
|---|---|---|
| Example 34 | Composition of example 23 | Within 5% increase as compared with analyzed value before storage |
| Example 35 | Composition of example 24 | Within 5% increase as compared with analyzed value before storage |
| Example 36 | Composition of example 25 | Within 5% increase as compared with analyzed value before storage |
| Example 37 | Composition of example 26 | Within 5% increase as compared with analyzed value before storage |
| Example 38 | Composition of example 27 | Within 5% increase as compared with analyzed value before storage |
| Example 39 | Composition of example 28 | Within 5% increase as compared with analyzed value before storage |
| Example 40 | Composition of example 29 | Within 5% increase as compared with analyzed value before storage |

TABLE 9-continued

| | Stored composition | Increase of metal components other than Ti |
|---|---|---|
| Example 41 | Composition of example 30 | Within 5% increase as compared with analyzed value before storage |
| Example 42 | Composition of example 31 | Within 5% increase as compared with analyzed value before storage |
| Example 43 | Composition of example 32 | Within 5% increase as compared with analyzed value before storage |
| Example 44 | Composition of example 33 | Within 5% increase as compared with analyzed value before storage |

Comparative Examples 1 to 11

The polytitanoxane compositions having the aryloxy group, produced in the reference examples 2 to 12 were stored as storage composition in the same manner as in the above-mentioned [examples 34 to 44].

The storage results are shown in the following Table 10.

TABLE 10

| | Stored composition | Increase of metal components other than Ti |
|---|---|---|
| Comparative example 1 | Composition of reference example 2 | Increase of 10% or more as compared with content of analyzed value before storage. |
| Comparative example 2 | Composition of reference example 3 | Increase of 10% or more as compared with content of analyzed value before storage. |
| Comparative example 3 | Composition of reference example 4 | Increase of 10% or more as compared with content of analyzed value before storage. |
| Comparative example 4 | Composition of reference example 5 | Increase of 10% or more as compared with content of analyzed value before storage. |
| Comparative example 5 | Composition of reference example 6 | Increase of 10% or more as compared with content of analyzed value before storage. |

TABLE 10-continued

| | Stored composition | Increase of metal components other than Ti |
|---|---|---|
| Comparative example 6 | Composition of reference example 7 | Increase of 10% or more as compared with content of analyzed value before storage. |
| Comparative example 7 | Composition of reference example 8 | Increase of 10% or more as compared with content of analyzed value before storage. |
| Comparative example 8 | Composition of reference example 9 | Increase of 10% or more as compared with content of analyzed value before storage. |
| Comparative example 9 | Composition of reference example 10 | Increase of 10% or more as compared with content of analyzed value before storage. |
| Comparative example 10 | Composition of reference example 11 | Increase of 10% or more as compared with content of analyzed value before storage. |
| Comparative example 11 | Composition of reference example 12 | Increase of 10% or more as compared with content of analyzed value before storage. |

Examples 45 to 48

About 900 L of each of the polytitanoxane compositions having the aryloxy group, obtained in the examples 24, 25, 31, and 33 was put into a transport container (made of SUS304 and having two nozzles provided at upper and lower positions) of 1000 L. The container was transferred to diphenyl carbonate production facilities which was in Kurashiki-shi, Okayama, Japan from Nobeoka-shi, Miyazaki, Japan.

Days required for the transfer were 60 days from the day at which the composition was moved to the container. The composition was dissolved by external heating (steam of 150° C.) after the transfer, and was pumped into a catalyst reservoir in the diphenyl carbonate production facilities.

Results are shown in the following Table 11.

TABLE 11

| | Transferred composition | Transfer situation |
|---|---|---|
| Example 45 | Composition of example 24 | Whole liquid could be pumped into reservoir after dissolution for one day. |
| Example 46 | Composition of example 25 | Whole liquid could be pumped into reservoir after dissolution for three days. |
| Example 47 | Composition of example 31 | Whole liquid could be pumped into reservoir after dissolution for two days. |
| Example 48 | Composition of example 33 | Whole liquid could be pumped into reservoir after dissolution for three days. |

Examples 49 to 52

About 900 L of each of the polytitanoxane compositions having the aryloxy group, obtained in the examples 27, 28, 29, and 30 was put into a transport container (made of SUS304 and having two nozzles provided at upper and lower positions) of 1000 L. The container was transferred to diphenyl carbonate production facilities which was in Kurashiki-shi, Okayama, Japan from Nobeoka-shi, Miyazaki, Japan.

Days required for the transfer were 60 days from the day at which the composition was moved to the container. The composition was dissolved by external heating (steam of 150° C.) after the transfer, and was pumped into a catalyst reservoir provided in the diphenyl carbonate production facilities.

Results are shown in the following Table 12.

TABLE 12

| | Transferred composition | Transfer situation |
|---|---|---|
| Example 49 | Composition of example 27 | Although the liquid could be pumped after dissolution for four days, about several hundred grams of a solid content were left in the container. |
| Example 50 | Composition of example 28 | Although the liquid could be pumped after dissolution for five days, about several hundred grams of a solid content were left in the container. |
| Example 51 | Composition of example 29 | Although the liquid could be pumped after dissolution for five days, about several hundred grams of a solid content were left in the container. |
| Example 52 | Composition of example 30 | Although the liquid could be pumped after dissolution for five days, about several hundred grams of a solid content were left in the container. |

Comparative Examples 12 to 15

For comparison, about 900 L of each of the compositions obtained in the reference examples 5, 6, 7, and 8 was put into a transport container (made of SUS304 and having two nozzles provided at upper and lower positions) of 1000 L. The container was transferred to diphenyl carbonate production facilities which was in Kurashiki-shi, Okayama, Japan from Nobeoka-shi, Miyazaki, Japan.

Days required for the transfer were 60 days from the day at which the composition was moved to the container. The composition was dissolved by external heating (steam of 150° C.) after the transfer, and was pumped into a catalyst reservoir provided in the diphenyl carbonate production facilities.

Results are shown in the following Table 13.

TABLE 13

| | Transferred composition | Transfer situation |
|---|---|---|
| Comparative example 12 | Composition of reference example 5 | A composition could not be pumped since the composition was not dissolved after 10 days or more. |
| Comparative example 13 | Composition of reference example 6 | A composition could not be pumped since the composition was not dissolved after 10 days or more. |
| Comparative example 14 | Composition of reference example 7 | A composition could not be pumped since the composition was not dissolved after 10 days or more. |
| Comparative example 15 | Composition of reference example 8 | A composition could not be pumped since the composition was not dissolved after 10 days or more. |

Example 53

A method for producing a diaryl carbonate using a polytitanoxane composition having an aryloxy group as a catalyst was carried out.

A polytitanoxane composition having an aryloxy group was obtained by the same method as that of the above-mentioned [example 27]. A polytitanoxane composition having an aryloxy group, having a Ti concentration of 5% by mass (hereinafter, also described as a "titanium-containing composition") by further adding diphenyl carbonate was used as a catalyst.

A schematic configuration view of a producing apparatus of a diaryl carbonate is shown in FIG. 1.

The producing apparatus of the diaryl carbonate is equipped with distillation columns 110 and 120 which have a continuous multistage structure, a distillation column 130, and a distillation purification column 140.

These are connected via predetermined lines.

Specifically, lines 1 and 12 are feed lines supplying a feed compound and a polytitanoxane composition having an aryloxy group, or the like.

Lines 3 and 9 are recovery lines recovering a generated compound and other material.

Lines 2, 4, 5, 6, 7, 8, and 10 are transfer lines. A line 11 is a removing line.

Numeral numbers 111, 121, 131, and 141 designate reboilers, and numeral numbers 112, 122, 132, and 142 designate condensers.

Numeral number 113 designates a preheater for setting a supply material to a predetermined temperature.

The distillation column 110 had a continuous multistage structure, and was equipped with a concentration part and a recovery part. The concentration part was filled with sieve trays of 25 stages, and had an inner diameter of 150 mm and a length of 4.8 m. The recovery part was filled with Melapak CY (manufactured by Sulzer Chemtech Ltd., Switzerland), and had an inner diameter of 150 mm and a length of 2.3 m. In the distillation column 110, a mixed liquid was continuously supplied at about 1830 g/Hr from the feed line 1 through the preheater 113 from the sieve tray of the 25th stage to perform a transtransesterification reaction. The mixed liquid contains bis(3-methylbutyl)carbonate, phenol, and a polytitanoxane composition having an aryloxy group (a weight ratio of bis(3-methylbutyl)carbonate to phenol in the mixed liquid was adjusted to about 1.08, and titanium as atom was adjusted to about 500 ppm of the whole amount of the liquid).

The concentration part was provided below the stage continuously supplying the mixed liquid, and the recovery part was provided above the stage.

An amount of heat required for a reaction and distillation was supplied by providing an external heater, or by circulating a column lower liquid through the reboiler 111.

Thereby, a temperature of a column bottom of the multistage distillation column was controlled to about 230° C., and a pressure of a column top was controlled to about 140 kPa.

A reaction solution was continuously removed at about 1700 g/Hr through the transfer line 2 from the column bottom of the continuous multistage distillation column 110.

A low boiling component containing 3-methyl-1-butanol produced as by-product was removed from the column top. This was then condensed by the condenser 112, and was recovered by a reflux ratio of 2 from the recovery line 3.

The reaction solution removed from the transfer line 2 as described above was supplied to the continuous multistage distillation column 120.

The continuous multistage distillation column 120 is equipped with the concentration part having the reboiler 121 and a chimney type distillation column (an inner diameter of 150 mm, and a length of about 6 m) of five stages, and the recovery part filled with Melapak CY and having an inner diameter of 150 mm and a length of 3.8 m. The reaction solution was supplied at about 1700 g/Hr to the upper part of the concentration part.

The temperature of the column bottom of the distillation column 120 was controlled to 200° C., and the pressure of the column top was controlled to about 3 kPa. A disproportionation reaction was performed on this condition.

A low boiling component containing phenol and bis(3-methylbutyl)carbonate was circulated to the distillation column 110 through the condenser 122, the transfer line 5, and the feed line 1 from the column top of the distillation column 120.

From the column bottom of the distillation column 120, the reaction solution containing diphenyl carbonate was supplied to the distillation column 130 through the transfer line 4 to perform distillation separation.

The distillation column 130 is a distillation column filled with Melapak CY and having an inner diameter of 150 mm and a length of 4 m, and is provided with the reboiler 131 and the condenser 132.

A temperature of a column bottom of the distillation column 130 was controlled to about 180° C., and a pressure of a column top thereof was controlled to about 0.5 kPa.

The low boiling component containing diphenyl carbonate was removed from the column top, and was supplied to the distillation purification column 140 through the condenser 132 and the transfer line 7.

On the other hand, a high boiling component containing a catalyst was circulated to the distillation column 110 through the transfer line 6 and the feed line 1.

The distillation purification column 140 is a distillation column filled with Melapak CY and having an inner diameter of 150 mm and a length of 5 m, and is equipped with the reboiler 141 and the condenser 142.

The reaction solution containing diphenyl carbonate, supplied to the distillation purification column 140 through the transfer line 7 from the distillation column 130 was purified in the distillation purification column 140. Thereby, about 100% by mass of diphenyl carbonate was obtained from the recovery line 9 located above the column bottom and located below the distillation column.

The low boiling component containing 3-methyl butyl phenyl carbonate was circulated to the distillation column 120 through the recovery line 10 and the transfer line 2 from the column top of the distillation purification column 140.

A concentration of titanium atoms of a titanium-containing high-boiling substance removed from the removal line 11 was adjusted to about 5% by mass, and a concentration of titanium atoms in the titanium-containing composition supplied from the feed line 12 was adjusted to about 5% by mass. The supply of the titanium-containing composition from the feed line 1 was stopped.

Simultaneously, the amount of the liquid circulated to each of the distillation columns was gradually increased so that the amount of diphenyl carbonate recovered from the recovery line 9 was about 1000 g/Hr.

After the continuous operation described above was performed for about 12 hours, the continuous operation was in a steady state.

At this time, in the transfer line 2, the composition of the liquid contained about 15% by mass of phenol, about 67% by mass of bis(3-methylbutyl)carbonate, about 17% by mass of 3-methyl butyl phenyl carbonate, about 0.3% by mass of diphenyl carbonate, and about 0.2% by mass of 3-methyl-1-butanol. The flow rate was about 11402 g/Hr.

The residence times of the reaction solution in the steady state in the distillation column 110 and distillation column 120 were respectively about 1 Hr and about 2.5 Hr.

The composition of the liquid in the recovery line 3 contained about 100% by mass of 3-methyl-1-butanol. The flow rate was about 823 g/Hr.

In the transfer line 4, the composition of the liquid contained about 0.2% by mass of bis(3-methylbutyl)carbonate, about 18% by mass of 3-methyl butyl phenyl carbonate, and about 80% by mass of diphenyl carbonate. The flow rate was about 1238 g/Hr.

In the transfer line 5, the composition of the liquid contained about 0.2% by mass of 3-methyl-1-butanol, about 17% by mass of phenol, and about 83% by mass of bis(3-methylbutyl)carbonate. The flow rate was about 10300 g/Hr.

In the transfer line 7, the composition of the liquid contained about 88% by mass of diphenyl carbonate, about 12% by mass of 3-methyl butyl phenyl carbonate, and about 0.2% by mass of bis(3-methylbutyl)carbonate. The flow rate was about 1140 g/Hr.

After the continuous operation described above was further continued for about 100 Hr, the diphenyl carbonate recovered from the recovery line 9 was stably produced at about 1000 g/Hr. The diphenyl carbonate was a white solid at normal temperature (about 20° C.). When the diphenyl carbonate was analyzed, Ti was not detected (less than 1 ppm).

The titanium-containing high-boiling substance removed from the removal line 11 was then adjusted to about 1.8 g/Hr (the concentration of the titanium atoms was about 5% by mass), and the titanium-containing composition supplied from the feed line 12 was adjusted to about 1.8 g/Hr (the concentration of the titanium atoms was about 5% by mass). Similarly, the continuous operation was performed for about 200 Hr.

Similarly, the diaryl carbonate (diphenyl carbonate) recovered from the recovery line 9 was stably produced at about 1000 g/Hr. The diphenyl carbonate was a white solid at normal temperature (about 20° C.). When the diphenyl carbonate was analyzed, Ti was not detected (less than 1 ppm).

Example 54

A polytitanoxane composition having an aryloxy group to be used was obtained by the method described in the above-mentioned [example 38]. Furthermore, the polytitanoxane composition having the aryloxy group, adjusted so that a Ti concentration was 5% by mass was produced.

Diphenyl carbonate was produced in the same manner as in the above-mentioned [example 53] except for the condition.

The diphenyl carbonate recovered from the recovery line 9 was stably produced at about 1000 g/Hr.

The diphenyl carbonate was a white solid at normal temperature (about 20° C.). When the diphenyl carbonate was analyzed, Ti was not detected (less than 1 ppm).

Example 55

Di(n-butyl)carbonate was used as a dialkyl carbonate, and a polytitanoxane composition having an aryloxy group, obtained by the method described in the above-mentioned [example 25] and further adjusted so that a Ti concentration was 5% by mass was used.

Diphenyl carbonate was produced in the same manner as in the above-mentioned [example 53] except for the condition.

The diphenyl carbonate recovered from the recovery line 9 was stably produced at about 1000 g/Hr.

The diphenyl carbonate was a white solid at normal temperature (about 20° C.). When the diphenyl carbonate was analyzed, Ti was not detected (less than 1 ppm).

Example 56

In this example, a method for producing a diaryl carbonate using a polytitanoxane composition having an aryloxy group as a catalyst was carried out.

The polytitanoxane composition having the aryloxy group, manufactured by the same method as that of the above-mentioned [example 31] and further adjusted so that a Ti concentration was 5% by mass was obtained. The polytitanoxane composition having the aryloxy group was used as a catalyst.

In the polytitanoxane composition having the aryloxy group, phenyl salicylate having a higher boiling point than that of diphenyl carbonate was detected. The mole ratio of the phenyl salicylate to the titanium atoms was about 0.1.

Figure 2:
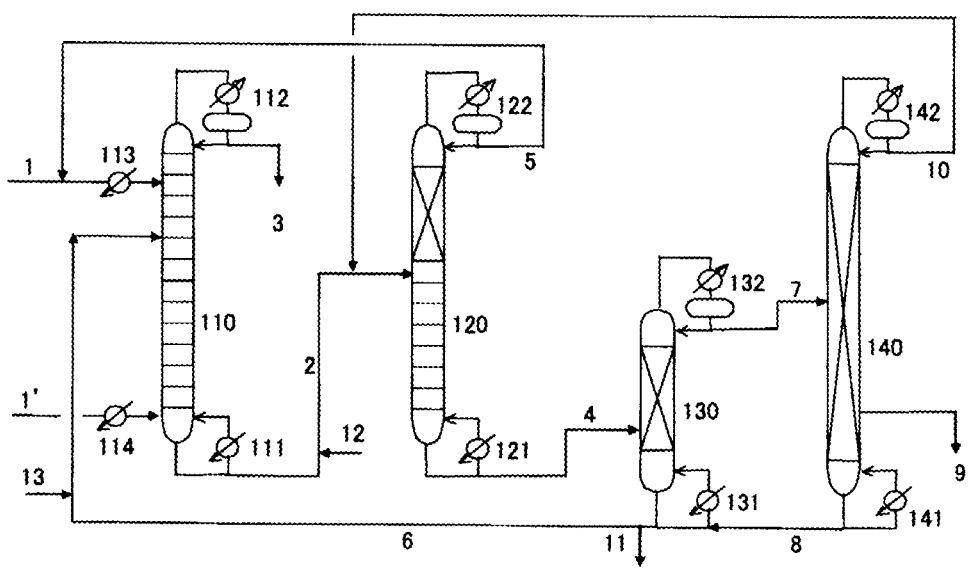
FIG. 2 shows a schematic configuration diagram of another example of an apparatus for producing a diaryl carbonate.

A schematic configuration view of a producing apparatus of a diaryl carbonate is shown in FIG. 2.

The producing apparatus of the diaryl carbonate is equipped with distillation columns 110 and 120 which have a continuous multistage structure, a distillation column 130, and a distillation purification column 140.

These are connected via predetermined lines.

Lines 1 and 12 are feed lines supplying a feed compound and a polytitanoxane composition having an aryloxy group, or the like.

Lines 3 and 9 are recovery lines recovering a generated compound and other material.

Lines 2, 4, 5, 6, 7, 8, and 10 are transfer lines. A line 11 is a removing line.

Numeral numbers 111, 121, 131, and 141 designate reboilers, and numeral numbers 112, 122, 132, and 142 designate condensers.

Numeral number 113 designates a preheater for setting a supply material to a predetermined temperature.

The distillation column 130 is a distillation column filled with Melapak CY and having an inner diameter of 150 mm and a length of 4 m, and is provided with the reboiler 131 and the condenser 132.

About 10 kg of the polytitanoxane composition having the aryl group (titanium concentration: about 5% by mass) was supplied to the lower part of the distillation column 130, and the temperature of the polytitanoxane composition having the aryl group was controlled to about 200° C.

After this state was held for about 72 Hr, part of the polytitanoxane composition having the aryl group was sampled and analyzed. Phenyl salicylate having a higher boiling point than that of the diphenyl carbonate was detected. The mole ratio of the phenyl salicylate to the titanium atoms was about 0.5.

A mixture of a high-boiling substance generated in the distillation column 130 and a titanium-containing composition is defined as a composition A. The composition A was used as a reaction catalyst for the next production of the diaryl carbonate (diphenyl carbonate).

In the distillation column 110 filled with sieve trays of 50 stages, having an inner diameter of 150 mm and a length of 12 m, and having a continuous multistage structure, a mixed liquid containing about 30% by mass of dimethyl carbonate and about 70% by mass of phenol was continuously supplied at about 41 kg/Hr to the sieve tray of the 50th stage from the feed line 1 through the preheater 113. On the other hand, a mixed liquid containing about 70% by mass of dimethyl carbonate and about 30% by mass of phenol was continuously supplied at about 41 kg/Hr to the lower part of the distillation column 110 from a feed line 1'.

A concentration part was provided below a stage continuously supplying the mixed liquid. A recovery part was provided above the stage.

An amount of heat required for a reaction and distillation was supplied by providing an external heater, or by circulating a column lower liquid through the reboiler 111.

Thereby, a temperature of a column bottom of a multistage distillation column was controlled to about 230° C., and a pressure of a column top was controlled to about 0.55 MPa-G.

The polytitanoxane composition having the aryloxy group was gradually supplied to the 45th stage of the distillation column 110 from the lower part of the distillation column 130 using the transfer line 6 to adjust the concentration of the titanium atoms in the column bottom of the distillation column 110 to about 300 ppm.

The reaction solution was continuously removed at about 21 kg/Hr through the transfer line 2 from the column bottom of the continuous multistage distillation column 110.

The low boiling component containing methanol produced as by-product was removed from the column top. This was then condensed by the condenser 112, and was recovered from the recovery line 3.

The reaction solution removed from the transfer line 2 as described above was supplied to the continuous multistage distillation column 120.

This continuous multistage distillation column 120 was equipped with a concentration part and a recovery part. The concentration part had a reboiler 121 and a sieve tray type distillation column of 16 stages (an inner diameter of 150 mm, and a length of about 4 m). The recovery part was filled with Melapak CY and had an inner diameter of 150 mm and a length of 4 m. The reaction solution was supplied at about 21 kg/Hr to the upper part of the concentration part.

The temperature of the column bottom of the distillation column 120 was controlled to about 210° C., and the pressure of the column top was controlled to about 13.3 kPa. A disproportionation reaction was performed on this condition.

The low boiling component containing phenol and dimethyl carbonate was circulated to the distillation column 110 through the condenser 122, the transfer line 5, and the feed line 1 from the column top of the distillation column 120.

From the column bottom of the distillation column 120, the reaction solution containing diphenyl carbonate was supplied to the distillation column 130 through the transfer line 4 to perform distillation separation.

The distillation column 130 is a distillation column filled with Melapak CY and having an inner diameter of 150 mm and a length of 4 m, and is provided with the reboiler 131 and the condenser 132.

A temperature of a column bottom of the distillation column 130 was controlled to about 190° C., and a pressure of a column top was controlled to about 1.7 kPa.

The low boiling component containing diphenyl carbonate was removed from the column top, and was supplied to the distillation purification column 140 through the condenser 132 and the transfer line 7.

On the other hand, a high boiling component containing a catalyst was circulated to the distillation column 110 through the transfer line 6 and the feed line 1.

The distillation purification column 140 is a distillation column filled with Melapak CY and having an inner diameter of 150 mm and a length of 5 m, and is equipped with the reboiler 141 and the condenser 142.

The reaction solution containing diphenyl carbonate, supplied to the distillation purification column 140 through the transfer line 7 from the distillation column 130 is purified in the distillation purification column 140. Thereby, 99.8% by mass of diphenyl carbonate was obtained from the recovery line 9 located above the column bottom and located below the distillation column.

The low boiling component containing methyl phenyl carbonate was circulated to the distillation column 120 through the recovery line 10 and the transfer line 2 from the column top of the distillation purification column 140.

After the continuous operation described above was performed for about 12 hours, the continuous operation was in a steady state.

At this time, in the transfer line 2, the composition of the liquid contained about 55% by mass of phenol, about 26% by mass of dimethyl carbonate, about 17% by mass of methyl phenyl carbonate, about 2% by mass of diphenyl carbonate, and about 0.09% by mass of methanol. The flow rate was about 40 kg/Hr.

In the transfer line 4, the composition of the liquid contained about 0.1% by mass of dimethyl carbonate, about 17% by mass of methyl phenyl carbonate, about 3% by mass of phenol, and about 80% by mass of diphenyl carbonate. The flow rate was about 6.2 kg/Hr.

In the transfer line 7, the composition of the liquid contained about 78% by mass of diphenyl carbonate, about 19% by mass of methyl phenyl carbonate, and about 3% by mass of phenol. The flow rate was about 5 kg/Hr.

After the continuous operation described above was further continued for about 100 Hr, the diphenyl carbonate recovered from the recovery line 9 was stably produced at about 4 kg/Hr.

When a titanium-containing high-boiling substance obtained from the removing line 11 was analyzed, a ratio of total moles of phenyl salicylate and methyl ester salicylate to moles of titanium atoms was about 1.1.

When the continuous operation described above was further continued for about 500 Hr, the diphenyl carbonate recovered from the recovery line 9 was stably produced at about 4 kg/Hr. The diphenyl carbonate was a white solid at normal temperature (about 20° C.). When the diphenyl carbonate was analyzed, Ti was not detected (less than 1 ppm).

The titanium-containing high-boiling substance removed from the removal line 11 was then adjusted to about 2.0 g/Hr (the concentration of the titanium atoms was about 5% by mass), and the titanium-containing composition supplied from the feed line 12 was adjusted to about 2.0 g/Hr (the concentration of the titanium atoms was about 5% by mass). Similarly, the continuous operation was performed for about 500 Hr.

Similarly, the diaryl carbonate (diphenyl carbonate) recovered from the recovery line 9 was stably produced at about 4 kg/Hr. The diphenyl carbonate was a white solid at normal temperature (about 20° C.). When the diphenyl carbonate was analyzed, Ti was not detected (less than 1 ppm).

Example 57

In this example, a method for producing a diaryl carbonate using a polytitanoxane composition having an aryloxy group as a catalyst was carried out.

A polytitanoxane composition having an aryloxy group, manufactured by the same method as that of the above-mentioned [example 42] and further adjusted so that a Ti concentration was 5% by mass was obtained. The polytitanoxane composition having the aryloxy group (in the composition, phenyl salicylate having a higher boiling point than that of diphenyl carbonate was detected, and the mole ratio of the phenyl salicylate to the titanium atoms was about 0.1) was used as the catalyst.

The method was carried out in the same manner as in the above-mentioned [example 56] except for the condition.

Similarly, the diaryl carbonate (diphenyl carbonate) recovered from the recovery line 9 was stably produced at about 4 kg/Hr. The diphenyl carbonate was a white solid at normal temperature (about 20° C.). When the diphenyl carbonate was analyzed, Ti was not substantially detected (less than 1 ppm).

Comparative Example 16

A diaryl carbonate was produced using the producing apparatus for the diaryl carbonate described in the above-mentioned [example 53] and shown in FIG. 1.

A polytitanoxane composition having an aryloxy group, manufactured by the same method as that of the above-mentioned [reference example 5] and further adjusted by adding diphenyl carbonate so that a Ti concentration was 5% by mass, was used as a catalyst.

Comparative example 16 was carried out in the same manner as in the above-mentioned [example 53] except for the condition.

The amount of the diaryl carbonate (diphenyl carbonate) recovered from the recovery line 9 was about 1000 g/Hr.

The diphenyl carbonate was a yellowish-white solid at normal temperature (about 20° C.). When the diphenyl carbonate was analyzed, the diphenyl carbonate contained 10 ppm of Ti.

Comparative Example 17

A polytitanoxane composition having an aryloxy group, manufactured by the same method as that of the above-mentioned reference example 8 and further adjusted so that a Ti concentration was 5% by mass was obtained. The polytitanoxane composition having the aryloxy group was used as a catalyst.

The comparative example 17 was carried out in the same manner as in the above-mentioned [example 56] except for the condition.

Similarly, the diphenyl carbonate recovered from the recovery line 9 was stably produced at about 4 kg/Hr.

The diphenyl carbonate was a yellowish-white solid at normal temperature (about 20° C.). When the diphenyl carbonate was analyzed, the diphenyl carbonate contained 20 ppm of Ti.

A white solid content was deposited on the column top of the distillation column 110.

Comparative Example 18

A polytitanoxane composition having an aryloxy group was manufactured by the same method as that of the example 29. A titanium content in the composition was further adjusted to 16% by mass (a diaryl carbonate content: 4% by mass, and a content of a compound having a boiling point of 150° C. or less (n-butanol, water): 1 ppm or less).

The obtained polytitanoxane composition having the aryloxy group was stored by the same method as those of the examples 34 to 44. The inside of the container was confirmed after the storage. A portion of the composition near the wall surface of the container was sampled, and was subjected to metal analysis. Concentrations of metals other than Ti were increased by 10% or more compared with the content of the analyzed value before the storage.

Comparative Example 19

A polytitanoxane composition having an aryloxy group was manufactured by the same method as that of the example 29. A titanium content in the composition was further adjusted to 16% by mass (a diaryl carbonate content: 4% by mass, and a content of a compound having a boiling point of 150° C. or less (n-butanol, water): 1 ppm or less).

The obtained polytitanoxane composition having the aryloxy group was put into a transport container by the same method as those of the examples 45 to 48. The container was transferred to diphenyl carbonate production facilities which was in Kurashiki-shi, Okayama, Japan from Nobeoka-shi, Miyazaki, Japan. Days required for the transfer were 60 days from the day at which the composition was moved to the container. The composition was dissolved by external heating (steam of 150° C.) after the transfer, and was attempted to be pumped into a catalyst reservoir provided in the diphenyl carbonate production facilities. However, the composition was not dissolved even after 10 days or more, and could not be pumped.

Comparative Example 20

A polytitanoxane composition having an aryloxy group was manufactured by the same method as that of the example 30. A titanium content in the composition was further adjusted to 17% by mass (a diaryl carbonate content: 9% by mass, and a content of a compound having a boiling point of 150° C. or less (n-butanol, water): 1 ppm or less).

The obtained polytitanoxane composition having the aryloxy group was stored by the same method as those of the examples 34 to 44. The inside of the container was confirmed after the storage. A portion of the composition near the wall surface of the container was sampled, and was subjected to metal analysis. Concentrations of metals other than Ti were increased by 10% or more compared with the content of the analyzed value before the storage.

Comparative Example 21

A polytitanoxane composition having an aryloxy group was manufactured by the same method as that of the example 30. A titanium content in the composition was further adjusted to 17% by mass (a diaryl carbonate content: 9% by mass, and a content of a compound having a boiling point of 150° C. or less (n-butanol, water): 1 ppm or less).

The obtained polytitanoxane composition having the aryloxy group was put into a transport container by the same method as those of the examples 45 to 48. The container was transferred to diphenyl carbonate production facilities which was in Kurashiki-shi, Okayama, Japan from Nobeoka-shi, Miyazaki, Japan. Days required for the transfer were 60 days from the day at which the composition was moved to the container. The composition was dissolved by external heating (steam of 150° C.) after the transfer, and was attempted to be pumped into a catalyst reservoir provided in the diphenyl carbonate production facilities. However, the composition was not dissolved even after 10 days or more, and could not be pumped.

Reference Example 13

After the reaction solution obtained in the above-mentioned [example 1] was returned to a normal pressure with nitrogen, diphenyl carbonate was added in an amount of 4.5 mol per mol of Ti atoms contained in the reaction solution, under stirring.

In this case, an internal liquid temperature of the reactor was 110° C., and the diphenyl carbonate was also added in a molten state of about 110° C. The reaction solution was a red liquid.

The addition time was about 1 hour.

The temperature of the liquid of the reactor was gradually raised to about 310° C., and the internal pressure of the reactor was gradually lowered, thereby starting the distillation of a component having a lower boiling point than that of the diphenyl carbonate, together with the diphenyl carbonate from the distillation column.

After the pressure within the system was gradually returned to a normal pressure with nitrogen gas when about a half amount of the added diphenyl carbonate was distilled (finally, the temperature within the system was about 309° C., and the pressure was about 90 kPa), diphenyl carbonate in about a half amount of that of the previously added diphenyl carbonate was added again.

The diphenyl carbonate was added in a molten state of about 110° C.

The addition time was about 1 hour.

The temperature of the reaction solution was then set to about 310° C., and the internal pressure of the reactor was gradually lowered, thereby starting the distillation of a component having a lower boiling point than that of the diphenyl carbonate, together with the diphenyl carbonate from the distillation column.

The pressure within the system was gradually returned to a normal pressure with nitrogen gas when diphenyl carbonate in nearly the same amount as that of the diphenyl carbonate added at the second time was distilled (finally, the temperature within the system was about 308° C., and the pressure was about 89 kPa). The same operation as that of the above description was performed, and operation for distilling the component having a lower boiling point than that of the diphenyl carbonate, together with the diphenyl carbonate was performed five times in total.

A component containing the diphenyl carbonate evaporated at the first time was colored in orange, and contained about 350 ppm of Ti atoms.

The component contained about 400 ppm of a chlorine component.

A component containing the diphenyl carbonate evaporated at the second time was colored in yellow, and contained about 230 ppm of Ti atoms. Components containing the diphenyl carbonate evaporated at the third time, at the fourth time, and at the fifth time were also colored in yellow, and contained 200 ppm, 190 ppm, and 210 ppm of Ti atoms, respectively.

The polytitanoxane composition was changed into black. Even when the polytitanoxane composition was cooled to normal temperature, the polytitanoxane composition was not changed to a solid, but tarry. A Ti—O—Ti linkage could not be confirmed since the composition was tarry.

Example 58

Preparation of Aryloxytitanium Composition 200 kg of polytitanoxane butoxide (manufactured by E.I. du Pont de Nemours & Company, trade name: Tyzor BTP) was fed under a nitrogen atmosphere to a batch type reactor equipped with a stirrer, a heater, and a distillation column and having a volume of 1800 L, and 485 kg of distillation-purified phenol was then fed.

Next, the mixture in the batch type reactor was heated to 180° C. under a normal pressure by a heater and reacted. N-butanol generated by the reaction was recovered from a column top of the distillation column. The batch type reactor was depressurized to about 53 kPa, and n-butanol was recovered.

The batch type reactor was then returned to a normal pressure. About 450 kg (an amount of 3.6 mol per mol of Ti atoms contained in a reaction solution) of diphenyl carbonate was fed. The mixture in the reactor was heated to about 190° C. Next, the batch type reactor was depressurized to about 1.3 kPa, and the diphenyl carbonate containing the low boiling component was evaporated so as to obtain an aryloxytitanium composition. Diphenyl carbonate was added so that the titanium concentration of the obtained aryloxytitanium composition was 5% by mass.

(Producing Apparatus of Diaryl Carbonate)

A schematic configuration view of a producing apparatus used in the example 58 is shown in FIG. 2.

The producing apparatus is equipped with distillation columns 110 and 120 which have a continuous multistage structure, a distillation column 130, and a distillation purification column 140.

These are connected via predetermined lines.

Specifically, lines 1, 1', 12, and 13 are feed lines supplying a feed compound and an aryloxytitanium composition, or the like. Lines 3 and 9 are recovery lines recovering a generated compound and other material. Lines 2, 4, 5, 6, 7, 8, and 10 are transfer lines. A line 11 is a removing line.

Numeral numbers 111, 121, 131, and 141 designate reboilers, and numeral numbers 112, 122, 132, and 142 designate condensers. Numeral number 113 designates a preheater for setting a supply material to a predetermined temperature.

(Preparation of Reaction Catalyst)

In the distillation column 130, as described below, a product having a high boiling point than that of the diphenyl carbonate was produced to prepare a reaction catalyst.

The distillation column 130 was a distillation column filled with Melapak CY and having an inner diameter of 3.4 m and a length of 17 m, and was equipped with a reboiler 131 and a condenser 132.

About 5200 kg of the prepared aryloxytitanium composition (titanium concentration: about 5% by mass) was supplied to the lower part of the distillation column 130. The temperature of the aryloxytitanium composition was controlled to about 200° C. This state was held for about 60 hr. When part of the aryloxytitanium composition was then sampled and analyzed, phenyl salicylate having a higher boiling point than that of the diphenyl carbonate was detected. The mole ratio (phenyl salicylate/titanium atoms) of the phenyl salicylate and the titanium atom was about 0.4. A mixture (hereinafter, also described as "composition A") of the high boiling point product generated in the distillation column 130 and the aryloxytitanium composition was used as a reaction catalyst for the next production of a diaryl carbonate.

(Production of Diaryl Carbonate)

The distillation column 110 had a continuous multistage structure, and was filled with sieve trays of 80 stages and had an inner diameter of 5 m and a length of 33 m. A mixed liquid (a) containing about 30% by mass of dimethyl carbonate and about 70% by mass of phenol was continuously supplied at about 57 ton/Hr to the upper part of the distillation column 110 from the feed line 1 through the preheater 113. On the other hand, a mixed liquid (b) containing about 70% by mass of dimethyl carbonate and about 30% by mass of phenol was continuously supplied at about 57 ton/Hr to the lower part of the distillation column 110 from the feed line 1'.

The concentration part was provided below the stage continuously supplying the mixed liquids (a) and (b), and the recovery part was provided above the stage.

An amount of heat required for a reaction and distillation was controlled by providing an external heater, or by circulating a column lower liquid through the reboiler. The method controlled a temperature of a column bottom of the multistage distillation column 110 to about 230° C., and controlled a pressure of a column top to about 0.55 MPa-G.

Next, the prepared reaction catalyst (composition A) was slowly supplied to the upper part of the distillation column 110 from the lower part of the distillation column 130 using the transfer line 6, and a concentration of titanium atoms in a reaction solution of the distillation column 110 was adjusted to about 300 ppm. The reaction solution was continuously removed at about 60 ton/Hr through the transfer line 2 from the column bottom of the continuous multistage distillation column 110.

A low boiling component containing methanol produced as by-product was continuously removed from the column top of the distillation column 110.

The removed reaction solution from the transfer line 2 as described above was supplied to the continuous multistage distillation column 120.

This continuous multistage distillation column 120 had an inner diameter of 5 m and a length of 31 m. The continuous multistage distillation column 120 was equipped with a sieve tray type concentration part of 30 stages, a recovery part filled with Melapak CY, a condenser 122, and a reboiler 121. The supplying position of the reaction solution was set to the upper part of the concentration part, and the supply rate of the reaction solution was set to about 60 ton/Hr.

The temperature of the column bottom of the distillation column 120 was controlled to about 210° C., and the pressure of the column top was controlled to about 13.3 kPa. A disproportionation reaction was performed on this condition.

A low boiling component containing phenol and dimethyl carbonate was circulated to the distillation column 110 through the condenser 122, the transfer line 5, and the feed line 1 from the column top of the distillation column 120.

From the column bottom of the distillation column 120, about 14 ton/Hr of the reaction solution containing diphenyl carbonate was supplied to the distillation column 130 through the transfer line 4 to perform distillation separation.

The distillation column 130 was a distillation column filled with Melapak CY and having an inner diameter of 3.4 m and a length of 17 m, and was provided with the reboiler 131 and the condenser 132.

A temperature of a column bottom of the distillation column 130 was controlled to about 190° C., and a pressure of a column top was controlled to about 1.7 kPa.

The low boiling component containing diphenyl carbonate was removed from the column top, and was supplied to the distillation purification column 140 through the condenser 132 and the transfer line 7.

On the other hand, a high boiling component containing a reaction catalyst (composition A) was circulated to the distillation column 110 through the transfer line 6 and the feed line 1.

The distillation purification column 140 was a distillation column filled with Melapak CY and having an inner diameter of 2.8 m and a length of 22 m, and was equipped with the reboiler 141 and the condenser 142.

The reaction solution containing diphenyl carbonate supplied to the distillation purification column 140 through the transfer line 7 from the distillation column 130 was purified in the distillation purification column 140. 99.8% by mass of diphenyl carbonate (diaryl carbonate) was obtained from the recovery line 9 by the purification. The position of the recovery line 9 was set to the lower part of the distillation column located above the column bottom.

The low boiling component containing methyl phenyl carbonate was removed from the column top of the distillation purification column 140, and was circulated to the distillation column 120 through the recovery line 10 and the transfer line 2.

After the continuous operation described above was performed for about 24 hours, the continuous operation was in a steady state.

At this time, in the transfer line 2, the composition of the liquid contained about 55% by mass of phenol, about 26% by mass of dimethyl carbonate, about 17% by mass of methyl phenyl carbonate, about 2% by mass of diphenyl carbonate, and about 0.09% by mass of methanol. The flow rate was about 60 ton/Hr.

In the transfer line 4, the composition of the liquid contained about 0.1% by mass of dimethyl carbonate, about 27% by mass of methyl phenyl carbonate, about 3% by mass of phenol, and about 70% by mass of diphenyl carbonate. The flow rate was about 14 ton/Hr.

In the transfer line 7, the composition of the liquid contained about 65% by mass of diphenyl carbonate, about 33% by mass of methyl phenyl carbonate, and about 2% by mass of phenol. The flow rate was about 13 ton/Hr.

After the continuous operation described above was further continued for about 100 Hr, diphenyl carbonate (diaryl carbonate) recovered from the recovery line 9 was stably produced at about 7.5 ton/Hr. The diphenyl carbonate was a white solid at normal temperature (about 20° C.). When the diphenyl carbonate was analyzed, Ti was not detected (less than 1 ppm).

After the continuous operation described above was further continued for about 500 Hr, diphenyl carbonate (diaryl carbonate) recovered from the recovery line 9 was stably produced at about 7.6 ton/Hr. The diphenyl carbonate was a white solid at normal temperature (about 20° C.). When the diphenyl carbonate was analyzed, Ti was not detected (less than 1 ppm).

Comparative Example 22

After the reaction solution obtained in the above-mentioned [example 8] was returned to a normal pressure with nitrogen, diphenyl carbonate was added in an amount of 0.06 mol per mol of Ti atoms contained in the reaction solution, under stirring.

In this case, an internal liquid temperature of the reactor was 170° C., and the diphenyl carbonate was also added in a molten state of about 170° C. The reaction solution was a red liquid.

The addition time was about 2 minutes.

The temperature of the liquid of the reactor was gradually raised to about 210° C., and the internal pressure of the reactor was gradually lowered, thereby starting the distillation of a component having a lower boiling point than that of the diphenyl carbonate, together with the diphenyl carbonate from the distillation column.

When about 20% of the added diphenyl carbonate was distilled (finally, the temperature within the system was about 211° C., and the pressure was about 3 kPa), the pressure in the distillation column was unstabilized, and the component having a lower boiling point than that of the diphenyl carbonate could not be distilled together with the diphenyl carbonate from the distillation column. When the distillation column was examined, a tarry product having high viscosity was present on the column top.

The average degree of polymerization of the obtained polytitanoxane composition having the aryloxy group and the Ti—O—Ti linkage were not changed before and after the step. The polytitanoxane composition had 17% by mass of a titanium content and about 2% by mass of a diaryl carbonate content.

The polytitanoxane composition was put into a transport container by the same method as those of the examples 45 to 48. The container was transferred to diphenyl carbonate production facilities which was in Kurashiki-shi, Okayama, Japan from Nobeoka-shi, Miyazaki, Japan. Days required for the transfer were 60 days from the day at which the composition was moved to the container. The composition was dissolved by external heating (steam of 150° C.) after the transfer, and was attempted to be pumped into to a catalyst reservoir provided in the diphenyl carbonate production facilities. However, the composition was not dissolved even after 10 days or more, and could not be pumped.

Comparative Example 23

After the reaction solution obtained in the above-mentioned [example 4] was returned to a normal pressure with nitrogen, diphenyl carbonate was added in an amount of 60 mol per mol of Ti atoms contained in the reaction solution, under stirring.

In this case, an internal liquid temperature of the reactor was 170° C., and the diphenyl carbonate was also added in a molten state of about 170° C. The reaction solution was a red liquid.

The addition time was about 6 hours.

The temperature of the liquid of the reactor was gradually raised to about 210° C., and the internal pressure of the reactor was gradually lowered, thereby starting the distillation of a component having a lower boiling point than that of the diphenyl carbonate, together with the diphenyl carbonate from the distillation column.

When about 30% of the added diphenyl carbonate was distilled (finally, the temperature within the system was about 209° C., and the pressure was about 3 kPa), the pressure in the system was gradually returned to a normal pressure with nitrogen gas. Then, diphenyl carbonate of about 30% of the previously added amount was added again.

The diphenyl carbonate was added in a molten state of about 110° C.

The addition time was about 2 hours.

The temperature of the reaction solution was then set at about 210° C., and the internal pressure of the reactor was gradually lowered, thereby starting the distillation of a component having a lower boiling point than that of the diphenyl carbonate, together with the diphenyl carbonate from the distillation column.

The pressure within the system was gradually returned to a normal pressure with nitrogen gas when diphenyl carbonate in nearly the same amount as that of the diphenyl carbonate added at the second time was distilled (finally, the temperature within the system was about 211° C., and the pressure was about 3 kPa). The same operation as that of the above description was performed, and operation for distilling the component having a lower boiling point than that of the diphenyl carbonate, together with the diphenyl carbonate was performed five times in total.

A component containing the diphenyl carbonate evaporated at the first time was colored in light yellow, and contained about 8 ppm of Ti atoms. The component also contained a chlorine component of about 5 ppm.

A component containing the diphenyl carbonate evaporated at the second time was colored in light yellow, and contained about 4 ppm of Ti atoms. Components containing the diaryl carbonate evaporated at the third time, at the fourth time, and at the fifth time were colored in light yellow, and contained 3 ppm, 2 ppm, and 3 ppm of Ti atoms, respectively.

The polytitanoxane composition had about 0.5% by mass of a titanium content and about 97% by mass of a diaryl carbonate content.

The polytitanoxane composition was stored by the same method as those of the examples 34 to 44. The inside of the container was confirmed after the storage. A portion of the composition near the wall surface of the container was sampled, and was subjected to metal analysis. Concentrations of metals other than Ti were increased by 10% or more compared with the content of the analyzed value before the storage.

INDUSTRIAL APPLICABILITY

The present invention has industrial applicability as a production technique of a catalyst used when producing aromatic carbonates while reacting aliphatic carbonate and an aromatic monohydroxy compound and removing alcohols produced as by-product to the outside of the reaction system.

DESCRIPTION OF REFERENCE NUMERALS 1, 1', 12, 13 FEED LINE
3, 9 RECOVERY LINE
2, 4, 5, 6, 7, 8, 10 TRANSFER LINE
11 REMOVAL LINE
110, 120, 130 DISTILLATION COLUMN
140 DISTILLATION PURIFICATION COLUMN
111, 121, 131, 141 REBOILER
112, 122, 132, 142 CONDENSER
113, 114 PREHEATER

What is claimed is:

1. A method for producing an aryloxytitanium composition, comprising a step (1) of adding a diaryl carbonate to an organic oxytitanium composition having an R—O—Ti linkage where R represents an organic group containing 1 to 20 carbon atoms, and evaporating a component having a lower boiling point than that of the diaryl carbonate, together with the diaryl carbonate, so as to obtain an aryloxytitanium composition, wherein
an amount of the diaryl carbonate used in the step (1) is 0.1 to 50 molar equivalents with respect to total moles of Ti atoms contained in the organic oxytitanium composition having the R—O—Ti linkage.

2. The method for producing the aryloxytitanium composition according to claim 1, wherein a temperature in evaporating the component having the lower boiling point than that of the diaryl carbonate in the step (1) is in a range of 50° C. to 250° C., and
in the aryloxytitanium composition obtained in the step (1), a content of titanium atoms is 1% by mass or more and 15% by mass or less, and a content of the diaryl carbonate is 50% by mass or more and 95% by mass or less.

3. The method for producing the aryloxytitanium composition according to claim 1, wherein in the step (1), the following step (A) and step (B) are sequentially performed:
step (A): a step of reacting an alkyloxytitanium composition with an aromatic hydroxy compound and evaporating an alcohol as by-product, by distillation, so as to obtain a crude aryloxytitanium composition; and
step (B): a step of adding a diaryl carbonate to the crude aryloxytitanium composition and evaporating a component having a lower boiling point than that of the diaryl carbonate, together with the diaryl carbonate, so as to obtain an aryloxytitanium composition.

4. The method for producing the aryloxytitanium composition according to claim 1, comprising further carrying out the following step (C):
step (C): a step of adjusting a component ratio of the aryloxytitanium composition and the diaryl carbonate.

5. The method for producing the aryloxytitanium composition according to claim 3, wherein the alkyloxytitanium composition is an alkyloxytitanium composition obtained by sequentially or simultaneously performing
step (X): a step of adding water to a tetraalkoxytitanium to react the tetraalkoxytitanium with the water so as to obtain a partial hydrolysis reaction solution, and
step (Y): a step of evaporating an alcohol as by-product, from the hydrolysis reaction solution.

6. The method for producing the aryloxytitanium composition according to claim 1, wherein an aryloxy group constituting the aryloxytitanium is represented by the following formula (ArO):

[Formula 1]

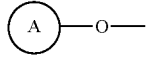
(ArO)

wherein a ring A represents an organic group having 6 to 20 carbon atoms, containing an aromatic group to which an oxygen atom bonded to Ti is bonded at any position keeping aromaticity, and may be a single ring or a plurality of rings, or a heterocyclic ring, and/or may be substituted by another substituent.

7. The method for producing the aryloxytitanium composition according to claim 5, wherein an amount of the water in the step (X) is 0.1 to 0.92 molar equivalents with respect to the tetraalkoxytitanium.

8. The method for producing the aryloxytitanium composition according to claim 1, comprising carrying out the step (1) or the step (B) in multiple batches, or continuously.

9. An aryloxytitanium composition produced by the method for producing the aryloxytitanium composition according to claim 1.

10. An aryloxytitanium composition comprising:
an aryloxytitanium composition produced by the method for producing the aryloxytitanium composition according to claim 1; and
a diaryl carbonate.

11. The method for producing the aryloxytitanium composition according to claim 1, wherein the diaryl carbonate is diphenyl carbonate.

12. The method for producing the aryloxytitanium composition according to claim 1, wherein an aryloxy group constituting the aryloxytitanium is the same aryloxy group as an aryloxy group constituting the diaryl carbonate.

13. A method for stabilizing an aryloxytitanium composition, comprising:
a step of reacting an alkyloxytitanium composition with an aromatic hydroxy compound and evaporating an alcohol as by-product, by distillation, so as to obtain a crude aryloxytitanium composition (step (A)); and
a step of adding a diaryl carbonate to the crude aryloxytitanium composition and evaporating a component having a lower boiling point than that of the diaryl carbonate, together with the diaryl carbonate, so as to obtain an aryloxytitanium composition (step (B)), wherein
an amount of the diaryl carbonate used in the step (B) is 0.1 to 50 molar equivalents with respect to total moles of Ti atoms contained in the crude aryloxytitanium composition, and
a temperature in evaporating the component having a lower boiling point than that of the diaryl carbonate in the step (B) is in a range of 50° C. to 250° C.

14. The method for stabilizing the aryloxytitanium composition according to claim 13, wherein in the aryloxytitanium composition obtained in the step (B), a content of titanium atoms is 1% by mass or more and 15% by mass or less, and a content of the diaryl carbonate is 50% by mass or more and 95% by mass or less.

15. An aryloxytitanium composition comprising:
an aryloxytitanium; and
a diaryl carbonate, wherein
a content of titanium atoms constituting the aryloxytitanium is 1% by mass or more and 15% by mass or less.

16. The aryloxytitanium composition according to claim 15, wherein a content of the diaryl carbonate is 50% by mass or more and 95% by mass or less, and a content of a compound having a boiling point of 150° C. or less is 1000 ppm or less.

17. The aryloxytitanium composition according to claim 15, wherein the content of titanium atoms constituting the aryloxytitanium is 5% by mass or more and 10% by mass or less.

18. The aryloxytitanium composition according to claim 15, wherein a total content of the aryloxytitanium and the diaryl carbonate is 50% by mass or more.

19. The aryloxytitanium composition according to claim 15, wherein titanium constituting the aryloxytitanium is a tetravalent titanium.

20. The aryloxytitanium composition according to claim 15, wherein an aryloxy group constituting the aryloxytitanium is an aryloxy group having 6 or 7 carbon atoms.

21. The aryloxytitanium composition according to claim 15, wherein the composition is solid or liquid.

22. The aryloxytitanium composition according to claim 15, wherein the aryloxytitanium is an aryloxypolytitanoxane.

23. The aryloxytitanium composition according to claim 22, wherein the aryloxypolytitanoxane comprises
one or more types of aryloxypolytitanoxane having one or more Ti—O—Ti linkages in one molecule.

24. A method for producing a diaryl carbonate, using the aryloxytitanium composition according to claim 15 as a catalyst, comprising
performing transesterification and disproportionation reactions, using a dialkyl carbonate, an aromatic hydroxy compound, and the aryloxytitanium composition, so as to produce a diaryl carbonate.

25. A catalyst for production of a diaryl carbonate, comprising an aryloxytitanium and a diaryl carbonate, wherein
a content of titanium atoms constituting the aryloxytitanium is 1% by mass or more and 15% by mass or less.

26. A method for producing a diaryl carbonate, comprising performing transesterification reaction and disproportionation reaction, using a dialkyl carbonate and an aromatic hydroxy compound, in the presence of the catalyst for production of the diaryl carbonate according to claim 25, so as to produce a diaryl carbonate.

27. The method for producing the diaryl carbonate according to claim 26, comprising a step of separating the diaryl carbonate from a reaction product obtained by the disproportionation reaction.

28. The method for producing the diaryl carbonate according to claim 27, further comprising a step of recycling the reaction product, from which the diaryl carbonate is separated, into the transesterification reaction or the disproportionation reaction.

* * * * *